(12) United States Patent
Lu et al.

(10) Patent No.: US 10,738,048 B2
(45) Date of Patent: *Aug. 11, 2020

(54) BICYCLIC HETEROCYCLES AS FGFR4 INHIBITORS

(71) Applicant: Incyte Corporation, Wilmington, DE (US)

(72) Inventors: Liang Lu, Hockessin, DE (US); Liangxing Wu, Wilmington, DE (US); Ding-Quan Qian, Newark, DE (US); Wenqing Yao, Chadds Ford, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/239,051

(22) Filed: Jan. 3, 2019

(65) Prior Publication Data

US 2019/0241560 A1    Aug. 8, 2019

Related U.S. Application Data

(63) Continuation of application No. 15/874,299, filed on Jan. 18, 2018, now Pat. No. 10,214,528, which is a continuation of application No. 15/047,876, filed on Feb. 19, 2016, now Pat. No. 9,890,156.

(60) Provisional application No. 62/192,661, filed on Jul. 15, 2015, provisional application No. 62/118,699, filed on Feb. 20, 2015.

(51) Int. Cl.
C07D 471/04     (2006.01)

(52) U.S. Cl.
CPC .................................. *C07D 471/04* (2013.01)

(58) Field of Classification Search
None
See application file for complete search history.

(56) References Cited

U.S. PATENT DOCUMENTS

| | | |
|---|---|---|
| 850,370 A | 4/1907 | Hynes |
| 3,894,021 A | 7/1975 | Denzel et al. |
| 4,271,074 A | 6/1981 | Lohmann et al. |
| 4,339,267 A | 7/1982 | Levitt |
| 4,347,348 A | 8/1982 | Chernikhov et al. |
| 4,402,878 A | 9/1983 | D'Alelio et al. |
| 4,405,519 A | 9/1983 | D'Alelio et al. |
| 4,405,520 A | 9/1983 | D'Alelio et al. |
| 4,405,786 A | 9/1983 | D'Alelio et al. |
| 4,460,773 A | 7/1984 | Suzuki et al. |
| 4,874,803 A | 10/1989 | Baron et al. |
| 4,940,705 A | 7/1990 | Boshagen et al. |
| 5,159,054 A | 10/1992 | Keller |
| 5,240,941 A | 8/1993 | Bruneau |
| 5,480,887 A | 1/1996 | Hornback et al. |
| 5,536,725 A | 7/1996 | Cullen et al. |
| 5,541,324 A | 7/1996 | TenBrink et al. |
| 5,783,577 A | 7/1998 | Houghten et al. |
| 5,845,025 A | 12/1998 | Garito et al. |
| 5,994,364 A | 11/1999 | Njoroge et al. |
| 6,465,484 B1 | 10/2002 | Bilodeau et al. |
| 6,998,408 B2 | 2/2006 | Pinto |
| 7,074,801 B1 | 7/2006 | Yoshida et al. |
| 7,125,880 B1 | 10/2006 | Chen |
| 7,618,975 B2 | 11/2009 | Cai et al. |
| 7,642,255 B2 | 1/2010 | Sim |
| 8,754,114 B2 | 6/2014 | Yao et al. |
| 8,889,711 B2 | 11/2014 | Bedjeguelal |
| 9,266,892 B2 | 2/2016 | Zhuo et al. |
| 9,388,185 B2 | 7/2016 | Lu et al. |
| 9,533,954 B2 | 1/2017 | Yao et al. |
| 9,533,984 B2 | 1/2017 | Sun et al. |
| 9,580,423 B2 | 2/2017 | Lu et al. |
| 9,611,267 B2 | 4/2017 | Wu et al. |
| 9,708,318 B2 | 7/2017 | Lu et al. |
| 9,745,311 B2 | 8/2017 | Lu et al. |
| 9,801,889 B2 | 10/2017 | Lu et al. |
| 9,890,156 B2 | 2/2018 | Lu et al. |
| 10,016,348 B2 | 7/2018 | Lu et al. |
| 10,040,790 B2 | 8/2018 | Sun et al. |
| 10,131,667 B2 | 11/2018 | Wu et al. |
| 10,213,427 B2 | 2/2019 | Yao et al. |
| 10,214,528 B2 | 2/2019 | Lu et al. |
| 10,251,892 B2 | 4/2019 | Sokolsky et al. |
| 10,450,313 B2 | 10/2019 | Lu et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Turkington et al. "Fibroblast Growth Factor Receptor 4 (FGFR4): A Targetable Regulator of Drug Resistance in Colorectal Cancer". Cell Death and Disease. 2014; 5:e1046. (Year: 2014).*
Tang et al. "Role of Fibroblast Growth Factor 4 in Cancer". Cancer Science, 2018; 109:3024-3031. (Year: 2018).*
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.

(Continued)

*Primary Examiner* — Leslie A. Royds Draper
(74) *Attorney, Agent, or Firm* — Fish & Richardson P.C.

(57) ABSTRACT

The present invention relates to bicyclic heterocycles, and pharmaceutical compositions of the same, that are inhibitors of the FGFR4 enzyme and are useful in the treatment of FGFR4-associated diseases such as cancer.

21 Claims, No Drawings

Specification includes a Sequence Listing.

(56) References Cited

U.S. PATENT DOCUMENTS

| | | |
|---|---|---|
| 2004/0067948 A1 | 4/2004 | Hallett |
| 2004/0097493 A1 | 5/2004 | Chen et al. |
| 2004/0122029 A1 | 6/2004 | Liu et al. |
| 2004/0204427 A1 | 10/2004 | Chen et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0280943 A1 | 12/2007 | Friedman et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0159604 A1 | 6/2011 | Fan et al. |
| 2011/0160203 A1 | 6/2011 | Liu et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0244672 A1 | 8/2018 | Lu et al. |
| 2019/0055237 A1 | 2/2019 | Pan et al. |
| 2019/0062327 A1 | 2/2019 | Sun et al. |
| 2019/0092767 A1 | 3/2019 | Li et al. |
| 2019/0127376 A1 | 5/2019 | Wu et al. |
| 2019/0240220 A1 | 8/2019 | Yao et al. |
| 2019/0269693 A1 | 9/2019 | Lu et al. |
| 2019/0284187 A1 | 9/2019 | Wu et al. |
| 2019/0337948 A1 | 11/2019 | Frietze et al. |

FOREIGN PATENT DOCUMENTS

| | | |
|---|---|---|
| CL | 2017000654 | 12/2017 |
| CL | 2018000089 | 5/2018 |
| CL | 2018000124 | 5/2018 |
| CL | 201702117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 102399220 | 4/2012 |
| CN | 102399233 | 4/2012 |
| CN | 103571502 | 2/2014 |
| CN | 103588771 | 2/2014 |
| CN | 104262330 | 1/2015 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001/035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |

(56) References Cited

FOREIGN PATENT DOCUMENTS

| | | |
|---|---|---|
| JP | 2005015395 | 1/2005 |
| JP | 2005320288 | 11/2005 |
| JP | 200628027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 20119348 | 1/2011 |
| JP | 201144637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 201349251 | 3/2013 |
| JP | 2013179181 | 9/2013 |
| JP | 2015517376 | 6/2015 |
| JP | 2018507214 | 3/2018 |
| JP | 2018511573 | 4/2018 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/24744 | 5/2000 |
| WO | WO 2000/68186 | 11/2000 |
| WO | WO 2001/02369 | 1/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/037891 | 5/2003 |
| WO | WO 2003/040131 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099818 | 12/2003 |
| WO | WO 2003/101985 | 12/2003 |
| WO | WO 2004/002986 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056822 | 7/2004 |
| WO | WO 2004/056830 | 7/2004 |
| WO | WO 2004/065378 | 8/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |

(56) References Cited

FOREIGN PATENT DOCUMENTS

| | | |
|---|---|---|
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |

(56) References Cited

FOREIGN PATENT DOCUMENTS

| | | |
|---|---|---|
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/015643 | 2/2010 |
| WO | WO 2010/017047 | 2/2010 |
| WO | WO 2010/019210 | 2/2010 |
| WO | WO 2010/019899 | 2/2010 |
| WO | WO 2010/030027 | 3/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |

(56) References Cited

FOREIGN PATENT DOCUMENTS

| | | |
|---|---|---|
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/108992 | 7/2015 |
| WO | WO 2016/064960 | 4/2016 |
| WO | WO 2016/134314 | 8/2016 |
| WO | WO 2019/105886 | 6/2019 |

OTHER PUBLICATIONS

Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.

Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.

Arai et al., "Characterization of the cell or origin and propagation potential of the fibroblast growth factor 9-induced mouse model of lung adenocarcinoma," J. Pathol., Mar. 2015, 235(4): 593-605.

Australian Office Action in Australian Application No. 2013287176, dated Sep. 12, 2017, 4 pages.

Australian Office Action in Australian Application No. 2014253798, dated Jul. 31, 2017, 4 pages.

(56) References Cited

OTHER PUBLICATIONS

Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 66(2):1-19 (1977).
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R)-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.
Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J. Combi Chem., 5, 670 (2003).
Blom et al., Preparative LC-MS Purification: Improved Compound Specific Method Optimization, J. Combi. Chem. 2004, 6(6), 874-883.
Blom, K., "Two-Pump at Column Dilution Configuration for Preparative LC-MS", J. Combi Chem., 4, 295 (2002).
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Brooks et al., "Fibroblast growth factor signaling: a new therapeutic opportunity in cancer," Clinical Cancer Research, 2012, 1-23.
Cancer [online], [retrieved on Jul. 6, 2007] Retrieved from the Internet, URL: http://www.nlm.nih.gov/medlineplus/cancer.html.
Cappellen et al., "Frequent activating mutations of FGFR3 in human bladder and cervix carcinomas," Nature Genetics, Sep. 1999, 23: 18-20.
Capelletti et al., "Identification of Recurrent FGFR3-TACC3 Fusion Oncogenes from Lung Adenocarcinoma," AACR Journals, 2014, 6551-6558.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies." Oncogene, 2005, 24: 8259-8267.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 2015-003089, dated Apr. 24, 2017, 13 pages (English Summary).
Chilean Office Action in Chilean Application No. 3355-2014, dated Jan. 18, 2017, 17 pages (with English translation).
Chilean Opposition in Chilean Application No. 3355-2014, received Feb. 3, 2017, 3 pages (English translation only).
Chilean Office Action in Chilean Application No. 2015-003089, dated Jan. 23, 2018, 8 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Cole et al., "Inhibition of FGFR2 and FGFR1 increases cisplatin sensitivity in ovarian cancer," Cancer Biol. Therapy, Sep. 1, 2010, 10(5):495-504.

(56) References Cited

OTHER PUBLICATIONS

Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Aug. 29, 2017, 2 pages.
Colombian Office Action in Colombian Application No. NC2017/0008795, dated Nov. 29, 2018, 8 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Corre et al., "Synthesis and biological evaluation of a triazole-based library of pyrido [2,3-d]pyrimidines as FGFR3 tyrosine kinase inhibitors," Organic & Biomolecular Chemistry, 2010, 8:2164-2173.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors," Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Dovedi and Davies, "Emerging targeted therapies for bladder cancer: a disease waiting for a drug," Cancer Metastasis Rev, 2009, 28:355-367.
Dring et al., "A Global Expression-based Analysis of the Consequences of the t(4;14) Translocation in Myeloma," Clinical Cancer Research, Sep. 2004, 10: 5692-5701.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.

Eurasian Office Aciton in Eurasian Application No. 201590005, dated Oct. 21, 2015, 6 pages.
European Communication pursuant to Article 94(3) EPC in European Application No. 13783125.1, dated Jan. 26, 2016, 4 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Faul et al., "FGF23 induces left ventricular hypertrophy," The Journal of Clinical Investigation, 2010, 1-16.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cel lung cancer cells: therapeutic implications and synergism with epidermal growth factor receptor inhibition," Mol Cancer Therapy, 2008, 3408-3419.
French et al., "Targeting FGFR4 Inhibits Hepatocellular Carcinoma in Preclinical Mouse Models," PLoS ONE, 2012, 7(5):e36713, 1-12.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fukumoto and Yamashita, "FGF23 is a hormone-regulating phophate metabolism—Unique biological characteristics of FGF23," Bone, 2007, 1190-1195.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b]Thieno(Pyridines, Quinolines, Oxazines and Pyrimidines) as possible radioprotective and Antineoplastic agents," Phosphorus, Sulfur and Silicon, Jan. 1998, 134/135:57-76.
Gibson, "Pharmaceutical Preformulation and Formulation," CRC Press LLC, 2009, 2nd ed.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring," Science, 1999, 286: 531-537.
Gomez-Rivera et al., "The Tyrosine Kinase Inhibitor, AZD2171, Inhibits Vascular Endothelial Growth Factor Receptor Signaling and

(56) References Cited

OTHER PUBLICATIONS

Growth of Anaplastic Thyroid Cancer in an Orthotopic Nude Mouse Model," Clin Cancer Res, Aug. 2007, 4519-4527.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999).
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxyphenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Hackam, et al. JAMA, 296(14), 2006, 1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discover, Apr. 2015, 1-14.
Hara and Saito, "CARD9 versus CARMA1 in innate and adaptive immunity," Cell Press, 2009, 234-242.
Heinzle et al., "Is fibroblast growth factor receptor 4 a suitable target of cancer therapy?," Cur. Pharm. Des. 2014, 20:2881-98.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 259-267.
Hideshima and Anderson, "Preclinical Studies of Novel Targeted Therapies," Hematol Oncol Clin N Am, 2007, 1071-1091.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Huynh, "Tyrosine kinase inhibitors to treat liver cancer," Expert Opinion, 2010, 13-26.

Hynes and Dey, "Potential for Targeting the Fibroblast Growth Factor Receptors in Breast Cancer," Cancer Res, 2010, 70:5199-5202.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Inokuchi et al., "Therapeutic targeting of fibroblast growth factor receptors in gastric cancer," Gastroenterol Res Pract., Apr. 27, 2015, 2015:796380, 8 pages.
International Preliminary Report on Patentability and Written Opinion in International Application No. PCT/US2011/066473, dated Jun. 25, 2013, 10 pages.
International Preliminary Report on Patentability in International Application No PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report dated Jun. 19, 2012 for International Appln. No. PCT/US2011/066473 (15 pgs.).

(56) References Cited

OTHER PUBLICATIONS

International Search Report and Written Opinion in International Application No. PCT/US2018/034559, dated Mar. 8, 2019, 14 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Jebar et al., "FGFR3 and Ras gene mutations are mutually exclusive genetic events in urothelial cell carcinoma," Oncogene, 2005, 24: 5218-5225.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jiang et al., "miR-99a promotes proliferation targeting FGFR3 in human epithelial ovarian cancer cells," Biomedicine & Pharmacotherapy, 2014, 68: 163-169.
Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, V.C. Nature Reviews: Drug Discovery, 2, 2003, 205.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known $P2X_1$ receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.

Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS ONE, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2-Amplified Gastric Cancer Cell Lines Require FGFR2 and Erbb3 Signaling for Growth and Survival," Cancer Res., Apr. 1, 2008, 68(7):2340-2348.
Kunii et al., "FGFR2-Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR-dependent urothelial carcinoma growth in vitro and in vivo," Br. J Cancer, 2010, 1-8.
Lamont et al., "Small molecule FGF receptor inhibitors block FGFR-dependent urothelial carcinoma growth in vitro and in vivo," Br. J Cancer, 2011, 104:75-82.
Le Corre et al., "Synthesis and biological evaluation of a triazole-based library of pyrido [2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.

(56) References Cited

OTHER PUBLICATIONS

Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.
Maeda et al., "Transforming property of TEL-FGFR3 mediated through PI3-K in a T-cell lymphoma that subsequently progressed to AML," BLOOD, Mar. 2005, 105(5): 2115-2123.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Made and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martino et al., "Mutant fibroblast growth factor receptor 3 induces intracellular signaling and cellular transformation in a cell type- and mutation-specific manner," Oncogene, 2009, 28: 4306-4316.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain," The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.

Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
New Zealand Office Action in New Zealand Application No. 743274, dated Jul. 19, 2018, 5 pages.
New Zealand Examination Report in New Zealand Application No. 743274, dated Jul. 18, 2018, 4 pages.
New Zealand Office Action in New Zealand Application No. 702747, dated Sep. 16, 2016, 3 pages.
New Zealand Office Action in New Zealand Application No. 702747, dated Mar. 8, 2019, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.

(56) References Cited

OTHER PUBLICATIONS

Propper et al., "Phase I and Pharmacokinetic Study of PKC412, an Inhibitor of Protein Kinase C," J Clin Oncol, 2001, 19(5):1485-1492.

Qian et al., "Targeting Tumor Angiogenesis with Histone Deacetylase Inhibitors: the Hydroxamic Acid Derivative LBH589," Clin Cancer Res, Jan. 2006, 634-642.

Qing et al., "Antibody-based targeting of FGFR3 in bladder carcinoma and t(4;14)-positive multiple myeloma in mice," The Journal of Clinical Investigation, May 2009, 119(5): 1216-1229.

Qing et al., "Antibody-based targeting of FGFR3 in bladder carcinoma and t(4;14)-positive multiple myeloma in mice," The Journal of Clinical Investigation, May 2009, Supplemental Table 1: Summary of crystallographic analysis, 21 pages.

Qiu et al., "Over-expression of fibroblast growth factor receptor 3 in human hepatocellular carcinoma," World J Gastroenterol, 2005, 11(34): 5266-5272.

Raab et al., "Multiple myeloma," Lancet, 2009, 374: 324-339.

Ravindranathan et al., "Discovery of Novel Fibroblast Growth Factor Receptor 1 Kinase Inhibitors by Structure-Based Virtual Screening," J. Med. Chem., 2010, 53: 1662-1672.

Razzaque, "FGF23-mediated regulation of systemic phosphate homeostasis: is Klotho an essential player?," Am J Physiol Renal Physiol, 2009, 470-476.

Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.

Reis-Filho et al., "FGFR1 Emerges as a Potential Therapeutic Target for Lobular Breast Carcinomas," Clin Cancer Res, Nov. 2006, 6652-6662.

Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.

Remington's Pharmaceutical Sciences, 17th ed., Mack Publishing Company, Easton, Pa., 1985, p. 1418.

Remington, "The Science and Practice of Pharmacy," Lippincott Williams & Wilkins, 2005, 21st edition.

Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.

Ribatti et al., "The discovery of basic fibroblast growth factor/fibroblast growth factor-2 and its role in haematological malignancies," Cytokine & Growth Factor Reviews, 2007, 18: 327-334.

Ribatti, "Tyrosine Kinase Inhibitors as Antiangiogenic Drugs in Multiple Myeloma," Pharmaceuticals, 2010, 3: 1225-1231.

Roidl et al., "Resistance to Chemotherapy Is Associated with Fibroblast Growth Factor Receptor 4 Up-Regulation," Clin Cancer Res, Mar. 2009, 2058-2066.

Ronchetti et al., "Deregulated FGFR3 mutants in multiple myeloma cell lines with t(4;14): comparative analysis of Y373C, K650E and the novel G384D mutations," Oncogene, 2001, 20: 3553-3562.

Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.

Rowe et al., "Handbook of Pharmaceutical Excipients," The Pharmaceutical Press and the American Pharmaceutical Association, 2009, 6th Edition, Front Matter Only, 8 pages.

Ryan et al., "Toxicologic Pathology of Unique Biotechnology Agents and Biotherapies," Toxicologic Pathology, 1999, 27(1): 78-86.

Sakurai et al., "A novel angiogenesis inhibitor, Ki23057, is useful for preventing the progression of colon cancer and the spreading of cancer cells to the liver," European Journal of Cancer, 2007, 2612-2620.

Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.

Saxty et al., "Fragment-based drug discovery of selective inhibitors of fibroblast growth factor receptor (FGFr)," Cancer Res, Apr. 15, 2010, 70, 5778.

Schenone et al., "Small Molecules ATP-Comptetitive Inhibitors of FLT3: A Chemical Overview," Current Medicinal Chemistry, 2008, 15(29): 3113-3132.

Schlapbach et al., "A novel Pd-catalyzed cyclization rection of ureas for the synthesis of dihydroquinazolinone p38 kinase inhibitors," Bioorg. Med. Chem. Lett., 2004, 357-360.

Science IP Order 3032627, Chemical Structure Search, Science IP, Apr. 2012, 78 pages.

Science IP Order 3101926, Chemical Structure Search, Science IP, Jan. 2015, 50 pages.

Science IP Order 3101983, Chemical Structure Search, Science IP, Jan. 2015, 70 pages.

Science IP Order 3104564, Patent Chemical Structure Search, Science IP, Mar. 2015, 90 pages.

Science IP Order 3104565, Patent Chemical Structure Search, Science IP, Mar. 2015, 521 pages.

Segev et al., "Restrained chondrocyte proliferation and maturation with abnormal growth plate vascularization and ossification in human FRFR-3$^{G380R}$ trasngenic mice," Human Molecular Genetics, 2000, 9(2): 249-258.

Shariat et al., "Association of Angiogenesis Related Markers With Bladder Cancer Outcomes and Other Molecular Markers," The Journal of Urology, May 2010, 183: 1744-1750.

Sharkey et al., "PKC412 demonstrates JNK-dependent activity against human multiple myeloma cells," Blood, Feb. 2007, 109(4): 1712-1719.

Shinya et al., "Fgf signalling through MAPK cascade is required for development of the subpallial telencephalon in zebrafish embryos," Development, 2001, 4153-4164.

Singh et al., "Transforming Fusions of FGFR and TACC Genes in Human Glioblastoma," Science, Sep. 2012, 337:1231-1235.

Slavin et al., "Familial Tumoral Calcinosis," The American Journal of Surgican Pathology, 1993, 17(8): 188-802.

Smith et al., "Circulating αKlotho influences phosphate handling by controlling FGF23 production," The Journal of Clinical Investigation, Dec. 2012, 122(12): 4710-4715.

Song et al., "Fibroblast growth factors: An epigenetic mechanism of broad spectrum resistance to anticancer drugs," PNAS, Jul. 2000, 97(15): 8658-8663.

Sonvilla et al., "Fibroblast growth factor receptor 3-IIIc mediates colorectal cancer growth and migration," British Journal of Cancer, 2010, 1-12.

Soria, "FGFR inhibition overview of clinical development programs," Presentation, presented at TAT in Washington DC on Mar. 5-7, 2014, 54 pages.

Soverini et al., "Novel mutation and RNA splice variant of fibroblast growth factor receptor 3 in multiple myeloma patients at diagnosis," Haematologica, 2002, 87: 1036-1040.

Specktor et al., "Hyperphosphatemic familial tumoral calcinosis caused by a mutation in GALNT3 in a European kindred," J Hum Genet, 2006, 51:487-490.

Squires et al., "Development of inhibitors of the fibroblast growth factor receptor (FGFR) kinase using a fragment based approach," Cancer Res 70, Apr. 15, 2010, 3626.

Squires et al., "Development of inhibitors of the fibroblast growth factor receptor (FGFR) kinase using a fragment based approach," Cancer Res, 2008, 1 page.

Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.

Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (F1k-1/KDR), FGF-R1, and PDGF-Rβ Tyrosine Kinases," J. Med. Chem., 2000, 43: 2655-2663.

Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.

(56) References Cited

OTHER PUBLICATIONS

Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Tan et al., "Development of covalent inhibitors that can overcome resistance to first-generation FGFR kinase inhibitors," PNAS, Oct. 2014, E4869-E4877.
Taylor et al., "Identification of FGFR4-activating mutations in human rhabdomyasarcomas that promote metastasis in xenotransplanted models," J Clin Invest, Nov. 2009, 119(11): 3395-407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
Thome and Weil, "Post-translational modifications regulate distinct functions of CARMA1 and BCL10," TRENDS in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.
Trudel et al., "CHIR-258, a novel, multitargeted tyrosine kinase inhibitor for the potential treatment of t(4;14) multiple myeloma," Blood, Apr. 2005, 105(7): 2941-2948.
Trudel et al., "Inhibition of fibroblast growth factor receptor 3 induces differentiation and apoptosis in t(4;14) myeloma," Blood, May 2004, 103(9):3521-3528.
Trudel et al., "The inhibitory anti-FGFR3 antibody, PRO-001, is cytotoxic to t(4;14) multiple myeloma cells," Blood, May 2006, 107(10): 4039-4046.
Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.
Turner and Grose, "Fibroblast growth factor signalling: from development to cancer," Nature Reviews Cancer, 2010, 10:116-129.
Turner et al., "FGFR1 Amplification Drives Endocrine Therapy Resistance and Is a Therapeutic Target in Breast Cancer," Cancer Res., Mar. 2010, 2085-2094.
Tvorogov et al., "Effective Suppression of Vascular Network Formation by Combination of Antibodies Blocking VEGFR Ligand Binding and Receptor Dimerization," Cancer Cell, Dec. 2010, 18: 630-640.
Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.
Ukraine Office Action in Ukraine Application No. a201500191, dated Dec. 13, 2016, 10 pages (with English translation).
Ukraine Office Action in Ukraine Application No. a201511370, dated Nov. 12, 2018, 6 pages (with English translation).
Urakawa et al., "Klotho converts canonical FGF receptor into a specific receptor for FGF23," Nature, Dec. 2006, 444: 770-774.
Uzawa et al., "Targeting fibroblast growth factor receptor 3 enhances radiosensitivity in human squamous cancer cells," Oncogene, 2011, 1-6.
Van Oers et al., "FGFR3 Mutations Indicate Better Survival in Invasive Upper Urinary Tract and Bladder Tumours," European Urology, 2009, 650-658.
Våtsveen et al., "FGFR3 is expressed and is important for survival in INA-6, a human myeloma cell line without a t(4;14)," Eur. J. Haematol., 83:5, Jul. 6, 2009, 471-476.
Vietnamese Office Action in Vietnamese Application No. 1-2015-00102, dated Mar. 18, 2015, 4 pages.
Von Massenhausen et al., "Evaluation of FGFR3 as a Therapeutic Target in Head and Neck Squamous Cell Carcinoma," Targ. Oncol., 2016, 11: 631-642.
Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.
Wang and Ding, "Fibroblast growth factor receptors in breast cancer," Tumor Biology, May 2017, 1-10.
Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.
Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.
Wu, "Urothelial Tumorigenesis: A Tale of Divergent Pathways," Nature Reviews, Sep. 2005, 5: 713-725.
Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.
Wöhrle et al., "Pharmacological inhibition of FGFR signaling ameliorates FGF23-mediated hypophosphatemic rickets," Journal of Bone and Mineral Research, 2012, 1-36.
Xian et al., "Pleiotropic effects of FGFR1 on cell proliferation, survival, and migration in a 3D mammary epithelial cell model," JCB, 2005, 171(4): 663-673.
Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.
Xu et al., "Fibroblast growth factor receptor 4 promotes progression and correlates to poor prognosis in cholangiocarcinoma," Biochemical and Biophysical Research Communications, 2014, 446: 54-60.
Yu et al., "Analysis of the Biochemical Mechanisms for the Endocrine Actions of Fibroblast Growth Factor-23," Endocrinology, Nov. 2005, 146(11): 4647-4656.

(56) References Cited

OTHER PUBLICATIONS

Zhang et al., "AZD4547, a potent and selective FGF-receptor inhibitor induces tumor regressions in a human primary model of FGF-receptor 2 amplified gastric cancer and is efficacious in combination with chemotherapy," 2012.
Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.
Zhang et al., "FP-1039 (FGFR1:Fc), A Soluble FGFR1 Receptor Antagonist, Inhibits Tumor Growth and Angiogenesis," Mol Cancer Ther, Nov. 7, 2007, B55.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Malaysian Office Action in Malaysian Application No. 2014003396, dated Dec. 15, 2017, 4 pages.
Mexican Office Action in Mexican Application No. MX/a/2014/015192, dated Jan. 24, 2018, 6 pages.
Japanese Office Action in Japanese Application No. 2016-509131, dated Feb. 20, 2018, 5 pages (English Translation).
Eurasian Office Action in Eurasian Application No. 201791866, dated Feburary 19, 2018, 10 pages (English Translation).
Eurasian Office Action in Eurasian Application No. 201590005, dated Mar. 28, 2018.
Taiwan Office Action in Taiwan Application No. 103114284, dated Apr. 9, 2018, 4 pages (English Search Report).
Chinese Office Action in Chinese Application No. 201480028858.7, dated Apr. 4, 2018, 10 pages (English Translation).
Eurasian Office Action in Eurasian Application No. 201791867, dated Apr. 4, 2018, 4 pages (English Translation).
Indonesian Office Action in Indonesian Application No. P00201507153, dated Apr. 27, 2018, 5 pages (English Translation).
Williams et al., "Oncogenic FGFR3 gene fusions in bladder cancer," Hum Mol Genet, 2013, 22:795-803.
The Cancer Genome Atlas Research Network, "Comprehensivemolecular characterization of urothelial bladder carcinoma," Nature, 2014, 507: 315-22.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Zhang et al., "Enhanced FGFR signalling predisposes pancreatic cancer to the effect of a potent FGFR inhibitor in preclinical models," British Journal of Cancer, 2014, 110: 320-329.
Peruvian Office Action in Peruvian Application No. 2433, dated Nov. 27, 2018, 13 pages.
Chinese Office Action in Chinese Application No. 201710874686.0, dated Feb. 25, 2019, 17 pages.
Chinese Office Action in Chinese Application No. 201710395346.X, dated Jan. 22, 2019, 17 pages.
Indian Office Action in Indian Application No. 9781/DELNP/2015, dated Jan. 18, 2019, 6 pages.
Australian Office Action in Australian Application No. 2018208772, dated Jul. 1, 2018, 5 pages.
Australian Office Action in Australian Application No. 2016219822, dated Jul. 8, 2019, 4 pages.
Chen et al., "Genome-Wide Loss of Heterozygosity and DNA Copy Number Aberration in HPV-Negative Oral Squamous Cell Carcinoma and Their Associations with Disease-Specific Survival," PLOS ONE, Aug. 2015, 23 pages.
Chilean Office Action in Chilean Application No. 2122-2017, dated Apr. 22, 2019, 25 pages.
Costa Rican Office Action in Costa Rican Application No. 2014-0577, dated Jun. 13, 2019, 17 pages.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Desnoyers et al., "Targeting FGF19 inhibits tumor growth in colon cancer xenograft and FGF19 transgenic hepatocellular carcinoma models," Oncogene, 2008, 27:85-97.
Ding et al., "Somatic mutations affect key pathways in lung adenocarcinoma," Nature., Oct. 23, 2008, 455:1069-1075.
French et al., Targeting FGFR4 inhibits hepatocellular carcinoma in preclinical mouse models, PLoS One 2012;7:e36713.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Helsten et al., "The FGFR Landscape in Cancer: Analysis of 4,853 Tumors by Next-Generation Sequencing," Clin. Cancer Res., Jan. 2016, 22:259-267.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
ICH Harmonised Tripartite Guideline, "Specifications:Test Procedures and Acceptance Criteria for New Drug Substances and New Drug Products Chemical Substances," ICHTRRPHU, Oct. 6, 1999, 35 pages.
Marks et al., "Mutational Analysis of EGFR and Related Signaling Pathway Genes in Lung Adenocarcinomas Identifies a Novel Somatic Kinase Domain Mutation in FGFR4," PLoS ONE, May 9, 2007, 2:e426.
Philippine Office Action in Philippine Application No. 1/2015/502383, dated Jul. 8, 2019, 7 pages.
Seitzer et al., "A single nucleotide change in the mouse genome accelerates breast cancer progression," Cancer Res., Jan. 2010, 70(2):802-812.
Shi et al., "High Expression of FGFR4 Enhances Tumor Growth and Metastasis in Nasopharyngeal Carcinoma," Journal of Cancer, 2015, 6(12): 1245-1254.
Taylor et al., "Identification of FGFR4-activating mutations in human rhabdomyasarcomas that promote metastasis in xenotransplanted models," J Clin Invest., Nov. 2009, 119(11):3395-3407.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Wang et al., "The fibroblast growth factor receptor-4 Arg388 allele is associated with prostate cancer initiation and progression," Clin Cancer Res. 2004, 10:6169-6178.
Yu et al., "FGFR-4 Arg(3)(8)(8) enhances prostate cancer progression via extracellular signal-related kinase and serum response factor signaling," Clin Cancer Res., Jul. 2011, 17:4355-4366.

(56) References Cited

OTHER PUBLICATIONS

Ying et al., "Genome-wide screening for genetic alterations in esophageal cancer by aCGH identifies 11q13 amplification oncogenes associated with nodal metastasis," PLoS One, Jun. 25, 2012, 7:e39797.
Zaid et al., "Identification of FGFR4 as a Potential Therapeutic Target for Advanced-Stage, High-Grade Serous Ovarian Cancer," Clin Cancer Res, 2013, 19(4): 809-820.
Australian Office Action in Australian Application No. 2016219816, dated Aug. 26, 2019, 3 pages.
Australian Office Action in Australian Application No. 2019200066, dated Aug. 27, 2019, 6 pages.
Caira, "Crystalline Polymorphism of Organic Compounds," Topics in Current Chemistry, Jan. 1, 1998, 198:163-208.
Chilean Office Action in Chilean Application No. 1984-2017, dated Sep. 12, 2019, 9 pages.
Chinese Office Action in Chinese Application No. 201710395346. X, dated Sep. 9, 2019, 10 pages.
Chinese Office Action in Chinese Application No. 201680011348.8, dated Aug. 2, 2019, 14 pages.
Chinese Office Action in Chinese Application No. 201680011332.7, dated Aug. 5, 2019, 14 pages.
Chinese Office Action in Chinese Application No. 10874686.0, dated Oct. 8, 2019, 10 pages.
Colombian Office Action in Colombian Application No. NC2017/0008795, dated Aug. 16, 2019, 6 pages.
Heinzle et al., "Is Fibroblast growth factor receptor 4 a suitable target of cancer therapy?" Cur. Pharm. Des., May 1, 2014, 20:2881-2898.
Indian Office Action in Indian Application No. 201717030267, dated Dec. 3, 2019, 7 pages.
International Preliminary Report on Patentability in International Application No. PCT/US2018/034559, dated Nov. 26, 2019, 8 pages.
International Invitation to Pay Fees in International Appln. No. PCT/US2019/030633, dated Aug. 12, 2019, 5 pages.
Jackson et al., "8p11 Myeloproliferative syndrome: a review," Human Pathology, Apr. 1, 2010, 41:461-476.
Japanese Office Action in Japanese Application No. 2018-228352, dated Aug. 20, 2019, 6 pages.
Japanese Office Action in Japanese Application No. 2017-544021, dated Nov. 26, 2019, 6 pages.
Korean Office Action in Korean Application No. 10-2015-7000701, dated Aug. 26, 2019, 19 pages.
Philippine Office Action in Philippine Application No. 1-2017-501481, dated Oct. 29, 2019, 4 pages.
Taiwan Office Action in Taiwan Application No. 105105018, dated Oct. 22, 2019, 7 pages.
Takii et al., "Serotonin Derivative, N-(p-Coumaroyl)serotonin, Isolated from Safflower (Carthamus tinctorius L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Wuts et al., "Greene's Protective Groups in Organic Synthesis," 4th Ed., 2006, Chapter 7, 696-926.
Argentina Office Action in Argentina Application No. 20140101651, dated Nov. 21, 2019, 5 pages.
Ash and Ash, "Handbook of Pharmaceutical Additives," Gower Publishing Company, 2007, 3rd ed, Title Page only, 1 page.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Chilean Office Action in Chilean Application No. 2122-2017, dated Nov. 15, 2019, 15 pages.
Colombian Office Action in Colombian Application No. NC2019/0009690, dated Jan. 22, 2020, 20 pages.
Edmondson et al., "Aminopiperidine-fused imidazoles as dipeptidyl peptidase-IV inhibitors," Bioorg & Med Chem Lett., 2009, 19(15):4097-4101.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Heinrich et al., "Fragment-based discovery of new highly substituted 1H-pyrrolo[2,3-b]—and 3H-imidazolo[4,5-b]-pyridines as focal adhesion kinase inhibitors," J of Med Chem., Jan. 8, 2013, 56(3):1160-1170.
Indian Office Action in Indian Application No. 201717030265, dated Dec. 12, 2019, 5 pages.
International Search Report and Written Opinion in International Application No. PCT/US2019/030633, dated Nov. 28, 2019, 21 pages.
Philippine Office Action in Philippine Application No. 1/2017/501483, dated Dec. 12, 2019, 5 pages.
STN Search Report dated Jan. 6, 2020, 88 pages.
Taiwan Office Action in Taiwan Application No. 107146498, dated Dec. 19, 2019, 7 pages.
Taiwan Office Action in Taiwan Application No. 105104993, dated Feb. 11, 2020, 9 pages.
Ukraine Office Action in Ukraine Application No. a201709220, dated Dec. 9, 2019, 11 pages.

* cited by examiner

```
SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15
```

BICYCLIC HETEROCYCLES AS FGFR4 INHIBITORS

FIELD OF THE INVENTION

The present disclosure relates to bicyclic heterocycles, and pharmaceutical compositions of the same, that are inhibitors of the enzyme FGFR4 and are useful in the treatment of FGFR4-associated diseases such as cancer.

BACKGROUND OF INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes.

The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395). Targeting FGFR4 with selective small molecule inhibitors may therefore prove beneficial in the treatment of certain cancers.

There is a continuing need for the development of new drugs for the treatment of cancer and other diseases, and the FGFR4 inhibitors described herein help address this need.

SUMMARY OF INVENTION

The present disclosure is directed to inhibitors of FGFR4 having Formula (I):

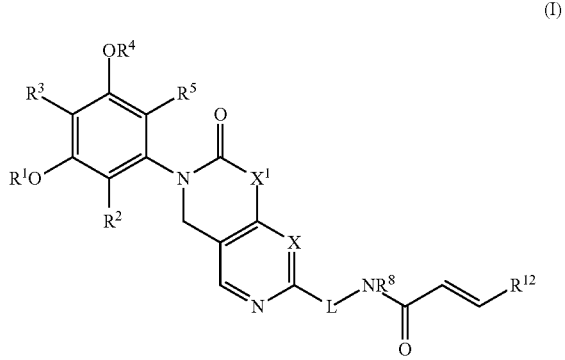

or pharmaceutically acceptable salts thereof, wherein constituent variables are defined herein.

The present disclosure is further directed to pharmaceutical compositions comprising a compound of Formula (I), or a pharmaceutically acceptable salt thereof, and at least one pharmaceutically acceptable carrier.

The present disclosure is further directed to methods of inhibiting an FGFR4 enzyme comprising contacting the enzyme with a compound of Formula (I), or a pharmaceutically acceptable salt thereof.

The present disclosure is further directed to a method of treating a disease associated with abnormal activity or expression of an FGFR4 enzyme, comprising administering a compound of Formula (I), or a pharmaceutically acceptable salt thereof, to a patient in need thereof.

The present disclosure is further directed to compounds of Formula (I) for use in treating a disease associated with abnormal activity or expression of an FGFR4 enzyme.

The present disclosure is further directed to a method for treating a disorder mediated by an FGFR4 enzyme, or a mutant thereof, in a patient in need thereof, comprising the step of administering to said patient a compound according to the present invention or pharmaceutically acceptable composition thereof.

The present disclosure is further directed to a method for treating a disorder mediated by an FGFR4 enzyme, or a mutant thereof, in a patient in need thereof, comprising the step of administering to the patient a compound according to the present invention or a pharmaceutically acceptable salt thereof, or a composition comprising a compound according to the present invention, in combination with another therapy or therapeutic agent as described herein.

The present disclosure is further directed to the use of compounds of Formula (I) in the preparation of a medicament for use in therapy.

DETAILED DESCRIPTION

Compounds

In one aspect, the present disclosure provides compounds of Formula (I):

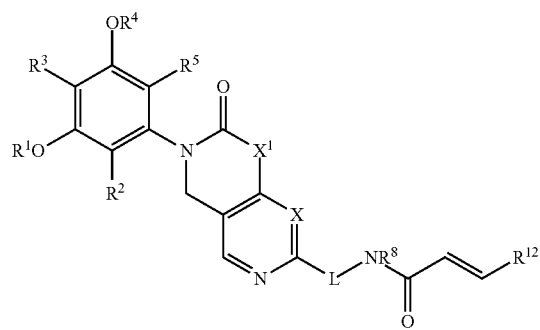

or pharmaceutically acceptable salts thereof, wherein:

$X^1$ is $CR^{10}R^{11}$ or $NR^7$;

X is N or $CR^6$;

$R^1$ is $C_{1-3}$ alkyl or $C_{1-3}$ haloalkyl;

$R^2$ is H, halo, $C_{1-3}$ alkyl, $C_{1-3}$ haloalkyl, CN, or $C_{1-3}$ alkoxy;

$R^3$ is H, halo, $C_{1-3}$ alkyl, $C_{1-3}$ haloalkyl, CN, or $C_{1-3}$ alkoxy;

$R^4$ is $C_{1-3}$ alkyl or $C_{1-3}$ haloalkyl;

$R^5$ is H, halo, $C_{1-3}$ alkyl, $C_{1-3}$ haloalkyl, CN, or $C_{1-3}$ alkoxy;

$R^6$ and $R^7$ are each independently selected from H, halo, CN, $OR^{a4}$, $SR^{a4}$, $C(O)NR^{c4}R^{d4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^6$ and $R^7$ are each optionally substituted with 1, 2, or 3 substituents independently selected from $R^{10A}$;

L is $-(CR^{13}R^{14})_n-$, wherein $R^{13}$ and $R^{14}$ are each independently H, $C_{1-6}$ alkyl, $C_{6-10}$ aryl, 5 to 10 membered heteroaryl or 4 to 7 membered heterocycloalkyl, wherein the $C_{1-6}$ alkyl, $C_{6-10}$ aryl, 5 to 10 membered heteroaryl or 4 to 7-membered heterocycloalkyl is optionally substituted with from 1 to 3 $R^{17}$ groups; or $R^{13}$ and $R^{14}$ are taken together with the carbon atom to which they are attached form a $C_{3-6}$ cycloalkyl or 4 to 6-membered heterocycloalkyl group; wherein the $C_{3-6}$ cycloalkyl or 4 to 6-membered heterocycloalkyl group is optionally substituted with from 1 to 3 $R^{17}$ members; the subscript n is 1, 2 or 3; in some embodiments, the subscript n is 1 or 2.

$R^8$ is H or $C_{1-4}$ alkyl which is optionally substituted by halo, CN, $OR^{a9}$, $C(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S$ (O)$_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, phenyl, $C_{3-7}$ cycloalkyl, a 5-6 membered heteroaryl moiety having carbon and 1, 2, or 3 heteroatoms independently selected from N, O and S, or a 4-7 membered heterocycloalkyl moiety having carbon and 1, 2, or 3 heteroatoms independently selected from N, O and S; wherein said phenyl, $C_{3-7}$ cycloalkyl, 5-6 membered heteroaryl, and 4-7 membered heterocycloalkyl groups of $R^8$ are each optionally substituted with 1 or 2 $R^{19}$;

$R^{10}$ and $R^{11}$ are each independently selected from H, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, a 5-10 membered heteroaryl moiety having carbon and 1, 2, or 3 heteroatoms independently selected from N, O and S, and a 4-10 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl groups of $R^{10}$ and $R^{11}$ are each optionally substituted with 1, 2, 3, or 4 $R^{10A}$;

$R^{10A}$, at each occurrence, is independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C$ (O)$OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl group of $R^{10A}$ are each optionally substituted with 1, 2, or 3 substituents independently selected from $R^{19}$;

$R^{a4}$, $R^{b4}$, $R^{c4}$, and $R^{d4}$, at each occurrence, are independently selected from H, $C_{1-4}$ alkyl, $C_{2-4}$ alkenyl, $C_{2-4}$ alkynyl, $C_{1-4}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-4}$ alkyl, $C_{2-4}$ alkenyl, $C_{2-4}$ alkynyl, phenyl, $C_{3-6}$ cycloalkyl, 5-6 membered heteroaryl, and 4-7 membered heterocycloalkyl group of $R^{a4}$, $R^{b4}$, $R^{c4}$, and $R^{d4}$ are each optionally substituted with 1, 2, or 3 substituents independently selected from $R^{19}$;

alternatively, $R^{c4}$ and $R^{d4}$ together with the nitrogen atom to which they are attached form a 4-, 5-, 6-, or 7-membered heterocycloalkyl group which is optionally substituted with 1, 2 or 3 substituents independently selected from $R^{19}$;

each $R^{e4}$ is independently H or $C_{1-4}$ alkyl;

alternatively, $R^{10}$ and $R^{11}$ together with the carbon atom to which they are attached form a 3-, 4-, 5-, 6-, or 7-membered cycloalkyl group or a 4-, 5-, 6-, 7-, 8-, 9-, or 10-membered heterocycloalkyl group; wherein said 3-, 4-, 5-, 6-, or 7-membered cycloalkyl group and 4-, 5-, 6-, 7-, 8-, 9-, or 10-membered heterocycloalkyl group are each optionally substituted with 1, 2, 3 or 4 $R^{10A}$;

$R^{12}$ is H or $C_{1-4}$ alkyl which is optionally substituted by $R^{17}$;

$R^{17}$, at each occurrence, is independently selected from halo, CN, $NO_2$, $OR^{a7}$, $SR^{a7}$, $C(O)R^{b7}$, $C(O)NR^{c7}R^{d7}$, $C(O)$ $OR^{a7}$, $OC(O)R^{b7}$, $OC(O)NR^{c7}R^{d7}$, $C(=NR^{e7})NR^{c7}R^{d7}$, $NR^{c7}C(=NR^{e7})NR^{c7}R^{d7}$, $NR^{c7}R^{d7}$, $NR^{c7}C(O)R^{b7}$, $NR^{c7}C$ (O)R$^{a7}$, NR$^{c7}$C(O)NR$^{c7}$R$^{d7}$, NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, C$_{1-6}$ alkyl, C$_{2-6}$ alkenyl, C$_{2-6}$ alkynyl, C$_{1-6}$ haloalkyl, phenyl, C$_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-6}$ alkyl, C$_{2-6}$ alkenyl, C$_{2-6}$ alkynyl, phenyl, C$_{3-6}$ cycloalkyl, 5-6 membered heteroaryl, and 4-7 membered heterocycloalkyl groups of R$^{17}$ are each optionally substituted with 1, 2, or 3 substituents independently selected from R$^{19}$;

R$^{a7}$, R$^{b7}$, R$^{c7}$, and R$^{d7}$, at each occurrence, are independently selected from H, C$_{1-4}$ alkyl, C$_{2-4}$ alkenyl, C$_{2-4}$ alkynyl, C$_{1-4}$ haloalkyl, phenyl, C$_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-4}$ alkyl, C$_{2-4}$ alkenyl, C$_{2-4}$ alkynyl, phenyl, C$_{3-6}$ cycloalkyl, 5-6 membered heteroaryl, and 4-7 membered heterocycloalkyl groups of R$^{a7}$, R$^{b7}$, R$^{c7}$, and R$^{d7}$ are each optionally substituted with 1, 2, or 3 substituents independently selected from R$^{19}$;

alternatively, R$^{c7}$ and R$^{d7}$ together with the nitrogen atom to which they are attached form a 4-, 5-, 6-, or 7-membered heterocycloalkyl group which is optionally substituted with 1, 2 or 3 substituents independently selected from R$^{19}$;

R$^{e7}$, at each occurrence, is independently H or C$_{1-4}$ alkyl;

R$^{19}$, at each occurrence, is independently selected from halo, CN, NO$_2$, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, S(O)$_2$NR$^{c9}$R$^{d9}$, C$_{1-4}$ alkyl, C$_{2-4}$ alkenyl, C$_{2-4}$ alkynyl, and C$_{1-4}$ haloalkyl;

R$^{a9}$, R$^{c9}$, and R$^{d9}$, at each occurrence, are independently selected from H and C$_{1-4}$ alkyl; and R$^{b9}$, at each occurrence, is independently C$_{1-4}$ alkyl. In one embodiment, Y is O. In another embodiment, Y is NR$^8$.

In some embodiments of compounds of Formula (I):

X$^1$ is CR$^{10}$R$^{11}$ or NR$^7$;

X is N or CR$^6$;

R$^1$ is C$_{1-3}$ alkyl or C$_{1-3}$ haloalkyl;

R$^2$ is H, halo, C$_{1-3}$ alkyl, C$_{1-3}$ haloalkyl, CN, or C$_{1-3}$ alkoxy;

R$^3$ is H, halo, C$_{1-3}$ alkyl, C$_{1-3}$ haloalkyl, CN, or C$_{1-3}$ alkoxy;

R$^4$ is C$_{1-3}$ alkyl or C$_{1-3}$ haloalkyl;

R$^5$ is H, halo, C$_{1-3}$ alkyl, C$_{1-3}$ haloalkyl, CN, or C$_{1-3}$ alkoxy;

R$^6$ is selected from H, halo, CN, OR$^{a4}$, SR$^{a4}$, C(O)NR$^{c4}$R$^{d4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, C$_{1-6}$ alkyl, C$_{2-6}$ alkenyl, C$_{2-6}$ alkynyl, C$_{1-6}$ haloalkyl, phenyl, C$_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-6}$ alkyl, C$_{2-6}$ alkenyl, C$_{2-6}$ alkynyl, phenyl, C$_{3-6}$ cycloalkyl, 5-6 membered heteroaryl, and 4-7 membered heterocycloalkyl groups of R$^6$ are each optionally substituted with 1, 2, or 3 substituents independently selected from R$^{10A}$;

R$^7$ is selected from H, C(O)NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, C$_{1-6}$ alkyl, C$_{2-6}$ alkenyl, C$_{2-6}$ alkynyl, C$_{1-6}$ haloalkyl, phenyl, C$_{3-6}$ cycloalkyl, a 5-6 membered heteroaryl having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-6}$ alkyl, C$_{2-6}$ alkenyl, C$_{2-6}$ alkynyl, phenyl, C$_{3-6}$ cycloalkyl, 5-6 membered heteroaryl, and 4-7 membered heterocycloalkyl groups of R$^7$ are each optionally substituted with 1, 2, or 3 substituents independently selected from R$^{10A}$;

L is —(CR$^{13}$R$^{14}$)$_n$—, wherein R$^{13}$ and R$^{14}$ are each independently H, C$_{1-6}$ alkyl, C$_{6-10}$ aryl, 5 to 10 membered heteroaryl or 4 to 10 membered heterocycloalkyl, wherein the C$_{1-6}$ alkyl, C$_{6-10}$ aryl, 5 to 10 membered heteroaryl or 4 to 7 membered heterocycloalkyl is optionally substituted with from 1 to 3 R$^{17}$ groups;

the subscript n is 1 or 2;

R$^8$ is H or C$_{1-4}$ alkyl which is optionally substituted by halo, CN, OR$^{a9}$, C(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, S(O)$_2$NR$^{c9}$R$^{d9}$, phenyl, C$_{3-7}$ cycloalkyl, a 5-6 membered heteroaryl moiety having carbon and 1, 2, or 3 heteroatoms independently selected from N, O and S, or a 4-7 membered heterocycloalkyl moiety having carbon and 1, 2, or 3 heteroatoms independently selected from N, O and S; wherein said phenyl, C$_{3-7}$ cycloalkyl, 5-6 membered heteroaryl, and 4-7 membered heterocycloalkyl groups of R$^8$ are each optionally substituted with 1 or 2 R$^{19}$;

R$^{10}$ and R$^{11}$ are each independently selected from H, C$_{1-6}$ alkyl, C$_{2-6}$ alkenyl, C$_{2-6}$ alkynyl, C$_{1-6}$ haloalkyl, C$_{6-10}$ aryl, C$_3$-10 cycloalkyl, a 5-10 membered heteroaryl moiety having carbon and 1, 2, or 3 heteroatoms independently selected from N, O and S, and a 4-10 membered heterocycloalkyl moiety having carbon and 1, 2, or 3 heteroatoms independently selected from N, O and S; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl groups of R$^{10}$ and R$^{11}$ are each optionally substituted with 1, 2, 3, or 4 R$^{10A}$;

R$^{10A}$, at each occurrence, is independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, C$_{1-6}$ alkyl, C$_{2-6}$ alkenyl, C$_{2-6}$ alkynyl, C$_{1-6}$ haloalkyl, phenyl, C$_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-6}$ alkyl, C$_{2-6}$ alkenyl, C$_{2-6}$ alkynyl, phenyl, C$_{3-6}$ cycloalkyl, 5-6 membered heteroaryl, and 4-7 membered heterocycloalkyl group of R$^{10A}$ are each optionally substituted with 1, 2, or 3 substituents independently selected from R$^{19}$;

R$^{a4}$, R$^{b4}$, R$^{c4}$, and R$^{d4}$, at each occurrence, are independently selected from H, C$_{1-4}$ alkyl, C$_{2-4}$ alkenyl, C$_{2-4}$ alkynyl, C$_{1-4}$ haloalkyl, phenyl, C$_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said C$_{1-4}$ alkyl, C$_{2-4}$ alkenyl, C$_{2-4}$ alkynyl, phenyl, $C_{3-6}$ cycloalkyl, 5-6 membered heteroaryl, and 4-7 membered heterocycloalkyl group of $R^{a4}$, $R^{b4}$, $R^{c4}$, and $R^{d4}$ are each optionally substituted with 1, 2, or 3 substituents independently selected from $R^{19}$;

alternatively, $R^{c4}$ and $R^{d4}$ together with the nitrogen atom to which they are attached form a 4-, 5-, 6-, or 7-membered heterocycloalkyl group which is optionally substituted with 1, 2 or 3 substituents independently selected from $R^{19}$;

$R^{e4}$, at each occurrence, is H or $C_{1-4}$ alkyl;

alternatively, $R^{10}$ and $R^{11}$ together with the carbon atom to which they are attached form a 3-, 4-, 5-, 6-, or 7-membered cycloalkyl group or a 4-, 5-, 6-, 7-, 8-, 9-, or 10-membered heterocycloalkyl group; wherein said 3-, 4-, 5-, 6-, or 7-membered cycloalkyl group and 4-, 5-, 6-, 7-, 8-, 9-, or 10-membered heterocycloalkyl group are each optionally substituted with 1, 2, 3 or 4 $R^{10A}$;

$R^{12}$ is H or $C_{1-4}$ alkyl which is optionally substituted by $R^{17}$;

$R^{17}$, at each occurrence, is independently selected from halo, CN, $NO_2$, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $C(=NR^{e7})NR^{c7}R^{d7}$, $NR^{c7}C(=NR^{e7})NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{c7}R^{d7}$, $S(O)R^{b7}$, $S(O)NR^{c7}R^{d7}$, $S(O)_2R^{b7}$, $S(O)_2NR^{c7}R^{d7}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^{17}$ are each optionally substituted with 1, 2, or 3 substituents independently selected from $R^{19}$;

$R^{a7}$, $R^{b7}$, $R^{c7}$, and $R^{d7}$, at each occurrence, are independently selected from H, $C_{1-4}$ alkyl, $C_{2-4}$ alkenyl, $C_{2-4}$ alkynyl, $C_{1-4}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-4}$ alkyl, $C_{2-4}$ alkenyl, $C_{2-4}$ alkynyl, phenyl, $C_{3-6}$ cycloalkyl, 5-6 membered heteroaryl, and 4-7 membered heterocycloalkyl groups of $R^{a7}$, $R^{b7}$, $R^{c7}$, and $R^{d7}$ are each optionally substituted with 1, 2, or 3 substituents independently selected from $R^{19}$;

alternatively, $R^{c7}$ and $R^{d7}$ together with the nitrogen atom to which they are attached form a 4-, 5-, 6-, or 7-membered heterocycloalkyl group which is optionally substituted with 1, 2 or 3 substituents independently selected from $R^{19}$;

$R^{e7}$, at each occurrence, is independently H or $C_{1-4}$ alkyl;

$R^{19}$, at each occurrence, is independently selected from halo, CN, $NO_2$, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $C_{1-4}$ alkyl, $C_{2-4}$ alkenyl, $C_{2-4}$ alkynyl, and $C_{1-4}$ haloalkyl;

$R^{a9}$, $R^{c9}$, and $R^{d9}$, at each occurrence, are independently selected from H and $C_{1-4}$ alkyl; and $R^{b9}$, at each occurrence, is independently $C_{1-4}$ alkyl.

In some embodiments of compound of Formula (I), $R^7$ is selected from H, $C(O)NR^{c4}R^{d4}$, $S(O)R^{b4}$, $S(O)NR^{c4}R^{d4}$, $S(O)_2R^{b4}$, $S(O)_2NR^{c4}R^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, 5-6 membered heteroaryl having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^7$ are each optionally substituted with 1, 2, or 3 substituents independently selected from $R^{10A}$.

In some embodiments of compounds of Formula (I), the present disclosure provides an inhibitor of FGFR4, which is a compound having Formula (II):

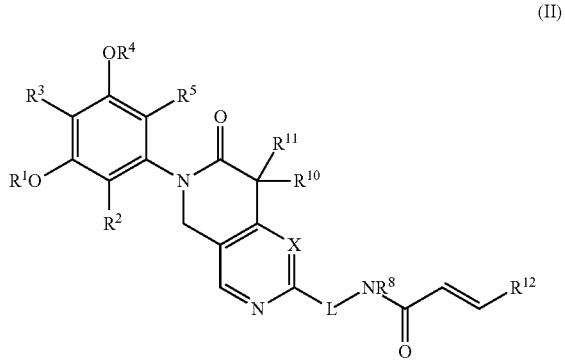

(II)

or a pharmaceutically acceptable salt thereof, wherein:

X is N or $CR^6$;

$R^1$ is $C_{1-3}$ alkyl or $C_{1-3}$ haloalkyl;

$R^2$ is H, halo, $C_{1-3}$ alkyl, $C_{1-3}$ haloalkyl, CN, or $C_{1-3}$ alkoxy;

$R^3$ is H, halo, $C_{1-3}$ alkyl, $C_{1-3}$ haloalkyl, CN, or $C_{1-3}$ alkoxy;

$R^4$ is $C_{1-3}$ alkyl or $C_{1-3}$ haloalkyl;

$R^5$ is H, halo, $C_{1-3}$ alkyl, $C_{1-3}$ haloalkyl, CN, or $C_{1-3}$ alkoxy;

$R^6$ is H, halo, CN, $OR^{a4}$, $SR^{a4}$, $C(O)NR^{c4}R^{d4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^6$ are each optionally substituted with 1, 2, or 3 substituents independently selected from $R^{10A}$;

L is $—(CR^{13}R^{14})_n—$, wherein $R^{13}$ and $R^{14}$ are each independently H, $C_{1-6}$ alkyl, $C_{6-10}$ aryl, 5 to 10 membered heteroaryl or 4 to 10 membered heterocycloalkyl, wherein the $C_{1-6}$ alkyl, $C_{6-10}$ aryl, 5 to 10 membered heteroaryl or 4 to 10 membered heterocycloalkyl is optionally substituted with from 1 to 3 $R^{17}$ groups wherein each $R^{17}$ member is optionally substituted with from 1-3 $R^{19}$ members; the subscript n is 1, 2 or 3;

$R^8$ is H or $C_{1-4}$ alkyl which is optionally substituted by halo, CN, $OR^{a9}$, $C(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, phenyl, $C_{3-7}$ cycloalkyl, a 5-6 membered heteroaryl moiety having carbon and 1, 2, or 3 heteroatoms independently selected from N, O and S, or a 4-7 membered heterocycloalkyl moiety having carbon and 1, 2, or 3 heteroatoms independently selected from N, O and S; wherein said phenyl, $C_{3-7}$ cycloalkyl, 5-6 membered heteroaryl, and 4-7 membered heterocycloalkyl groups of $R^8$ are each optionally substituted with 1 or 2 $R^{19}$;

$R^{10}$ is selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, a 5-10 membered heteroaryl moiety having carbon and 1, 2, or 3 heteroatoms independently selected from N, O and S, and a 4-10 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl groups of $R^{10}$ are each optionally substituted with 1, 2, 3, or 4 $R^{10A}$;

$R^{10A}$, at each occurrence, is independently selected from halo, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, S(O)$_2$NR$^{c4}$R$^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl group of $R^{10A}$ are each optionally substituted with 1, 2, or 3 substituents independently selected from $R^{19}$;

$R^{a4}$, $R^{b4}$, $R^{c4}$, and $R^{d4}$, at each occurrence, are independently selected from H, $C_{1-4}$ alkyl, $C_{2-4}$ alkenyl, $C_{2-4}$ alkynyl, $C_{1-4}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-4}$ alkyl, $C_{2-4}$ alkenyl, $C_{2-4}$ alkynyl, phenyl, $C_{3-6}$ cycloalkyl, 5-6 membered heteroaryl, and 4-7 membered heterocycloalkyl group of $R^{a4}$, $R^{b4}$, $R^{c4}$, and $R^{d4}$ are each optionally substituted with 1, 2, or 3 substituents independently selected from $R^{19}$;

alternatively, $R^{c4}$ and $R^{d4}$ together with the nitrogen atom to which they are attached form a 4-, 5-, 6-, or 7-membered heterocycloalkyl group which is optionally substituted with 1, 2 or 3 substituents independently selected from $R^{19}$;

$R^{e4}$ is H or $C_{1-4}$ alkyl;

$R^{11}$ is selected from $C_{1-6}$ alkyl, $C_{2-6}$ alkenyl, $C_{2-6}$ alkynyl, and $C_{1-6}$ haloalkyl; wherein said $C_{1-6}$ alkyl, $C_{2-6}$ alkenyl, and $C_{2-6}$ alkynyl are each optionally substituted with 1, 2 or 3 substituents independently selected from $R^{19}$;

alternatively, $R^{10}$ and $R^{11}$ together with the carbon atom to which they are attached form a 3-, 4-, 5-, 6-, or 7-membered cycloalkyl group or a 4-, 5-, 6-, 7-, 8-, 9-, or 10-membered heterocycloalkyl group; wherein said 3-, 4-, 5-, 6-, or 7-membered cycloalkyl group and 4-, 5-, 6-, 7-, 8-, 9-, or 10-membered heterocycloalkyl group are each optionally substituted with 1, 2, 3 or 4 $R^{10A}$;

$R^{12}$ is H or $C_{1-4}$ alkyl which is optionally substituted by $R^{17}$;

$R^{17}$, at each occurrence, is independently selected from halo, CN, NO$_2$, OR$^{a7}$, SR$^{a7}$, C(O)R$^{b7}$, C(O)NR$^{c7}$R$^{d7}$, C(O)OR$^{a7}$, OC(O)R$^{b7}$, OC(O)NR$^{c7}$R$^{d7}$, C(=NR$^{e7}$)NR$^{c7}$R$^{d7}$, NR$^{c7}$C(=NR$^{e7}$)NR$^{c7}$R$^{d7}$, NR$^{c7}$R$^{d7}$, NR$^{c7}$C(O)R$^{b7}$, NR$^{c7}$C(O)OR$^{a7}$, NR$^{c7}$C(O)NR$^{c7}$R$^{d7}$, NR$^{c7}$S(O)R$^{b7}$, NR$^{c7}$S(O)$_2$R$^{b7}$, NR$^{c7}$S(O)$_2$NR$^{c7}$R$^{d7}$, S(O)R$^{b7}$, S(O)NR$^{c7}$R$^{d7}$, S(O)$_2$R$^{b7}$, S(O)$_2$NR$^{c7}$R$^{d7}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^{17}$ are each optionally substituted with 1, 2, or 3 substituents independently selected from $R^{19}$;

$R^{a7}$, $R^{b7}$, $R^{c7}$, and $R^{d7}$, at each occurrence, are independently selected from H, $C_{1-4}$ alkyl, $C_{2-4}$ alkenyl, $C_{2-4}$ alkynyl, $C_{1-4}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-4}$ alkyl, $C_{2-4}$ alkenyl, $C_{2-4}$ alkynyl, phenyl, $C_{3-6}$ cycloalkyl, 5-6 membered heteroaryl, and 4-7 membered heterocycloalkyl groups of $R^{a7}$, $R^{b7}$, $R^{c7}$, and $R^{d7}$ are each optionally substituted with 1, 2, or 3 substituents independently selected from $R^{19}$;

alternatively, $R^{c7}$ and $R^{d7}$ together with the nitrogen atom to which they are attached form a 4-, 5-, 6-, or 7-membered heterocycloalkyl group which is optionally substituted with 1, 2 or 3 substituents independently selected from $R^{19}$;

$R^{e7}$, at each occurrence, is H or $C_{1-4}$ alkyl;

$R^{19}$, at each occurrence, is independently selected from halo, CN, NO$_2$, OR$^{a9}$, SR$^{a9}$, C(O)R$^{b9}$, C(O)NR$^{c9}$R$^{d9}$, C(O)OR$^{a9}$, OC(O)R$^{b9}$, OC(O)NR$^{c9}$R$^{d9}$, NR$^{c9}$R$^{d9}$, NR$^{c9}$C(O)R$^{b9}$, NR$^{c9}$C(O)OR$^{a9}$, NR$^{c9}$C(O)NR$^{c9}$R$^{d9}$, NR$^{c9}$S(O)R$^{b9}$, NR$^{c9}$S(O)$_2$R$^{b9}$, NR$^{c9}$S(O)$_2$NR$^{c9}$R$^{d9}$, S(O)R$^{b9}$, S(O)NR$^{c9}$R$^{d9}$, S(O)$_2$R$^{b9}$, S(O)$_2$NR$^{c9}$R$^{d9}$, $C_{1-4}$ alkyl, $C_{2-4}$ alkenyl, $C_{2-4}$ alkynyl, and $C_{1-4}$ haloalkyl;

$R^{a9}$, $R^{c9}$, and $R^{d9}$, at each occurrence, are independently selected from H and $C_{1-4}$ alkyl; and $R^{b9}$, at each occurrence, is $C_{1-4}$ alkyl.

In some embodiments of compounds of Formula (I), the present disclosure provides compounds or pharmaceutically acceptable salts thereof, which are FGFR4 inhibitors and have Formula (III):

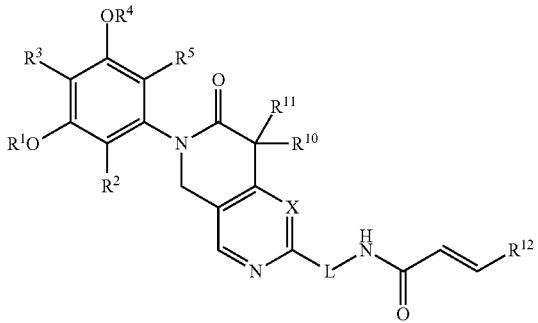

(III)

The variables $R^1$, $R^2$, $R^3$, $R^4$, $R^5$, $R^{10}$, $R^{11}$, $R^{12}$, X and L are as defined in any embodiment of compound of Formula (I).

In some embodiments of compounds of Formula (I), the present disclosure provides compounds, or pharmaceutically acceptable salts thereof, which are FGFR4 inhibitors and have Formula (IV):

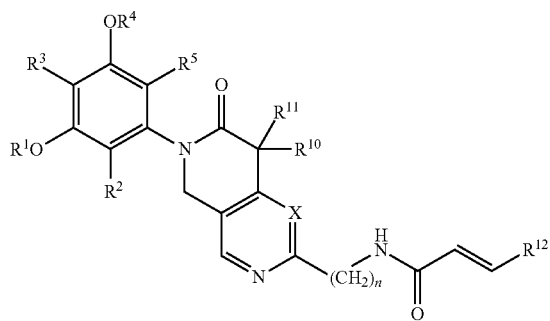

(IV)

The variables $R^1$, $R^2$, $R^3$, $R^4$, $R^5$, $R^{10}$, $R^{11}$, $R^{12}$, X and n are as defined in any embodiment of compound of Formula (I).

In some embodiments of compounds of Formula (I), the present disclosure provides compounds of Formula (V) or pharmaceutically acceptable salts thereof, which have FGFR4 inhibitory activities.

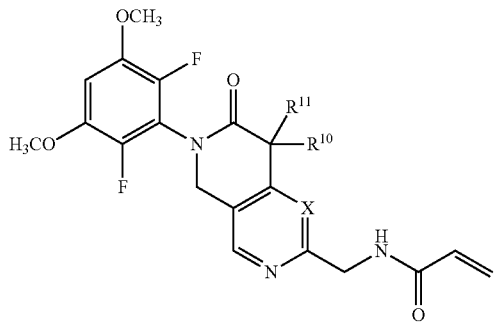

(V)

In some embodiments of compounds of Formula (V), $R^{10}$ and $R^{11}$ are taken together with the carbon atom to which they are attached form $C_{3-6}$ cycloalkyl, optionally substituted with 1 or 2 $R^{10A}$ groups.

In certain embodiments of compounds of Formula (I), $R^{10}$ and $R^{11}$ together with the carbon atom to which they are attached form a cyclopropyl, cyclobutyl, cyclopentyl or cyclohexyl group. In one embodiment, X is CH. In another embodiment, X is N.

In some embodiments of compounds of Formula (I), the present disclosure provides compounds of Formula (VI) or pharmaceutically acceptable salts thereof, which have FGFR4 inhibitory activities.

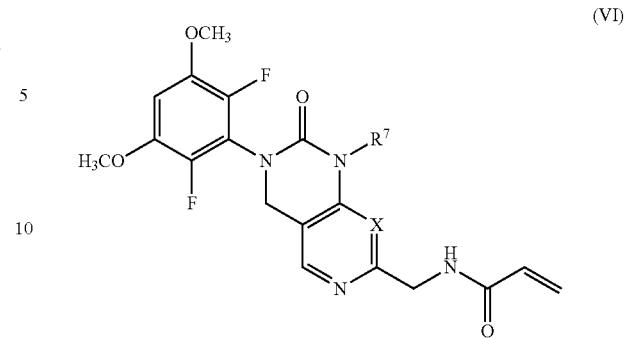

(VI)

In some embodiments of compounds of Formula (VI), $R^7$ is $C_{1-6}$ alkyl, phenyl, 5- or 6-membered heteroaryl, $C_{3-6}$ cycloalkyl or 4- to 6-membered heterocycloalkyl, each of which is optionally substituted with from 1-2 members selected from halo, $C_{1-4}$ alkyl, CN, $C_{1-4}$ haloalkyl, $C_{1-4}$ alkoxy, phenyl, $C_{3-6}$ cycloalkyl, 5- or 6-membered heteroaryl, $C_{3-6}$ cycloalkyl or 4- to 6-membered heterocycloalkyl.

In certain embodiments of compounds of Formula (I), $R^7$ is methyl, ethyl, isopropyl, n-butyl, cyanomethyl, 2,2,2-trifluoroethyl, phenyl, 3-pyridyl, 1-methyl-1H-pyrazol-3-yl, 1-methyl-1H-pyrazol-4-yl, tetrahydrofuran-3-yl, 3,3-difluorocyclobutyl, 2-methoxyethyl, cyclopropylmethyl, 2,2-difluoroethyl, benzyl, 3-fluorobenzyl, pyridin-3-ylmethyl, (1-methyl-1H-pyrazol-4-yl)methyl, (1-methyl-1H-pyrazol-3-yl)methyl or (tetrahydrofuran-3-yl)methyl. In one embodiment, X is CH. In another embodiment, X is N.

In some embodiments the present disclosure provides inhibitors of FGFR4 having Formula (Ia):

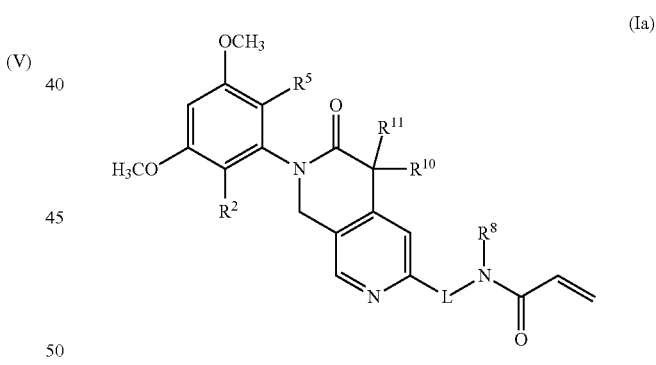

(Ia)

or a pharmaceutically acceptable salt thereof, wherein:
$R^2$ is F or Cl;
$R^5$ is F or Cl;
L is —$(CR^{13}R^{14})_n$—, wherein $R^{13}$ and $R^{14}$ are each independently H, $C_{1-6}$ alkyl or $C_{6-10}$ aryl, wherein the $C_{1-6}$ alkyl or $C_{6-10}$ aryl is optionally substituted with from 1 to 3 $R^{17}$ groups; or $R^{13}$ and $R^{14}$ are taken together with the carbon atom to which they are attached form a $C_{3-6}$ cycloalkyl or 4 to 6-membered heterocycloalkyl group; wherein the $C_{3-6}$ cycloalkyl or 4 to 6-membered heterocycloalkyl group is optionally substituted with from 1 to 3 $R^{17}$;
$R^8$ is H or methyl;
$R^{10}$ is selected from $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, a 5-10 membered heteroaryl moiety having carbon and 1, 2, or 3 heteroatoms independently selected from N, O and S, and a 4-10 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl groups of $R^{10}$ are each optionally substituted with 1, 2, 3, or 4 $R^{10A}$;

$R^{10A}$, at each occurrence, is independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, $S(O)_2NR^{c4}R^{d4}$, $C_{1-6}$ alkyl, $C_{2-6}$ alkenyl, $C_{2-6}$ alkynyl, $C_{1-6}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety having carbon and 1, 2, or 3 heteroatoms independently selected from N, O and S; wherein said $C_{1-6}$ alkyl, $C_{2-6}$ alkenyl, $C_{2-6}$ alkynyl, phenyl, $C_{3-6}$ cycloalkyl, 5-6 membered heteroaryl, and 4-7 membered heterocycloalkyl groups of $R^{10a}$ are each optionally substituted with 1, 2, or 3 substituents independently selected from $R^{19}$;

$R^{a4}$, $R^{b4}$, $R^{c4}$, and $R^{d4}$, at each occurrence, are independently selected from H, $C_{1-4}$ alkyl, $C_{2-4}$ alkenyl, $C_{2-4}$ alkynyl, $C_{1-4}$ haloalkyl, phenyl, $C_{3-6}$ cycloalkyl, a 5-6 membered heteroaryl moiety having carbon and 1, 2, or 3 heteroatoms independently selected from N, O and S, and a 4-7 membered heterocycloalkyl moiety comprising carbon and 1, 2, or 3 heteroatoms independently selected from N, O and S; wherein said $C_{1-4}$ alkyl, $C_{2-4}$ alkenyl, $C_{2-4}$ alkynyl, phenyl, $C_{3-6}$ cycloalkyl, 5-6 membered heteroaryl, and 4-7 membered heterocycloalkyl groups of $R^{a4}$, $R^{b4}$, $R^{c4}$, and $R^{d4}$ are each optionally substituted with 1, 2, or 3 substituents independently selected from $R^{19}$;

alternatively, $R^{c4}$ and $R^{d4}$ together with the nitrogen atom to which they are attached form a 4-, 5-, 6-, or 7-membered heterocycloalkyl group which is optionally substituted with 1, 2 or 3 substituents s independently selected from $R^{19}$;

$R^{e4}$, at each occurrence, is independently H or $C_{1-4}$ alkyl;

$R^{11}$ is selected from $C_{1-6}$ alkyl, $C_{2-6}$ alkenyl, $C_{2-6}$ alkynyl, and $C_{1-6}$ haloalkyl;

alternatively, $R^{10}$ and $R^{11}$ together with the carbon atom to which they are attached form a 3-, 4-, 5-, 6-, or 7-membered cycloalkyl group or a 4-, 5-, 6-, or 7-membered heterocycloalkyl group; wherein said 3-, 4-, 5-, 6-, or 7-membered cycloalkyl group and 4-, 5-, 6-, or 7-membered heterocycloalkyl group are each optionally substituted with 1, 2, 3 or 4 $R^{10A}$;

$R^{17}$, at each occurrence, is independently selected from OH, CN, amino, halo, $C_{1-6}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

$R^{19}$, at each occurrence, is independently selected from halo, CN, $NO_2$, $OR^{a9}$, $SR^{a9}$, $C(O)R^{b9}$, $C(O)NR^{c9}R^{d9}$, $C(O)OR^{a9}$, $OC(O)R^{b9}$, $OC(O)NR^{c9}R^{d9}$, $NR^{c9}R^{d9}$, $NR^{c9}C(O)R^{b9}$, $NR^{c9}C(O)OR^{a9}$, $NR^{c9}C(O)NR^{c9}R^{d9}$, $NR^{c9}S(O)R^{b9}$, $NR^{c9}S(O)_2R^{b9}$, $NR^{c9}S(O)_2NR^{c9}R^{d9}$, $S(O)R^{b9}$, $S(O)NR^{c9}R^{d9}$, $S(O)_2R^{b9}$, $S(O)_2NR^{c9}R^{d9}$, $C_{1-4}$ alkyl, $C_{2-4}$ alkenyl, $C_{2-4}$ alkynyl, and $C_{1-4}$ haloalkyl;

$R^{a9}$, $R^{c9}$, and $R^{d9}$, at each occurrence, are independently selected from H and $C_{1-4}$ alkyl; and $R^{b9}$, at each occurrence, is independently $C_{1-4}$ alkyl.

In some embodiments of compounds of Formula (Ia) as described above, L is —$(CR^{13}R^{14})_n$—, wherein $R^{13}$ and $R^{14}$ are each independently H, $C_{1-6}$ alkyl, and $C_{6-10}$ aryl, wherein the $C_{1-6}$ alkyl and $C_{6-10}$ aryl is optionally substituted with from 1 to 3 independently selected $R^{17}$ groups.

In some embodiments, X is N.

In some embodiments, X is $CR^6$.

In some embodiments, $R^6$ is H, halo, CN, or $C_{1-6}$ alkyl. In some embodiments, $R^6$ is H. In some embodiments, $R^6$ is $C_{1-6}$ alkyl. In some embodiments, $R^6$ is methyl. In some embodiments, $R^6$ is halo. In some embodiments, $R^6$ is CN.

In some embodiments, $R^1$ is $C_{1-3}$ alkyl. In some embodiments, $R^1$ is methyl.

In some embodiments, $R^2$ is halo. In some embodiments, $R^2$ is fluoro. In some embodiments, $R^2$ is chloro.

In some embodiments, $R^3$ is H.

In some embodiments, $R^4$ is $C_{1-3}$ alkyl. In some embodiments, $R^4$ is methyl.

In some embodiments, $R^5$ is halo. In some embodiments, $R^5$ is fluoro. In some embodiments, $R^5$ is chloro.

In some embodiments, $R^2$ is fluoro and $R^5$ is fluoro. In some embodiments, $R^2$ is chloro and $R^5$ is chloro.

In some embodiments, $R^7$ is $C_{1-6}$ alkyl, phenyl, 5- or 6-membered heteroaryl, $C_{3-6}$ cycloalkyl or 4- to 6-membered heterocycloalkyl, each of which is optionally substituted with from 1-2 members selected from halo, $C_{1-4}$ alkyl, CN, $C_{1-4}$ haloalkyl, $C_{1-4}$ alkoxy, phenyl, $C_{3-6}$ cycloalkyl, 5- or 6-membered heteroaryl, or 4- to 6-membered heterocycloalkyl.

In some embodiments, $R^7$ is methyl, ethyl, propyl, isopropyl, n-butyl, cyanomethyl, 2,2,2-trifluoroethyl, phenyl, 3-pyridyl, 1-methyl-1H-pyrazol-3-yl, 1-methyl-1H-pyrazol-4-yl, tetrahydrofuran-3-yl, 3,3-difluorocyclobutyl, 2-methoxyethyl, cyclopropyl, cyclopropylmethyl, 2,2-difluoroethyl, benzyl, 3-fluorobenzyl, pyridin-3-ylmethyl, (1-methyl-1H-pyrazol-4-yl)methyl, (1-methyl-1H-pyrazol-3-yl)methyl, (tetrahydrofuran-3-yl)methyl, 2-fluoroethyl, 4-pyridyl, (piperidin-4-yl)methyl, (1-methylpiperidin-4-yl)methyl, (1-methoxycarbonylpiperidin-4-yl)methyl, (1-methyl sulfonylpiperidin-4-yl)methyl, tetrahydropyran-4-yl, cyclobutyl, cyclopentyl, isobutyl, 1-(cyclobutylmethyl), or 4-methyl-N-isopropylpiperidine-1-carboxamide.

In some embodiments, $R^7$ is methyl, ethyl, propyl, isopropyl, n-butyl, cyanomethyl, 2,2,2-trifluoroethyl, phenyl, 3-pyridyl, 1-methyl-1H-pyrazol-3-yl, 1-methyl-1H-pyrazol-4-yl, tetrahydrofuran-3-yl, 3,3-difluorocyclobutyl, 2-methoxyethyl, cyclopropyl, cyclopropylmethyl, 2,2-difluoroethyl, benzyl, 3-fluorobenzyl, pyridin-3-ylmethyl, (1-methyl-1H-pyrazol-4-yl)methyl, (1-methyl-1H-pyrazol-3-yl)methyl or (tetrahydrofuran-3-yl)methyl.

In some embodiments, $R^7$ is ethyl, propyl, isopropyl, cyanomethyl, 2,2,2-trifluoroethyl, 2,2-difluoroethyl, phenyl, 3-pyridyl, 1-methyl-1H-pyrazol-3-yl, tetrahydrofuran-3-yl, 3,3-difluorocyclobutyl, 2-methoxyethyl, cyclopropyl, cyclopropylmethyl, 3-fluorobenzyl, pyridin-3-ylmethyl, (1-methyl-1H-pyrazol-4-yl)methyl, or (tetrahydrofuran-3-yl)methyl.

In some embodiments, $R^7$ is 2-fluoroethyl, 4-pyridyl, (piperidin-4-yl)methyl, (1-methylpiperidin-4-yl)methyl, (1-methoxycarbonylpiperidin-4-yl)methyl, (1-methylsulfonylpiperidin-4-yl)methyl, tetrahydropyran-4-yl, cyclobutyl, cyclopentyl, isobutyl, 1-(cyclobutylmethyl), or 4-methyl-N-isopropylpiperidine-1-carboxamide.

In some embodiments, $R^1$ is $C_{1-3}$ alkyl; $R^2$ is halo; $R^3$ is H; $R^4$ is $C_{1-3}$ alkyl; and $R^5$ is halo.

In some embodiments, $R^1$ is $C_{1-3}$ alkyl; $R^2$ is F; $R^3$ is H; $R^4$ is $C_{1-3}$ alkyl; and $R^5$ is F.

In some embodiments, $R^1$ is methyl; $R^2$ is F; $R^3$ is H; $R^4$ is methyl; and $R^5$ is F.

In some embodiments, $R^1$ is $C_{1-3}$ alkyl; $R^2$ is Cl; $R^3$ is H; $R^4$ is $C_{1-3}$ alkyl; and $R^5$ is Cl.

In some embodiments, $R^1$ is methyl; $R^2$ is Cl; $R^3$ is H; $R^4$ is methyl; and $R^5$ is Cl.

In some embodiments, $R^{10}$ is $C_{1-6}$ alkyl. In some embodiments, $R^{10}$ is methyl.

In some embodiments, $R^{11}$ is $C_{1-6}$ alkyl. In some embodiments, $R^{11}$ is methyl.

In some embodiments, $R^{10}$ and $R^{11}$ are each $C_{1-6}$ alkyl. In some embodiments, $R^{10}$ and $R^{11}$ are each methyl.

In some embodiments, $R^{10}$ and $R^{11}$ together with the carbon atom to which they are attached form a 3-, 4-, 5-, 6-, or 7-membered cycloalkyl group. In some embodiments, $R^{10}$ and $R^{11}$ together with the carbon atom to which they are attached form a 3-, 4-, 5-, or 6-membered cycloalkyl group. In some embodiments, $R^{10}$ and $R^{11}$ together with the carbon atom to which they are attached form a 3-, 4-, or 5-membered cycloalkyl group.

In some embodiments, $R^{10}$ and $R^{11}$ together with the carbon atom to which they are attached form a cyclopropyl group. In some embodiments, $R^{10}$ and $R^{11}$ together with the carbon atom to which they are attached form a cyclobutyl group. In some embodiments, $R^{10}$ and $R^{11}$ together with the carbon atom to which they are attached form a cyclopentyl group. In some embodiments, $R^{10}$ and $R^{11}$ together with the carbon atom to which they are attached form a cyclohexyl group. In some embodiments, $R^{10}$ and $R^{11}$ together with the carbon atom to which they are attached form a cycloheptyl group.

In some embodiments, $R^{10}$ and $R^{11}$ together with the carbon atom to which they are attached form a cyclopropyl group optionally substituted by 1 or 2 $R^{10A}$. In some embodiments, $R^{10}$ and $R^{11}$ together with the carbon atom to which they are attached form a cyclobutyl group optionally substituted by 1 or 2 $R^{10A}$. In some embodiments, $R^{10}$ and $R^{11}$ together with the carbon atom to which they are attached form a cyclopentyl group optionally substituted by 1 or 2 $R^{10A}$. In some embodiments, $R^{10}$ and $R^{11}$ together with the carbon atom to which they are attached form a cyclohexyl group optionally substituted by 1 or 2 $R^{10A}$.

In some embodiments, $R^{10}$ and $R^{11}$ together with the carbon atom to which they are attached form a cyclopropyl, cyclobutyl, cyclopentyl or cyclohexyl group.

In some embodiments, $R^{10}$ and $R^{11}$ together with the carbon atom to which they are attached form a cyclopropyl or cyclopentyl group.

In some embodiments, $R^{10}$ and $R^{11}$ together with the carbon atom to which they are attached form a 4-, 5-, 6-, or 7-membered heterocycloalkyl group.

In some embodiments, $R^{10}$ and $R^{11}$ together with the carbon atom to which they are attached form a tetrahydropyranyl group (e.g., 2-tetrahydropyranyl, 3-tetrahydropyranyl or 4-tetrahydropyranyl), a tetrahydrofuranyl group (e.g., 2-tetrahydrofuranyl or 3-tetrahydrofuranyl), tetrahydrothiophenyl group (e.g., 2-tetrahydrothiophenyl or 3-tetrahydrothiophenyl), a pyrrolidinyl group (e.g., 2-pyrrolidinyl or 3-pyrrolidinyl), a piperidinyl group (e.g., 2-piperidinyl, 3-piperidinyl or 4-piperidinyl), 2-morpholinyl or 3-morpholinyl, each of which is optionally substituted with 1 or 2 $R^{10A}$ groups. In some embodiments, $R^{10}$ and $R^{11}$ together with the carbon atom to which they are attached form a tetrahydropyranyl group. In some embodiments, $R^{10}$ and $R^{11}$ together with the carbon atom to which they are attached form a tetrahydropyranyl group optionally substituted by 1 or 2 $R^{10A}$. In some embodiments, $R^{10}$ and $R^{11}$ together with the carbon atom to which they are attached form a tetrahydrofuranyl group. In some embodiments, $R^{10}$ and $R^{11}$ together with the carbon atom to which they are attached form a tetrahydrofuranyl group optionally substituted by $R^{10A}$. In some embodiments, $R^{10}$ and $R^{11}$ together with the carbon atom to which they are attached form an azetidinyl group. In some embodiments, $R^{10}$ and $R^{11}$ together with the carbon atom to which they are attached form an azetidinyl group optionally substituted by $R^{10A}$.

In some embodiments, L is $-(CR^{13}R^{14})_n-$, wherein $R^{13}$ and $R^{14}$ are each independently H, $C_{1-6}$ alkyl, $C_{6-10}$ aryl, 5-10 membered heteroaryl or 4-10 membered heterocycloalkyl, each of which is optionally substituted with from 1-3 $R^{17}$ groups; and n is 1 or 2. In some embodiments, L is $-(CR^{13}R^{14})_n-$, wherein $R^{13}$ and $R^{14}$ are each independently H, $C_{1-6}$ alkyl, $C_{6-10}$ aryl, 5-10 membered heteroaryl or 4-10 membered heterocycloalkyl.

In some embodiments, L is $-(CR^{13}R^{14})_n-$, wherein $R^{13}$ and $R^{14}$ are each independently H or $R^{13}$ and $R^{14}$ taken together with the carbon atom to which they are attached form a 3 to 6 membered cycloalkyl group or 4 to 7-membered heterocycloalkyl group, where the 3 to 6 membered cycloalkyl group or 4 to 7-membered heterocycloalkyl group is optionally substituted with from 1 or 2 $R^{17}$ groups. In some embodiments, L is $-(CR^{13}R^{14})_n-$, wherein $R^{13}$ and $R^{14}$ are each independently H or $R^{13}$ and $R^{14}$ taken together with the carbon atom to which they are attached form a 3 to 6 membered cycloalkyl group or 4 to 7-membered heterocycloalkyl group.

In some embodiments, L is $-CH_2C(R^{13})(R^{14})-$ or $-C(R^{13})(R^{14})CH_2-$, where $R^{13}$ and $R^{14}$ taken together with the carbon atom to which they are attached form cyclopropyl, cyclobutyl, cyclopentyl or cyclohexyl group, each of which is optionally substituted with 1 or 2 $R^{17}$ groups. In some embodiments, L is $-CH_2C(R^{13})(R^{14})-$ or $-C(R^{13})(R^{14})CH_2-$, where $R^{13}$ and $R^{14}$ taken together with the carbon atom to which they are attached form cyclopropyl, cyclobutyl, cyclopentyl or cyclohexyl group.

In some embodiments, L is $-CH_2C(R^{13})(R^{14})-$ or $-C(R^{13})(R^{14})CH_2-$, where $R^{13}$ and $R^{14}$ taken together with the carbon atom to which they are attached form a tetrahydropyranyl group (e.g., 2-tetrahydropyranyl, 3-tetrahydropyranyl or 4-tetrahydropyranyl), a tetrahydrofuranyl group (e.g., 2-tetrahydrofuranyl or 3-tetrahydrofuranyl), tetrahydrothiophenyl group (e.g., 2-tetrahydrothiophenyl or 3-tetrahydrothiophenyl), a pyrrolidinyl group (e.g., 2-pyrrolidinyl or 3-pyrrolidinyl), a piperidinyl group (e.g., 2-piperidinyl, 3-piperidinyl or 4-piperidinyl), 2-morpholinyl or 3-morpholinyl, each of which is optionally substituted with 1 or 2 $R^{17}$ groups. In some embodiments, L is $-CH_2C(R^{13})(R^{14})-$ or $-C(R^{13})(R^{14})CH_2-$, where $R^{13}$ and $R^{14}$ taken together with the carbon atom to which they are attached form a tetrahydropyranyl group (e.g., 2-tetrahydropyranyl, 3-tetrahydropyranyl or 4-tetrahydropyranyl), a tetrahydrofuranyl group (e.g., 2-tetrahydrofuranyl or 3-tetrahydrofuranyl), tetrahydrothiophenyl group (e.g., 2-tetrahydrothiophenyl or 3-tetrahydrothiophenyl), a pyrrolidinyl group (e.g., 2-pyrrolidinyl or 3-pyrrolidinyl), a piperidinyl group (e.g., 2-piperidinyl, 3-piperidinyl or 4-piperidinyl), 2-morpholinyl or 3-morpholinyl.

In some embodiments, L is $-(CH_2)_n-$, where n is 1, 2 or 3. In one embodiment, L is $CH_2$.

In some embodiments, L is $-(CH_2)_n-$, where n is 1 or 2.

In a preferred embodiment, $R^8$ is H. In another preferred embodiment, $R^{12}$ is H. In another preferred embodiment, X is CH. In another preferred embodiment, X is N.

In some embodiments, $R^{17}$ is methyl.

In some embodiments, $R^8$ is H or $C_{1-4}$ alkyl. In some embodiments, $R^8$ is H or methyl. In some embodiments, $R^8$ is H. In some embodiments, $R^8$ is methyl.

In some embodiments, $R^{12}$ is H or $C_{1-4}$ alkyl which is optionally substituted by $R^{17}$; wherein $R^{17}$, at each occurrence, is independently selected from halo, CN, $OR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)OR^{a7}$, $NR^{c7}C(O)NR^{c7}R^{d7}$, $NR^{c7}S(O)R^{b7}$, $NR^{c7}S(O)_2R^{b7}$, $NR^{c7}S(O)_2NR^{d7}R^{d7}$, $S(O)R^{b7}$, $S(O)NR^{c7}R^{d7}$, $S(O)_2R^{b7}$, $C_{1-4}$ alkyl, $C_{2-4}$ alkenyl, $C_{2-4}$ alkynyl, and $C_{1-4}$ haloalkyl.

In some embodiments, $R^{a7}$, $R^{c7}$, and $R^{d7}$, at each occurrence, are independently selected from H and $C_{1-4}$ alkyl; and each $R^{b7}$ is independently $C_{1-4}$ alkyl.

In some embodiments, $R^{12}$ is H or $C_{1-4}$ alkyl. In some embodiments, $R^{12}$ is $C_{1-4}$ alkyl. In some embodiments, $R^{12}$ is $C_{1-4}$ alkyl substituted by $-N(CH_3)_2$. In some embodiments, $R^{12}$ is $-CH_2-N(CH_3)_2$. In some embodiments, $R^{12}$ is methyl. In some embodiments, $R^{12}$ is $C_{1-4}$ alkyl substituted by piperidin-1-yl. In some embodiments, $R^{12}$ is $-CH_2$(piperidin-1-yl).

In some embodiments, $R^{12}$ is H.

In some embodiments, the present disclosure provides an inhibitor of FGFR4 which is a compound having Formula (Ib):

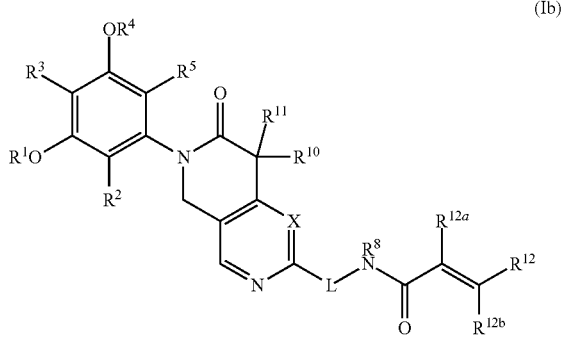

(Ib)

or a pharmaceutically acceptable salt thereof, wherein X, L, $R^1$, $R^2$, $R^3$, $R^4$, $R^5$, $R^8$, $R^{10}$, $R^{11}$, and $R^{12}$ are as defined herein; $R^{12a}$ is H; and $R^{12b}$ is H.

In some embodiments the present invention is an inhibitor of FGFR4 which is a compound having Formula (Ic):

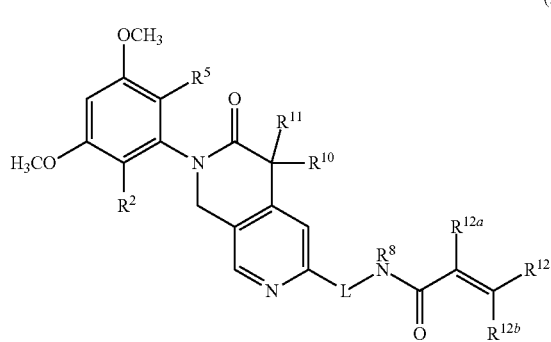

(Ic)

or a pharmaceutically acceptable salt thereof, wherein L, $R^2$, $R^5$, $R^8$, $R^{10}$, $R^{11}$, and $R^{12}$ are as defined herein; $R^{12a}$ is H; and $R^{12b}$ is H.

In some embodiments, $R^{12a}$ is H, F, methyl, or trifluoromethyl.

In some embodiments, $R^{12b}$ is H, F, methyl, or trifluoromethyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

Definitions

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, and the like. In some embodiments, the alkyl group is methyl, ethyl, or propyl.

As used herein, the term "$C_{i-j}$ alkylene," employed alone or in combination with other terms, means a saturated divalent linking hydrocarbon group that may be straight-chain or branched, having i to j carbons. In some embodiments, the alkylene group contains from 1 to 4 carbon atoms, from 1 to 3 carbon atoms, or from 1 to 2 carbon atoms. Examples of alkylene moieties include, but are not limited to, chemical groups such as methylene, ethylene, 1,1-ethylene, 1,2-ethylene, 1,3-propylene, 1,2-propylene, 1,1-propylene, isopropylene, and the like.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. In some embodiments, the alkynyl moiety contains 2 to 6 or 2 to 4 carbon atoms. Example alkynyl groups include, but are not limited to, ethynyl, propyn-1-yl, propyn-2-yl, and the like.

As used herein, "halo" or "halogen", employed alone or in combination with other terms, includes fluoro, chloro, bromo, and iodo. In some embodiments, halo is F or Cl. In some embodiments, halo is F.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6, 1 to 4, or 1 to 3 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. In some embodiments, the alkyl group has 1 to 6, 1 to 4, or 1 to 3 carbon atoms. Example alkoxy groups include methoxy, ethoxy, propoxy (e.g., n-propoxy and isopropoxy), t-butoxy, and the like. In some embodiments, alkoxy is methoxy.

As used herein, "haloalkoxy," employed alone or in combination with other terms, refers to a group of formula —O-(haloalkyl). In some embodiments, the alkyl group has 1 to 6, 1 to 4, or 1 to 3 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "alkylthio," employed alone or in combination with other terms, refers to a group of formula —S-alkyl. In some embodiments, the alkyl group has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members, or 3 to 6 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or 3 to 8 ring forming atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In some embodiments, the heterocycloalkyl is a 4-7 membered heterocycloalkyl moiety having carbon and 1, 2, or 3 heteroatoms independently selected from N, O and S. In some embodiments, the heterocycloalkyl is 4-10 membered heterocycloalkyl moiety having carbon and 1, 2, or 3 heteroatoms independently selected from N, O and S.

As used herein, the term "aryl," employed alone or in combination with other terms, refers to a monocyclic or polycyclic (e.g., having 2 fused rings) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "heteroaryl," employed alone or in combination with other terms, refers to a monocyclic or polycyclic (e.g., having 2 or 3 fused rings) aromatic hydrocarbon moiety, having one or more heteroatom ring members independently selected from nitrogen, sulfur and oxygen. In some embodiments, the heteroaryl group is a monocyclic or bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In one embodiment the heteroaryl group is a 5 to 10 membered heteroaryl group. In another embodiment the heteroaryl group is a 5 to 6 membered heteroaryl group. In some embodiments, the heteroaryl is a 5-6 membered heteroaryl moiety having carbon and 1, 2, or 3 heteroatoms independently selected from N, O and S. In some embodiments, the heteroaryl is a 5-10 membered heteroaryl moiety having carbon and 1, 2, or 3 heteroatoms independently selected from N, O and S.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids.

Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like. Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamineimine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); PMB (paramethoxybenzyl), POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); g (microgram (s)); L (microliter(s)); M (micromolar); wt % (weight percent).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared by one skilled in the art according to preparatory routes known in the literature. Example synthetic methods for preparing compounds of the invention are provided in the Schemes below.

Compounds of formula 4 can be synthesized using procedures as outlined in Scheme 1. Reduction of ester 1 using diisobutylaluminium hydride (DIBAL-H) can afford the corresponding aldehyde 2. Reductive amination of aldehyde 2 with aniline 3 using a suitable reducing agent such as sodium triacetoxyborohydride [Na(OAc)$_3$BH] in the presence of an acid such as acetic acid or trifluoroacetic acid (TFA) can afford the amine of formula 4.

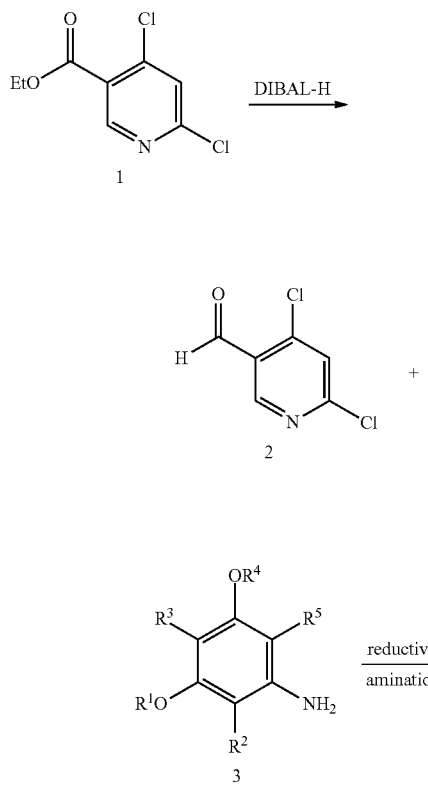

Scheme 1

-continued

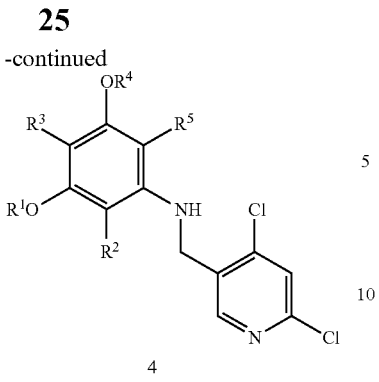

4

The substituted dichloropyrimidine of formula 8 can be prepared by the method described in Scheme 2. Treatment of the commercially available 5-(chloromethyl)pyrimidine-2,4 (1H,3H)-dione, 5, with phosphoryl chloride ($POCl_3$) can afford the trichloride pyrimidine of formula 6. Compound 6 can be converted to the iodide of formula 7 using sodium iodide (NaI), tetrabutylammonium iodide ($Bu_4NI$), or an equivalent iodide reagent. Compound 7 can be coupled with aniline 3 in the presence of a suitable base, such as diisopropylethylamine ($^iPr_2NEt$), cesium carbonate ($Cs_2CO_3$), or sodium hydride (NaH), to give the dichloropyrimidine of formula 8.

Scheme 2

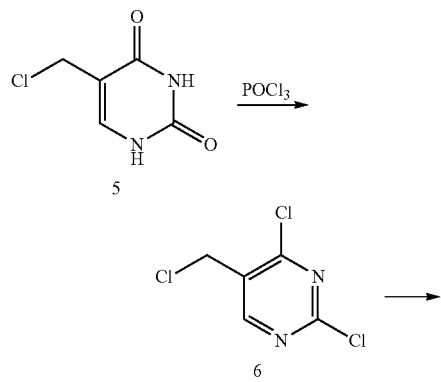

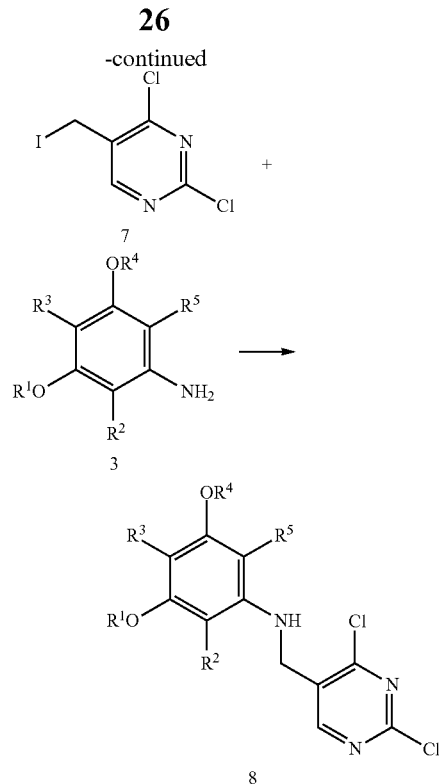

The synthesis of compound 14 is outlined in Scheme 3. Compound 9 can be treated with ethyl 3-chloro-3-oxopropanoate and NaH in THF to provide amide 10. Lactam 11 can be prepared by the treatment of compounds 10 with a strong base, such as NaH or $Cs_2CO_3$ in DMF, and followed by an acid, such as HCl, mediated decarboxylation. α-Substituted lactam 12 can be obtained by treating compound 11 with a base, such as NaH or $Cs_2CO_3$ in DMF or acetonitrile, and followed by the addition of halides $R^{10}X$ and/or $R^{11}X$ (X is halo such as Cl, Br, or I). Chloride 12 can be converted to the compound 13 when treated with $Zn(CN)_2$/Pd(dppf)$_2Cl_2$ in DMF. The reduction of compound 13 with DIBAL-H can give the corresponding amine, the acryloylation of which with acryloyl chloride in the presence of a base, such as $iPr_2NEt$, can afford amide 14.

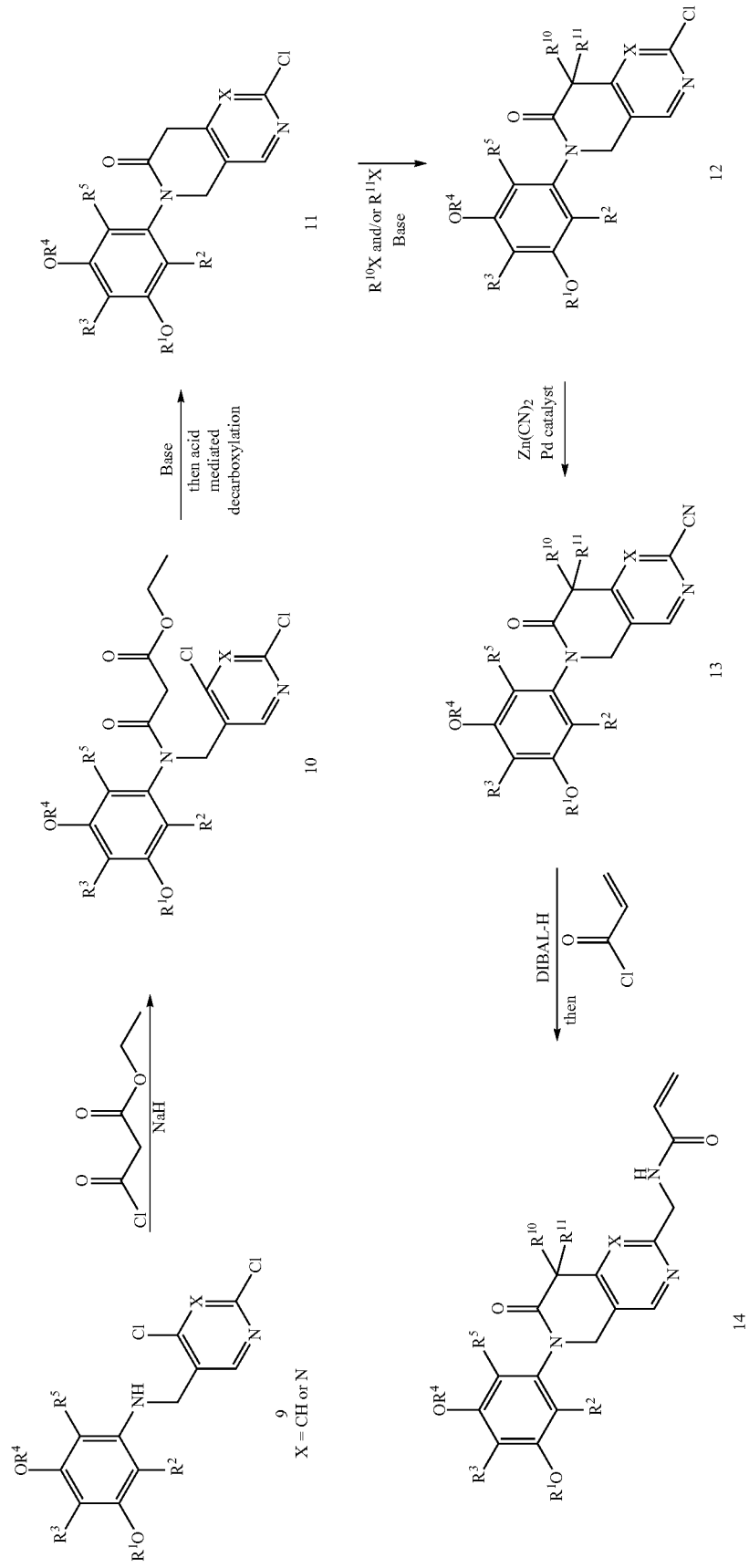

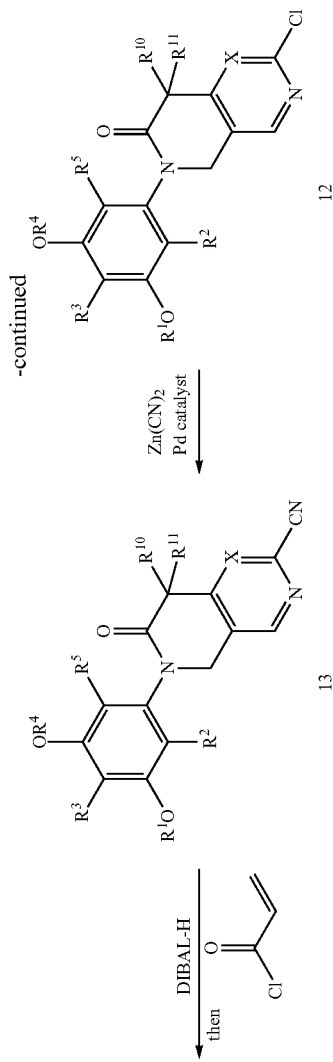

Alkene 17 can be synthesized following the procedure shown in Scheme 4. Therefore, compound 9 is first treated with triphosgene in the presence of a base such as pyridine, and then with amine R⁷NH₂ in the presence of another base (e.g. DIPEA) to afford urea 15. Upon treatment with a proper base (e.g. Cs₂CO₃), cyclization of 15 takes place to generate cyclic urea 16, which can then be converted to compound 17 using standard Suzuki conditions in the presence of 4,4,5,5-tetramethyl-2-vinyl-1,3,2-dioxaborolane.

Alkene 17 can be prepared by an alternative procedure outlined in scheme 5. The Suzuki coupling between compound 9 and 4,4,5,5-tetramethyl-2-vinyl-1,3,2-dioxaborolane can provide alkene 18, which can be converted to the corresponding amine 19 under standard Buchwald-Hartwig amination conditions using reagents such as, for example, Pd(OAc)₂/Xantphos/Cs₂CO₃ or Pd₂(dba)₃/BINAP/NaOtBu, etc. Treatment of amine 19 with triphosgene in the presence of a base such as Et₃N or DIPEA can afford compound 17.

Scheme 4

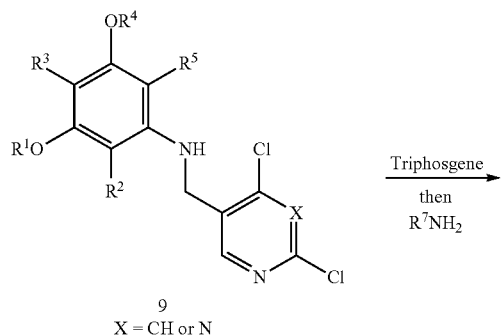
9
X = CH or N

Triphosgene then R⁷NH₂

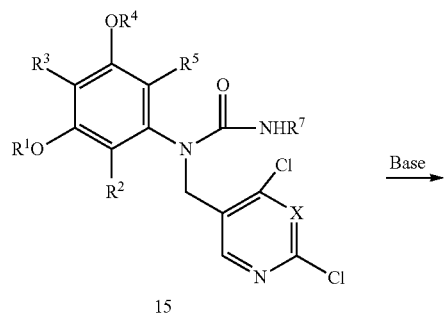
15

Base

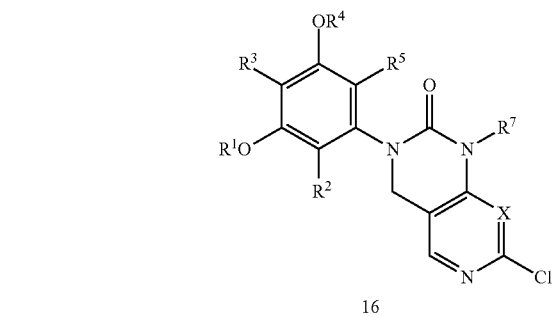
16

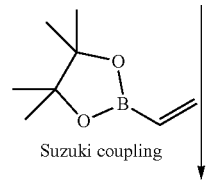
Suzuki coupling

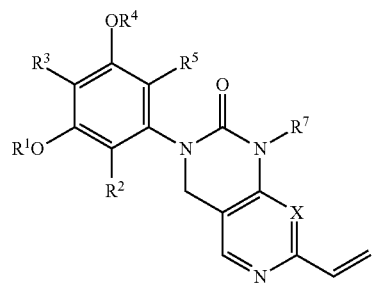
17

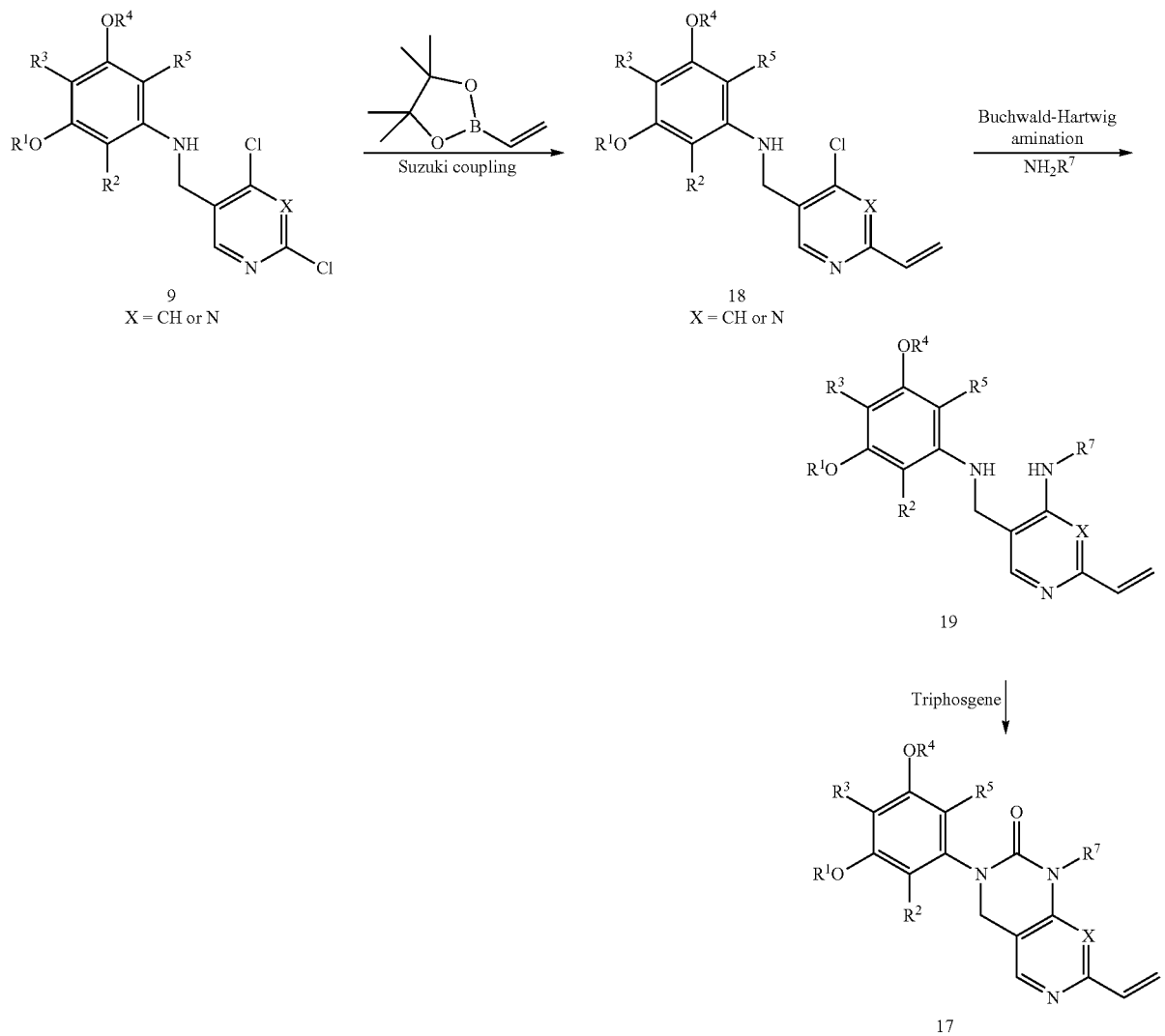
Compound 23 can be synthesized by the method described in Scheme 6. The oxidative cleavage of the alkene 17 using OsO$_4$/NaIO$_4$ can provide aldehyde 20. Compound 20 is then converted to the corresponding amine 21 via reductive amination. The coupling reaction between amine 21 and acid chloride 22 can occur in the presence of a base, such as iPr$_2$NEt or Et$_3$N to afford amide 23.
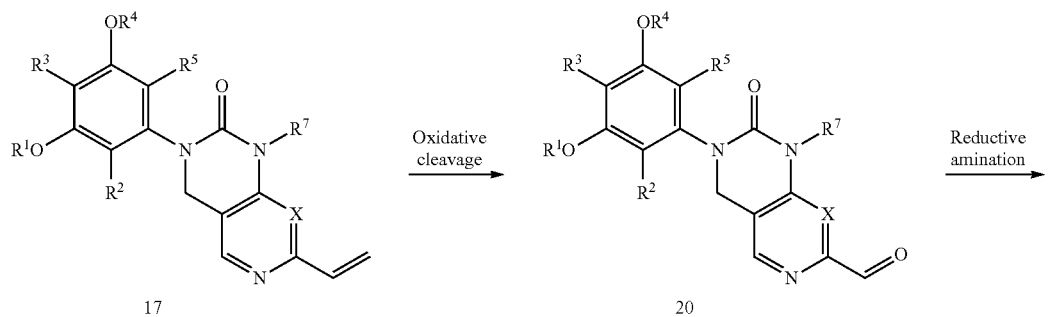

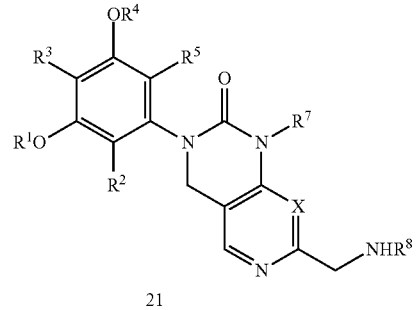

21

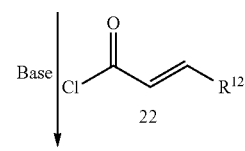

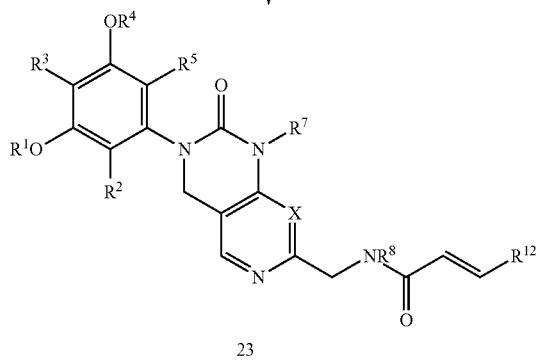

23

Methods of Use

Compounds of the invention can inhibit the activity of the FGFR4 enzyme. For example, the compounds of the invention can be used to inhibit activity of an FGFR4 enzyme in a cell or in an individual or patient in need of inhibition of the enzyme by administering an inhibiting amount of a compound of the invention to the cell, individual, or patient.

In some embodiments, the compounds of the invention are selective for the enzyme FGFR4 over one or more of FGFR1, FGFR2, and/or FGFR3. In some embodiments, the compounds of the invention are selective for the enzyme FGFR4 over FGFR1, FGFR2, and FGFR3. In some embodiments, the compounds of the invention are selective for the enzyme FGFR4 over VEGFR2. In some embodiments, the selectivity is 2-fold or more, 3-fold or more, 5-fold or more, 10-fold or more, 25-fold or more, 50-fold or more, or 100-fold or more.

As FGFR4 inhibitors, the compounds of the invention are useful in the treatment of various diseases associated with abnormal expression or activity of the FGFR4 enzyme or FGFR ligands. Compounds which inhibit FGFR will be useful in providing a means of preventing the growth or inducing apoptosis in tumors, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors.

In certain embodiments, the FGFR4, or a mutant thereof, activity is inhibited irreversibly. In certain embodiments, FGFR4, or a mutant thereof, activity is inhibited irreversibly by covalently modifying Cys 552 of FGFR4.

In certain embodiments, the invention provides a method for treating a FGFR4-mediated disorder in a patient in need thereof, comprising the step of administering to said patient a compound according to the invention, or a pharmaceutically acceptable composition thereof.

For example, the compounds of the invention are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the invention include tumors of the eye, glioblastoma, melanoma, rhabdosarcoma, lymphosarcoma, and osteosarcoma.

The compounds of the invention can also be useful in the inhibition of tumor metastisis.

In some embodiments, the present invention provides a method for treating hepatocellular carcinoma in a patient in need thereof, comprising the step of administering to said patient a compound according to the invention, or a pharmaceutically acceptable composition thereof.

In some embodiments, the present invention provides a method for treating Rhabdomyosarcoma, esophageal cancer, breast cancer, or cancer of a head or neck, in a patient in need thereof, comprising the step of administering to said patient a compound according to the invention, or a pharmaceutically acceptable composition thereof.

In some embodiments, the present invention provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR4 enzyme with a compound of the invention includes the administration of a compound of the present invention to an individual or patient, such as a human, having FGFR, as well as, for example, introducing a compound of the invention into a sample containing a cellular or purified preparation containing the FGFR4 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 2) inhibiting the disease; for example, inhibiting a disease, condition or disorder in an individual who is experiencing or displaying the pathology or symptomatology of the disease, condition or disorder (i.e., arresting further development of the pathology and/or symptomatology), or 3) ameliorating the disease; for example, ameliorating a disease, condition or disorder in an individual who is experiencing or displaying the pathology or symptomatology of the disease, condition or disorder (i.e., reversing the pathology and/or symptomatology).

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of the present invention for treatment of FGFR-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with compounds of the present invention. In some embodiments, the JAK inhibitor is selective for JAK1 over JAK2 and JAK3.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-$\beta$, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.
Labeled Compounds and Assay Methods Another aspect of the present invention relates to fluorescent dye, spin label, heavy metal or radio-labeled compounds of the invention that would be useful not only in imaging but also in assays, both in vitro and in vivo, for localizing and quantitating the FGFR enzyme in tissue samples, including human, and for identifying FGFR enzyme ligands by inhibition binding of a labeled compound. Accordingly, the present invention includes FGFR enzyme assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{2}H$ (also written as D for deuterium), $^{3}H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro FGFR enzyme labeling and competition assays, compounds that incorporate $^{3}H$, $^{14}C$, $^{82}Br$, $^{125}I$, $^{131}I$, or $^{35}S$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the FGFR4 enzyme. Accordingly, the ability of a test compound to compete with the radio-labeled compound for binding to the FGFR4 enzyme directly correlates to its binding affinity.
Kits The present invention also includes pharmaceutical kits useful, for example, in the treatment or prevention of FGFR-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more FGFR's as described below.

EXAMPLES

Experimental procedures for compounds of the invention are provided below. All the starting materials are commercially available or readily synthezied according to procedures known in the art. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide

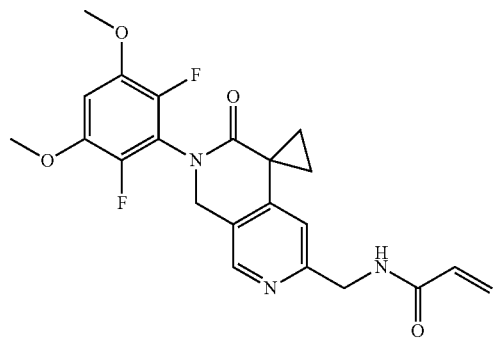 [SMILES: C=CC(=O)NCc1cc2c(cn1)CN(c1c(F)c(OC)cc(OC)c1F)C(=O)C21CC1]

Step 1: 4,6-dichloronicotinaldehyde

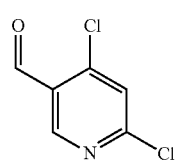

To a stirred solution of 2,4-dichloro-5-carbethoxypyridine (10.0 g, 45.4 mmol) in methylene chloride (100.0 mL), diisobutylaluminum hydride in methylene chloride (50.0 mL, 1.0 M, 50.0 mmol) was added dropwise at −78° C. After 2 hours, the reaction was quenched with a saturated solution of Rochelle's salt. After stirring for 12 hours, the aqueous solution was extracted with DCM (3×150 mL). The combined organic layers were dried over $Na_2SO_4$ and concentrated in vacuo to afford the crude aldehyde (7.51 g, 42.9 mmol), which was used directly in the next step without further purification. LC-MS calculated for $C_6H_4Cl_2NO$ $[M+H]^+$ m/z: 176.0; found 176.0.

Step 2: N-[(4,6-dichloropyridin-3-yl)methyl]-2,6-difluoro-3,5-dimethoxyaniline

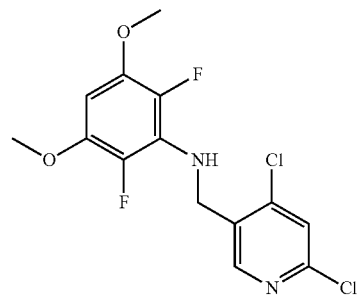 [SMILES: COc1cc(OC)c(F)c(NCc2cnc(Cl)cc2Cl)c1F]

To a stirred solution of 2,6-difluoro-3,5-dimethoxyaniline (9.03 g, 47.7 mmol), sodium triacetoxyborohydride (38.0 g, 180 mmol) in methylene chloride (60 mL)/trifluoroacetic acid (30 mL), 4,6-dichloronicotinaldehyde (8.00 g, 45.5 mmol) was added in small portions at room temperature. After 1 hour, the volatiles were removed in vacuo and saturated aqueous $NaHCO_3$ (200 mL) was added. The resulting mixture was extracted with DCM (3×150 mL). The organic layers were combined, dried over $Na_2SO_4$, and concentrated. The residue was purified on silica gel (eluting with 0 to 0-40% EtOAc in hexanes) to afford the desired product (15.0 g). LC-MS calculated for $C_{14}H_{13}Cl_2F_2N_2O_2$ $[M+H]^+$ m/z: 349.0; found 349.1.

Step 3: ethyl 3-[[(4,6-dichloropyridin-3-yl)methyl] (2,6-difluoro-3,5-dimethoxyphenyl)amino]-3-oxo-propanoate

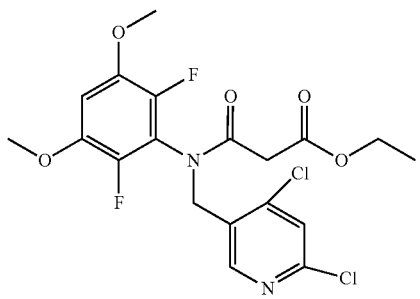 [SMILES: CCOC(=O)CC(=O)N(Cc1cnc(Cl)cc1Cl)c1c(F)c(OC)cc(OC)c1F]

To a stirred solution of N-[(4,6-dichloropyridin-3-yl) methyl]-2,6-difluoro-3,5-dimethoxyaniline (3.50 g, 10.0. mmol) in tetrahydrofuran (20 mL), NaH (60% w/w in mineral oil, 421 mg, 10.5 mmol) was added at room temperature. After 10 minutes, ethyl malonyl chloride (1.92 mL, 15.0 mmol) was added dropwise. After another 1 hour, the reaction was quenched with saturated aqueous $NH_4Cl$, and extracted with DCM (3×100 mL). The organic layers were combined, dried over $Na_2SO_4$, and concentrated. The resi- Step 4: Ethyl 6-chloro-2-(2,6-difluoro-3,5-dimethoxyphenyl)-3-oxo-1,2,3,4-tetrahydro-2,7-naphthyridine-4-carboxylate

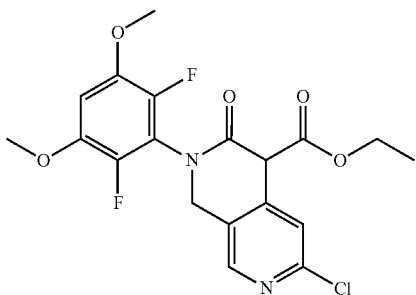 [SMILES: CCOC(=O)C1C(=O)N(c2c(F)c(OC)cc(OC)c2F)Cc2cnc(Cl)cc21]

To a stirred solution of ethyl 3-[[(4,6-dichloropyridin-3-yl)methyl](2,6-difluoro-3,5-dimethoxyphenyl)amino]-3-oxopropanoate (1.50 g, 3.24 mmol) in DMF (15 mL), NaH (60% w/w in mineral oil, 337 mg, 8.42 mmol) was added at room temperature. The resulting mixture was then warmed up to 110° C. After 5 hours, the reaction was cooled to room temperature, saturated aqueous NH$_4$Cl (50 mL) was added to form precipitate. After filtration, the solid was dried in vacuo to give crude cyclized product (0.95 g, 2.23 mmol). LC-MS calculated for C$_{19}$H$_{18}$ClF$_2$N$_2$O$_5$ [M+H]$^+$ m/z: 427.1; found 427.0.

Step 5: 6-chloro-2-(2,6-difluoro-3,5-dimethoxyphenyl)-1,2-dihydro-2,7-naphthyridin-3(4H)-one

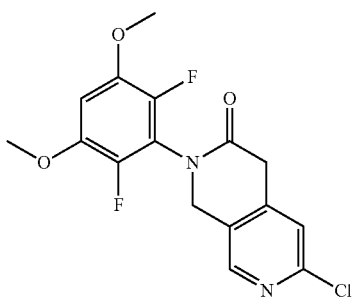 [SMILES: COc1cc(OC)c(F)c(N2Cc3cnc(Cl)cc3CC2=O)c1F]

To a stirred solution of ethyl 6-chloro-2-(2,6-difluoro-3,5-dimethoxyphenyl)-3-oxo-1,2,3,4-tetrahydro-2,7-naphthyridine-4-carboxylate (0.95 g, 2.23 mmol) in 1,4-dioxane (5 mL) hydrogen chloride (4.0 M in dioxane, 2 mL, 8 mmol) was added at room temperature. The resulting mixture was warmed up to 100° C. After 4 hours, the reaction was cooled to ambient temperature, quenched with saturated aqueous NaHCO$_3$, and extracted with DCM (3×100 mL). The organic layers were combined, dried over Na$_2$SO$_4$, and concentrated. The residue was purified on silica gel (eluting with 0 to 0-30% EtOAc in DCM) to afford the desired product (0.75 g, 2.12 mmol). LC-MS calculated for C$_{16}$H$_{14}$ClF$_2$N$_2$O$_3$ [M+H]$^+$ m/z: 355.1; found 355.1.

Step 6: 6'-chloro-2'-(2,6-difluoro-3,5-dimethoxyphenyl)-1',2'-dihydro-3'H-spiro[cyclopropane-1,4'-[2,7]naphthyridin]-3'-one

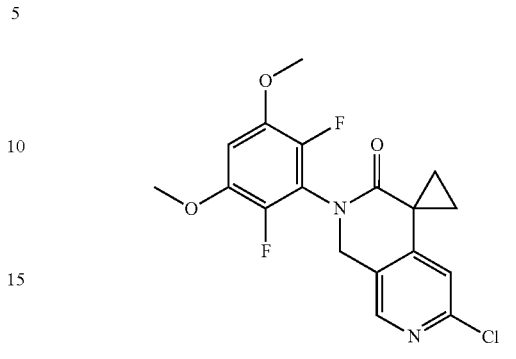

To a stirred solution of 6-chloro-2-(2,6-difluoro-3,5-dimethoxyphenyl)-1,4-dihydro-2,7-naphthyridin-3(2H)-one (1.50 g, 4.23 mmol) in DMF (10 mL), cesium carbonate (3.03 g, 9.30 mmol) and 1-bromo-2-chloro-ethane (701 μL, 8.46 mmol) were added sequentially at room temperature. After 5 hours, the reaction was quenched with saturated aqueous NH$_4$Cl, and extracted with DCM (3×75 mL). The organic layers were combined, dried over Na$_2$SO$_4$, and concentrated. The residue was purified on silica gel (eluting with 0 to 0-50% EtOAc in hexanes) to afford the desired product (1.20 g, 3.15 mmol). LC-MS calculated for C$_{18}$H$_{16}$ClF$_2$N$_2$O$_3$ [M+H]$^+$ m/z: 381.1; found 381.1.

Step 7: 2'-(2,6-difluoro-3,5-dimethoxyphenyl)-3'-oxo-2',3'-dihydro-1'H-spiro[cyclopropane-1,4'-[2,7]naphthyridine]-6'-carbonitrile

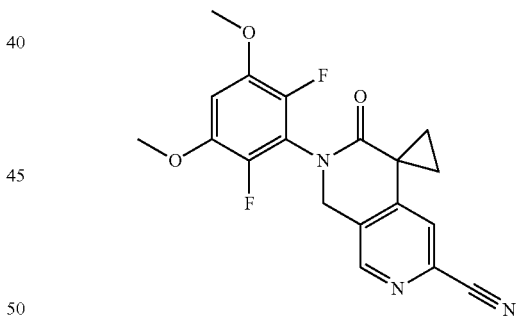

A reaction mixture of 6'-chloro-2'-(2,6-difluoro-3,5-dimethoxyphenyl)-1',2'-dihydro-3'H-spiro[cyclopropane-1,4'-[2,7]naphthyridin]-3'-one (0.40 g, 1.0 mmol), zinc cyanide (0.12 g, 1.0 mmol) and [1,1'-bis(diphenylphosphino)ferrocene]dichloropalladium(II) complexed with dichloromethane (1:1) (86 mg, 0.10 mmol) in N,N-dimethylformamide (6.9 mL) was stirred at 130° C. under an atmosphere of N$_2$ for 6 hours. The reaction was quenched with saturated aqueous NaHCO$_3$, and extracted with ethyl acetate (3×20 mL). The combined organic layers were washed with brine, dried over MgSO$_4$, filtered and concentrated under reduced pressure. The residue was purified on silica gel (eluting with 0 to 0-20% EtOAc in DCM) to afford the desired product (0.28 g). LC-MS calculated for C$_{19}$H$_{16}$F$_2$N$_3$O$_3$[M+H]$^+$ m/z: 372.1; found 372.1.

Step 8: 6'-(aminomethyl)-2'-(2,6-difluoro-3,5-dimethoxyphenyl)-1',2'-dihydro-3'H-spiro[cyclopropane-1,4'-[2,7]naphthyridin]-3'-one

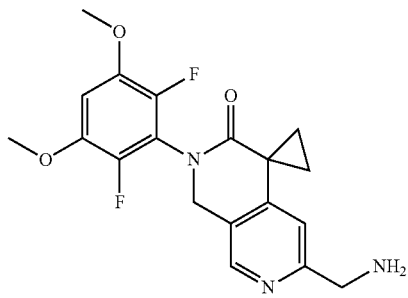 [SMILES: COc1cc(OC)c(F)c(N2Cc3cnc(CN)cc3C3(CC3)C2=O)c1F]

To a stirred solution of 2'-(2,6-difluoro-3,5-dimethoxyphenyl)-3'-oxo-2',3'-dihydro-1'H-spiro[cyclopropane-1,4'-[2,7]naphthyridine]-6'-carbonitrile (99.9 mg, 0.269 mmol) in THF (5 mL), diisobutylaluminum hydride (1.0 M in toluene, 0.54 mL, 0.54 mmol) was added at −78° C. After 2 hours, the reaction mixture was quenched with saturated aqueous NH$_4$Cl, and extracted with ethyl acetate (3×20 mL). The combined organic layers were washed with brine, dried over MgSO4, filtered and concentrated under reduced pressure. The residue was purified on prep-HPLC (pH=2, acetonitrile/water+TFA) to give the desired product (15 mg) as its TFA salt. LC-MS calculated for $C_{19}H_{20}F_2N_3O_3$[M+H]$^+$ m/z: 376.2; found 376.1.

Step 9: N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide To a stirred solution of 6'-(aminomethyl)-2'-(2,6-difluoro-3,5-dimethoxyphenyl)-1',2'-dihydro-3'H-spiro[cyclopropane-1,4'-[2,7]naphthyridin]-3'-one (25.5 mg, 0.068 mmol) in methylene chloride (4.0 mL), N,N-diisopropylethylamine (46 μL, 0.27 mmol) and 2-propenoyl chloride (5.8 μL, 0.072 mmol) were added sequentially at room temperature. After 3 minutes, the reaction was quenched with saturated aqueous NH$_4$Cl, extracted with methylene chloride. The combined organic layers were dried over Na$_2$SO$_4$, filtered, and concentrated to dryness under reduced pressure. The crude product was purified on prep-HPLC (pH=2, acetonitrile/water+TFA) to give the desired product (15 mg) as its TFA salt. LCMS calculated for $C_{22}H_{22}F_2N_3O_4$ [M+H]$^+$ m/z: 430.2; Found: 430.1. $^1$H NMR (500 MHz, DMSO-d$_6$): δ 8.63 (t, J=5.6 Hz, 1H), 8.40 (s, 1H), 7.07 (t, J=8.2 Hz, 1H), 6.97 (s, 1H), 6.31 (dd, J=17.1, 10.2 Hz, 1H), 6.11 (dd, J=17.1, 2.1 Hz, 1H), 5.62 (dd, J=10.2, 2.1 Hz, 1H), 4.95 (s, 2H), 4.43 (d, J=5.8 Hz, 2H), 3.89 (s, 6H), 1.76 (q, J=3.9 Hz, 2H), 1.46 (q, J=4.0 Hz, 2H).

Example 2

N-((3-(2,6-difluoro-3,5-dimethoxyphenyl)-1-ethyl-2-oxo-1,2,3,4-tetrahydropyrido[4,3-d]pyrimidin-7-yl)methyl)acrylamide

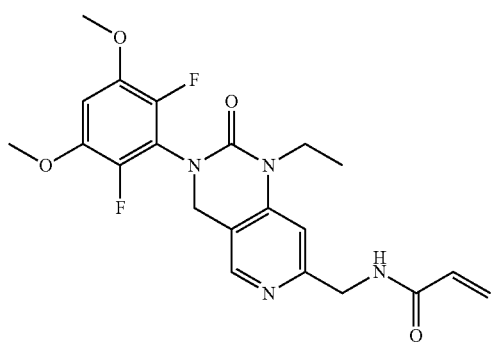 [SMILES: C=CC(=O)NCc1cc2c(cn1)CN(c1c(F)c(OC)cc(OC)c1F)C(=O)N2CC]

Step 1: 7-chloro-3-(2,6-difluoro-3,5-dimethoxyphenyl)-1-ethyl-3,4-dihydropyrido[4,3-d]pyrimidin-2(1H)-one

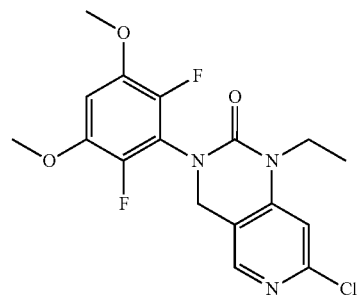 [SMILES: CCN1C(=O)N(c2c(F)c(OC)cc(OC)c2F)Cc2cnc(Cl)cc21]

To a solution of triphosgene (344 mg, 1.16 mmol) in CH$_2$Cl$_2$ (12 mL, 190 mmol) at 0° C. was first added pyridine (0.250 mL, 3.09 mmol). The reaction mixture was then stirred at 0° C. for 10 minutes, followed by the addition of a solution of N-[(4,6-dichloropyridin-3-yl)methyl]-2,6-difluoro-3,5-dimethoxyaniline (prepared as in Example 1, Step 2, 900 mg, 2.58 mmol) in CH$_2$Cl$_2$ (8.0 mL). The reaction mixture was stirred at 0° C. for 1 hour, after which time ethylamine in THF (2.0 M, 6.4 mL, 13 mmol) was added to the reaction mixture, followed by the addition of N,N-diisopropylethylamine (920 μL, 5.3 mmol). The resulting mixture was then warmed to room temperature, stirred overnight, quenched with saturated NaHCO$_3$ (aqueous solution), and extracted with EtOAc (3×20 mL). The combined organic layers were dried over Na$_2$SO$_4$ and concentrated to give the crude intermediate 1-((4,6-dichloropyridin-3-yl)methyl)-1-(2,6-difluoro-3,5-dimethoxyphenyl)-3-ethylurea. The crude intermediate was first dissolved in DMF (20 mL), followed by the addition of Cs$_2$CO$_3$ (1.70 g, 5.2 mmol). The reaction mixture was then stirred at 95° C. for 5 hours until completion, cooled to room temperature, quenched with water, and extracted with EtOAc (3×20 mL). The combined organic layers were dried over Na$_2$SO$_4$, and concentrated. The resulting material was purified via column chromatography (25% to 55% EtOAc in hexanes) to give the product as a slightly yellow solid. LC-MS calculated for $C_{17}H_{17}ClF_2N_3O_3$ [M+H]$^+$ m/z: 384.1; found 384.1.

Step 2: 3-(2,6-difluoro-3,5-dimethoxyphenyl)-1-ethyl-7-vinyl-3,4-dihydropyrido[4,3-d]pyrimidin-2(1H)-one

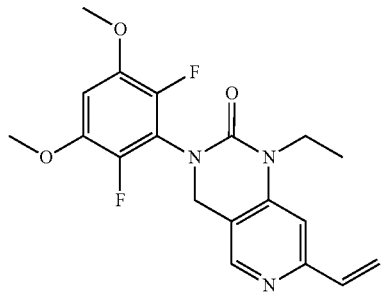 [SMILES: C=Cc1cc2c(cn1)CN(c1c(F)c(OC)cc(OC)c1F)C(=O)N2CC]

A mixture of 7-chloro-3-(2,6-difluoro-3,5-dimethoxyphenyl)-1-ethyl-3,4-dihydropyrido[4,3-d]pyrimidin-2(1H)-one (460 mg, 1.20 mmol), 4,4,5,5-tetramethyl-2-vinyl-1,3,2-dioxaborolane (240 µL, 1.4 mmol), tetrakis(triphenylphosphine)palladium(0) (0.08 g, 0.07 mmol) and potassium carbonate (0.66 g, 4.8 mmol) in 1,4-dioxane (12 mL) and water (4.3 mL) was stirred at 120° C. overnight. The reaction was quenched with saturated aqueous NaHCO$_3$, and extracted with ethyl acetate (3×20 mL). The combined organic layers were washed with brine, dried over MgSO$_4$, filtered and concentrated under reduced pressure. The residue was purified on silica gel (eluting with 0 to 0-40% EtOAc in hexanes) to afford the desired product. LC-MS calculated for $C_{19}H_{20}F_2N_3O_3$ [M+H]$^+$ m/z: 376.1; found 376.1.

Step 3: 3-(2,6-difluoro-3,5-dimethoxyphenyl)-1-ethyl-2-oxo-1,2,3,4-tetrahydropyrido[4,3-d]pyrimidine-7-carbaldehyde

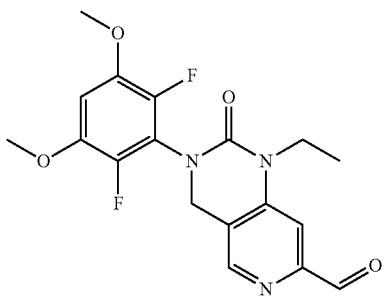 [SMILES: CCN1C(=O)N(c2c(F)c(OC)cc(OC)c2F)Cc2cnc(C=O)cc21]

To a solution of 3-(2,6-difluoro-3,5-dimethoxyphenyl)-1-ethyl-7-vinyl-3,4-dihydropyrido[4,3-d]pyrimidin-2(1H)-one (0.32 g, 0.85 mmol) in 1,4-dioxane (10 mL) and water (5 mL) was added osmium tetraoxide (0.81 mL, 4% w/w, 0.13 mmol) at room temperature. The reaction mixture was stirred for 5 minutes then sodium periodate (0.547 g, 2.56 mmol) was added. The reaction mixture was stirred at room temperature for 1 hour, then diluted with water and extracted with EtOAc. The combined extracts were washed with water and brine, dried over MgSO$_4$, filtered and concentrated under reduced pressure. The residue was used in the next step without further purification.

Step 4: (E)-3-(2,6-difluoro-3,5-dimethoxyphenyl)-1-ethyl-2-oxo-1,2,3,4-tetrahydropyrido[4,3-d]pyrimidine-7-carbaldehyde Oxime

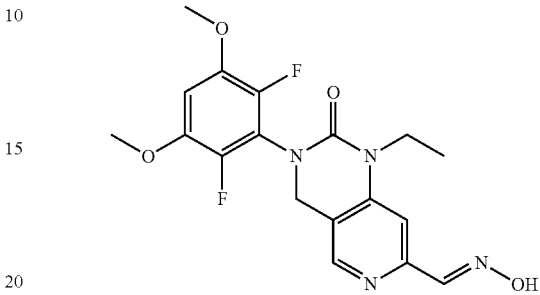

Hydroxylamine hydrochloride (0.21 g, 3.0 mmol) was added to a slurry of crude 3-(2,6-difluoro-3,5-dimethoxyphenyl)-1-ethyl-2-oxo-1,2,3,4-tetrahydropyrido[4,3-d]pyrimidine-7-carbaldehyde (0.31 g, 0.80 mmol) and potassium carbonate (0.12 g, 0.85 mmol) in methanol (6 mL) at room temperature. The resulting mixture was stirred at 70° C. for 1 hour. The volatiles were removed and the residue was diluted with ethyl acetate (20 mL). The organic layer was washed with saturated aqueous NaHCO$_3$ solution, brine, dried over MgSO$_4$, filtered and concentrated under reduced pressure. The crude product was used directly in the next step. LC-MS calculated for $C_{18}H_{19}F_2N_4O_4$ [M+H]$^+$ m/z: 393.1; found 393.1.

Step 5. 7-(aminomethyl)-3-(2,6-difluoro-3,5-dimethoxyphenyl)-1-ethyl-3,4-dihydropyrido[4,3-d]pyrimidin-2(1H)-one

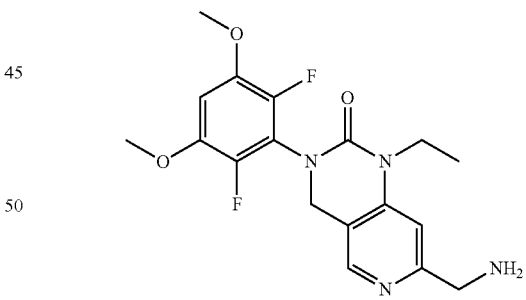

Zinc (440 mg, 6.8 mmol) was added in several portions to a solution of crude (E)-3-(2,6-difluoro-3,5-dimethoxyphenyl)-1-ethyl-2-oxo-1,2,3,4-tetrahydropyrido[4,3-d]pyrimidine-7-carbaldehyde oxime (0.30 g, 0.76 mmol) in acetic acid (3 mL) at room temperature. The resulting reaction mixture was stirred at room temperature for 1 hour. The reaction was quenched with saturated aqueous NaHCO$_3$, and extracted with ethyl acetate (3×20 mL). The combined organic layers were washed with brine, dried over MgSO$_4$, filtered and concentrated under reduced pressure. Hydrogen chloride (0.54 mL, 4.0 M in 1,4-dioxane, 2.2 mmol) was added to the residue. The mixture was concentrated in vacuo to afford the crude product (0.30 g) as its HCl salt. LC-MS calculated for $C_{18}H_{21}F_2N_4O_3$ [M+H]$^+$ m/z: 379.2; found 379.1.

Step 6: N-((3-(2,6-difluoro-3,5-dimethoxyphenyl)-1-ethyl-2-oxo-1,2,3,4-tetrahydropyrido[4,3-d]pyrimidin-7-yl)methyl) acrylamide To a stirred solution of crude 7-(aminomethyl)-3-(2,6-difluoro-3,5-dimethoxyphenyl)-1-ethyl-3,4-dihydropyrido[4,3-d]pyrimidin-2(1H)-one (0.28, 0.74 mmol) and triethylamine (350 µL, 2.5 mmol) in acetonitrile (5 mL), 2-propenoyl chloride (70 µL, 0.86 mmol) was added at room temperature. After 30 minutes, the reaction mixture was diluted with MeOH and was purified by RP-HPLC (pH=2) to afford the desired product as its TFA salt. LC-MS calculated for $C_{21}H_{23}F_2N_4O_4$ [M+H]$^+$ m/z: 433.2; found 433.1. $^1$H NMR (500 MHz, DMSO-$d_6$): δ 8.87 (s, 1H), 8.38 (s, 1H), 7.33 (s, 1H), 7.08 (t, J=8.2 Hz, 1H), 6.32 (dd, J=17.1, 10.2 Hz, 1H), 6.15 (dd, J=17.1, 2.0 Hz, 1H), 5.68 (dd, J=10.2, 2.0 Hz, 1H), 4.84 (s, 2H), 4.57 (d, J=5.6 Hz, 2H), 3.92 (q, J=5.0 Hz, 2H), 3.89 (s, 6H), 1.18 (t, J=7.0 Hz, 3H).

Example 3

N-((3-(2,6-difluoro-3,5-dimethoxyphenyl)-2-oxo-1-(pyridin-3-yl)-1,2,3,4-tetrahydropyrido[4,3-d]pyrimidin-7-yl)methyl)acrylamide

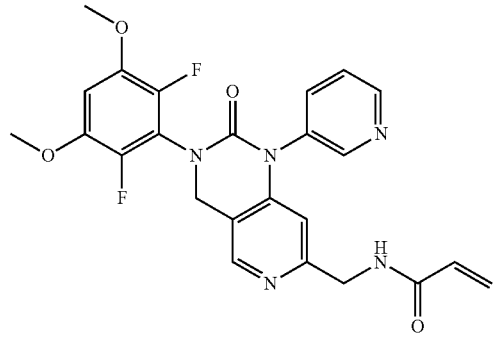 [SMILES: C=CC(=O)NCc1cc2c(cn1)CN(c1c(F)c(OC)cc(OC)c1F)C(=O)N2c1cccnc1]

Step 1: N-((4-chloro-6-vinylpyridin-3-yl)methyl)-2,6-difluoro-3,5-dimethoxyaniline

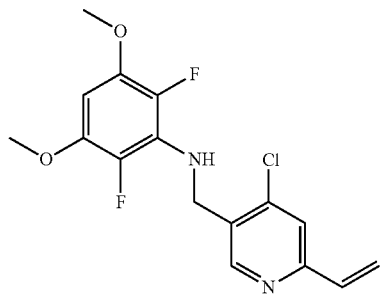 [SMILES: C=Cc1cc(Cl)c(CNc2c(F)c(OC)cc(OC)c2F)cn1]

A mixture of N-[(4,6-dichloropyridin-3-yl)methyl]-2,6-difluoro-3,5-dimethoxyaniline (prepared as in Example 1, Step 2, 2.00 g, 5.73 mmol), 4,4,5,5-tetramethyl-2-vinyl-1,3,2-dioxaborolane (0.98 mL, 5.8 mmol), tetrakis(triphenylphosphine)palladium(0) (0.4 g, 0.3 mmol) and potassium carbonate (3.2 g, 23 mmol) in 1,4-dioxane (10 mL) and water (2.0. mL) was stirred at 120° C. overnight. The reaction mixture was quenched with saturated aqueous NaHCO$_3$, and extracted with ethyl acetate (3×100 mL). The combined organic layers were washed with brine, dried over MgSO$_4$, filtered and concentrated under reduced pressure. The residue was purified on silica gel (eluting with 0 to 0-25% EtOAc in hexanes) to afford the desired product (1.3 g). LC-MS calculated for $C_{16}H_{16}ClF_2N_2O_2$ [M+H]$^+$ m/z: 341.1; found 341.1.

Step 2: 3-(2,6-difluoro-3,5-dimethoxyphenyl)-1-(pyridin-3-yl)-7-vinyl-3,4-dihydropyrido[4,3-d]pyrimidin-2(1H)-one

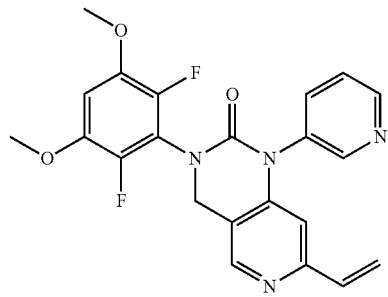 [SMILES: C=Cc1cc2c(cn1)CN(c1c(F)c(OC)cc(OC)c1F)C(=O)N2c1cccnc1]

To a stirred solution of N-[(4-chloro-6-vinylpyridin-3-yl)methyl]-2,6-difluoro-3,5-dimethoxyaniline (100.0 mg, 0.2935 mmol), palladium acetate (6.6 mg, 0.029 mmol), (R)-(+)-2,2'-bis(diphenylphosphino)-1,1'-binaphthyl (18 mg, 0.029 mmol), and cesium carbonate (290 mg, 0.89 mmol) in 1,4-dioxane (6 mL, 80 mmol) was added 3-pyridinamine (39 mg, 0.41 mmol). The resulting mixture was stirred at 130° C. overnight under the atmosphere of N$_2$. After cooling to room temperature, the reaction mixture was diluted with ethyl acetate, filtered and concentrated under reduced pressure. The crude N-(5-(((2,6-difluoro-3,5-dimethoxyphenyl)amino)methyl)-2-vinylpyridin-4-yl)pyridin-3-amine was used without further purification. LC-MS calculated for $C_{21}H_{21}F_2N_4O_2$ [M+H]$^+$ m/z: 399.2; found 399.2.

Triphosgene (87 mg, 0.29 mmol) was added to a solution of the crude N-(5-(((2,6-difluoro-3,5-dimethoxyphenyl)amino)methyl)-2-vinylpyridin-4-yl)pyridin-3-amine and N,N-diisopropylethylamine (310 µL, 1.8 mmol) in tetrahydrofuran (5 mL) at 0° C. After 15 minutes, the reaction was quenched with saturated aqeuous NaHCO$_3$, diluted with EtOAc. The organic layer was separated and washed with water, dried over Na$_2$SO$_4$, filtered and concentrated in vacuo to afford the desired product, which was used directly in the next step without further purification. LC-MS calculated for $C_{22}H_{19}F_2N_4O_3$ [M+H]$^+$ m/z: 425.2; found 425.2.

Step 3: N-((3-(2,6-difluoro-3,5-dimethoxyphenyl)-2-oxo-1-(pyridin-3-yl)-1,2,3,4-tetrahydropyrido[4,3-d]pyrimidin-7-yl)methyl)acrylamide The title compound was prepared using procedures analogous to those described for Example 2, Steps 3 to 6, with 3-(2,6-difluoro-3,5-dimethoxyphenyl)-1-(pyridin-3-yl)-7-vinyl-3,4-dihydropyrido[4,3-d]pyrimidin-2(1H)-one replacing 3-(2,6-difluoro-3,5-dimethoxyphenyl)-1-ethyl-7-vinyl- 3,4-dihydropyrido[4,3-d]pyrimidin-2(1H)-one in step 3. LCMS calculated for $C_{24}H_{22}F_2N_5O_4$ [M+H]$^+$ m/z: 482.2; Found: 482.2.

Example 4

N-((6'-(2,6-difluoro-3,5-dimethoxyphenyl)-7'-oxo-6', 7'-dihydro-5'H-spiro[cyclopropane-1,8'-pyrido[4,3-d]pyrimidine]-2'-yl)methyl)acrylamide

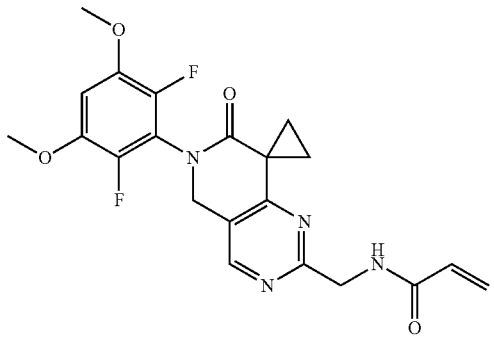 [SMILES: C=CC(=O)NCc1ncc2c(n1)C1(CC1)C(=O)N(c1c(F)c(OC)cc(OC)c1F)C2]

Step 1: 2,4-dichloro-5-(chloromethyl)pyrimidine

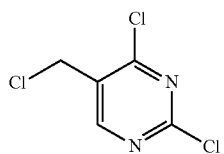

To a stirred solution of 5-(hydroxymethyl)uracil (5.0 g, 35 mmol) in phosphoryl chloride (25 mL, 270 mmol) and toluene (6.0 mL), N,N-diisopropylethylamine (26 mL, 150 mmol) was added dropwise at room temperature. The resulting solution was heated at 110° C. overnight. After being cooled to room temperature, the reaction mixture was concentrated under reduced pressure, diluted with 1N HCl (100 mL) and water (200 mL), and was extracted with DCM. The organic layers were combined, dried over Na$_2$SO$_4$, filtered and concentrated. The residue was purified on silica gel (eluting with 0-40% EtOAc in DCM) to give 6.4 g of the desired product. LCMS calculated for $C_5H_4Cl_3N_2$ [M+H]$^+$ m/z: 196.9; Found: 197.0.

Step 2: 2,4-dichloro-5-(iodomethyl)pyrimidine

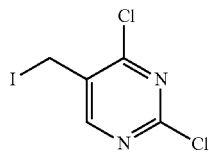

To a stirred solution of 2,4-dichloro-5-(chloromethyl) pyrimidine (1.50 g, 7.60 mmol) in acetone (10 mL), sodium iodide (1.20 g, 7.98 mmol) was added at room temperature. After stirring for 5 hours, the reaction mixture was filtered and the solid was washed with acetone. The filtrate and washed solution were combined and concentrated. The residue was purified on silica gel (eluting with 0-40% EtOAc in hexanes) to give 1.5 g of the desired product. LCMS calculated for $C_5H_4Cl_2IN_2$ [M+H]$^+$ m/z: 288.9; Found: 288.8.

Step 3: N-[(2,4-dichloropyrimidin-5-yl)methyl]-2,6-difluoro-3,5-dimethoxyaniline

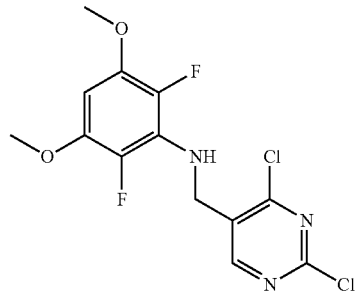 [SMILES: COc1cc(OC)c(F)c(NCc2cnc(Cl)nc2Cl)c1F]

A mixture of 2,4-dichloro-5-(iodomethyl)pyrimidine (1.50 g, 5.19 mmol), 2,6-difluoro-3,5-dimethoxyaniline (1.08 g, 5.71 mmol) in N,N-diisopropylethylamine (4 mL) was stirred at 80° C. for 2 hours. After being cooled to room temperature, the reaction mixture was concentrated under reduced pressure. The residue was purified on silica gel (eluting with 0-40% EtOAc in DCM) to give 1.70 g of the desired product. LCMS calculated for $C_{13}H_{12}Cl_2F_2N_3O_2$ [M+H]$^+$ m/z: 350.0; Found: 350.0.

Step 4: ethyl 3-(((2,4-dichloropyrimidin-5-yl) methyl)(2,6-difluoro-3,5-dimethoxyphenyl)amino)-3-oxopropanoate

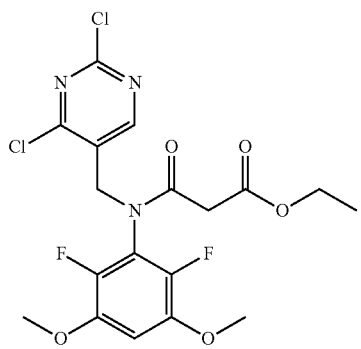 [SMILES: CCOC(=O)CC(=O)N(Cc1cnc(Cl)nc1Cl)c1c(F)c(OC)cc(OC)c1F]

The title compound was prepared using procedures analogous to those described for Example 1, Step 3, with N-[(2, 4-dichloropyrimidin-5-yl)methyl]-2,6-difluoro-3,5-dimethoxyaniline replacing N-[(4,6-dichloropyridin-3-yl) methyl]-2,6-difluoro-3,5-dimethoxyaniline. LCMS calculated $C_{18}H_{18}Cl_2F_2N_3O_5$ [M+H]$^+$ m/z: 464.1; Found: 464.0.

Step 5: ethyl 2-chloro-6-(2,6-difluoro-3,5-dimethoxyphenyl)-7-oxo-5,6,7,8-tetrahydropyrido[4,3-d]pyrimidine-8-carboxylate

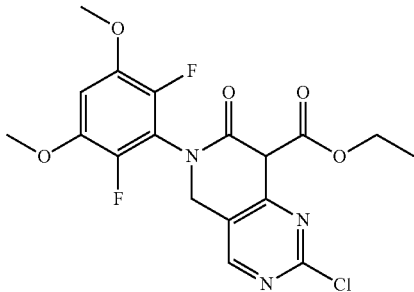 [SMILES: CCOC(=O)C1C(=O)N(c2c(F)c(OC)cc(OC)c2F)Cc2cnc(Cl)nc21]

A mixture of ethyl 3-[[(2,4-dichloropyrimidin-5-yl)methyl](2,6-difluoro-3,5-dimethoxyphenyl)amino]-3-oxopropanoate (1.2 g, 2.6 mmol) and 2-(tert-butylimino)-N,N-diethyl-1,3-dimethyl-1,3,2λ(5)-diazaphosphinan-2-amine (1.5 mL, 5.17 mmol) in methylene chloride (6 mL) was stirred at room temperature for 2 hours. The reaction mixture was concentrated under reduced pressure and the residue was purified on silica gel (eluting with 0-40% EtOAc in DCM) to give 0.88 g of the desired product. LCMS calculated for $C_{18}H_{17}ClF_2N_3O_5$ $[M+H]^+$ m/z: 428.1; Found: 428.0.

Step 6: 2-chloro-6-(2,6-difluoro-3,5-dimethoxyphenyl)-5,8-dihydropyrido[4,3-d]pyrimidin-7(6H)-one

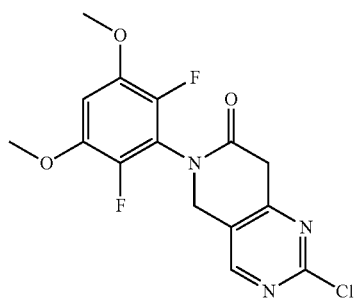 [SMILES: COc1cc(OC)c(F)c(N2Cc3cnc(Cl)nc3CC2=O)c1F]

The title compound was prepared using procedures analogous to those described for Example 1, Step 5, with ethyl 2-chloro-6-(2,6-difluoro-3,5-dimethoxyphenyl)-7-oxo-5,6,7,8-tetrahydropyrido[4,3-d]pyrimidine-8-carboxylate replacing 6-chloro-2-(2,6-difluoro-3,5-dimethoxyphenyl)-3-oxo-1,2,3,4-tetrahydro-2,7-naphthyridine-4-carboxylate. LCMS calculated $C_{15}H_{13}ClF_2N_3O_3$ $[M+H]^+$ m/z: 356.1; Found: 356.1.

Step 7: 2'-chloro-6'-(2,6-difluoro-3,5-dimethoxyphenyl)-5',6'-dihydro-7'H-spiro[cyclopropane-1,8'-pyrido[4,3-d]pyrimidin]-7'-one

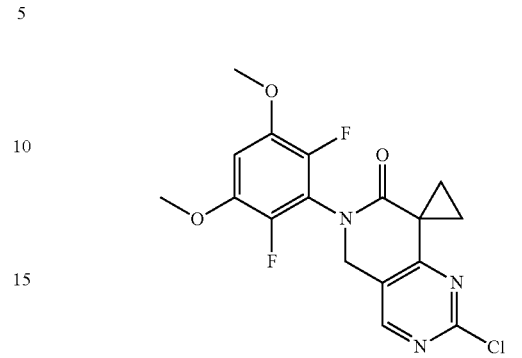

The title compound was prepared using procedures analogous to those described for Example 1, Step 6, with 2-chloro-6-(2,6-difluoro-3,5-dimethoxyphenyl)-5,8-dihydropyrido[4,3-d]pyrimidin-7(6H)-one replacing 6-chloro-2-(2,6-difluoro-3,5-dimethoxyphenyl)-1,4-dihydro-2,7-naphthyridin-3(2H)-one. LCMS calculated $C_{17}H_{15}ClF_2N_3O_3$ $[M+H]^+$ m/z: 382.1; Found: 382.0.

Step 8: N-((6'-(2,6-difluoro-3,5-dimethoxyphenyl)-7'-oxo-6',7'-dihydro-5'H-spiro[cyclopropane-1,8'-pyrido[4,3-d]pyrimidine]-2'-yl)methyl)acrylamide The title compound was prepared using procedures analogous to those described for Example 2, Steps 2 to 6, with 2'-chloro-6'-(2,6-difluoro-3,5-dimethoxyphenyl)-5',6'-dihydro-7'H-spiro[cyclopropane-1,8'-pyrido[4,3-d]pyrimidin]-7'-one replacing 7-chloro-3-(2,6-difluoro-3,5-dimethoxyphenyl)-1-ethyl-3,4-dihydropyrido[4,3-d]pyrimidin-2(1H)-one in step 2. LCMS calculated for $C_{21}H_{21}F_2N_4O_4$ $[M+H]^+$ m/z: 431.2; Found: 431.1.

Example 5

N-((2'-(2,6-difluoro-3,5-dimethoxyphenyl)-3'-oxo-2',3'-dihydro-1'H-spiro[cyclopentane-1,4'-[2,7]naphthyridine]-6'-yl)methyl)acrylamide

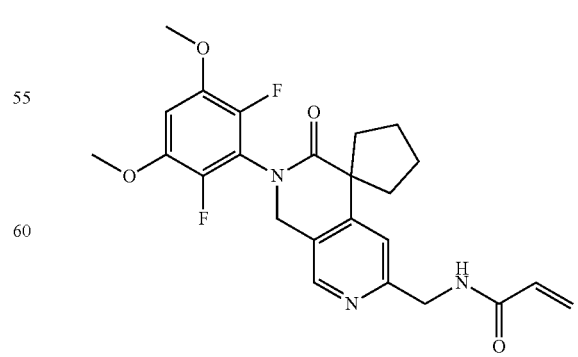

Step 1: 6'-chloro-2'-(2,6-difluoro-3,5-dimethoxyphenyl)-1'H-spiro[cyclopentane-1,4'-[2,7]naphthyridin]-3'(2'H)-one

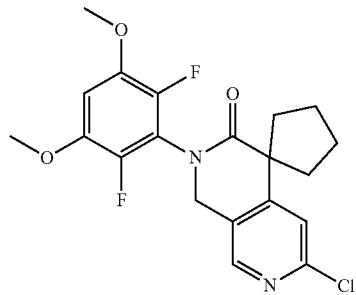 [SMILES: COc1cc(OC)c(F)c(N2Cc3cnc(Cl)cc3C3(CCCC3)C2=O)c1F]

The title compound was prepared using procedures analogous to those described for Example 1, Step 6, with 1,4-dibromobutane replacing 1-bromo-2-chloro-ethane. LCMS calculated for $C_{20}H_{20}ClF_2N_2O_3$ [M+H]$^+$ m/z: 409.1; Found: 409.1.

Step 2: N-((2'-(2,6-difluoro-3,5-dimethoxyphenyl)-3'-oxo-2',3'-dihydro-1'H-spiro[cyclopentane-1,4'-[2,7]naphthyridine]-6'-yl)methyl)acrylamide The title compound was prepared using procedures analogous to those described for Example 2, Steps 2 to 6, with 6'-chloro-2'-(2,6-difluoro-3,5-dimethoxyphenyl)-1'H-spiro[cyclopentane-1,4'-[2,7]naphthyridin]-3'(2'H)-one replacing 7-chloro-3-(2,6-difluoro-3,5-dimethoxyphenyl)-1-ethyl-3,4-dihydropyrido[4,3-d]pyrimidin-2(1H)-one in step 2. LCMS calculated for $C_{24}H_{26}F_2N_3O_4$ [M+H]$^+$ m/z: 458.2; Found: 458.2. $^1$H NMR (600 MHz, DMSO) δ 8.74 (t, J=5.7 Hz, 1H), 8.50 (s, 1H), 7.36 (s, 1H), 7.07 (t, J=8.1 Hz, 1H), 6.34 (dd, J=17.1, 10.3 Hz, 1H), 6.15 (dd, J=17.1, 2.0 Hz, 1H), 5.65 (dd, J=10.3, 2.0 Hz, 1H), 4.87 (s, 2H), 4.51 (d, J=5.9 Hz, 2H), 3.90 (s, 6H), 2.38 (dt, J=14.4, 7.4 Hz, 2H), 1.98 (dt, J=12.3, 6.4 Hz, 2H), 1.87-1.73 (m, 4H).

Example 6

N-((3-(2,6-difluoro-3,5-dimethoxyphenyl)-2-oxo-1-phenyl-1,2,3,4-tetrahydropyrido[4,3-d]pyrimidin-7-yl)methyl)acrylamide

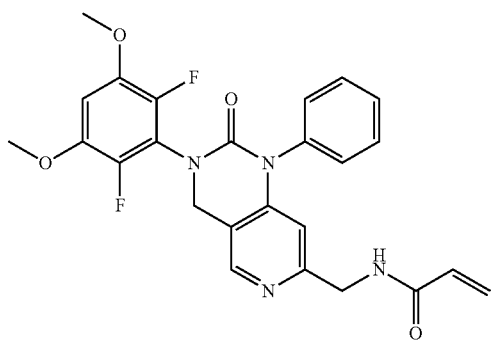

The title compound was prepared using procedures analogous to those described for Example 3, with aniline replacing 3-pyridinamine in Step 2. LCMS calculated for $C_{25}H_{23}F_2N_4O_4$ [M+H]$^+$ m/z: 481.2; Found: 481.2.

Example 7

N-((3-(2,6-difluoro-3,5-dimethoxyphenyl)-1-(1-methyl-1H-pyrazol-3-yl)-2-oxo-1,2,3,4-tetrahydropyrido[4,3-d]pyrimidin-7-yl)methyl)acrylamide

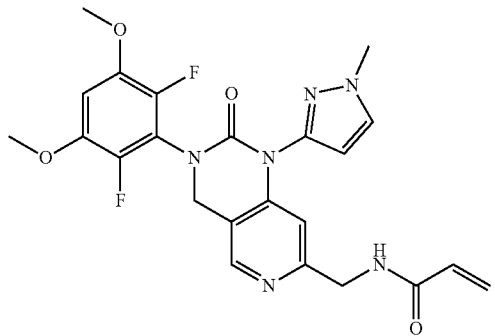 [SMILES: C=CC(=O)NCc1cc2c(cn1)CN(c1c(F)c(OC)cc(OC)c1F)C(=O)N2c1ccn(C)n1]

The title compound was prepared using procedures analogous to those described for Example 3, with 1-methyl-1H-pyrazol-3-amine replacing 3-pyridinamine in Step 2. LCMS calculated for $C_{23}H_{23}F_2N_6O_4$ [M+H]$^+$ m/z: 485.2; Found: 485.2.

Example 8

(S)—N-((3-(2,6-difluoro-3,5-dimethoxyphenyl)-2-oxo-1-(tetrahydrofuran-3-yl)-1,2,3,4-tetrahydropyrido[4,3-d]pyrimidin-7-yl)methyl)acrylamide

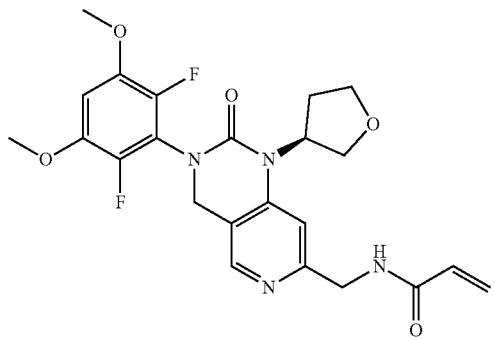 [SMILES: C=CC(=O)NCc1cc2c(cn1)CN(c1c(F)c(OC)cc(OC)c1F)C(=O)N2[C@H]1CCOC1]

The title compound was prepared using procedures analogous to those described for Example 3, with (S)-tetrahydrofuran-3-amine replacing 3-pyridinamine in Step 2. LCMS calculated for $C_{23}H_{25}F_2N_4O_5$ [M+H]$^+$ m/z: 475.2; Found: 475.1.

Example 9

N-((3-(2,6-difluoro-3,5-dimethoxyphenyl)-1-(3,3-difluorocyclobutyl)-2-oxo-1,2,3,4-tetrahydropyrido[4,3-d]pyrimidin-7-yl)methyl)acrylamide

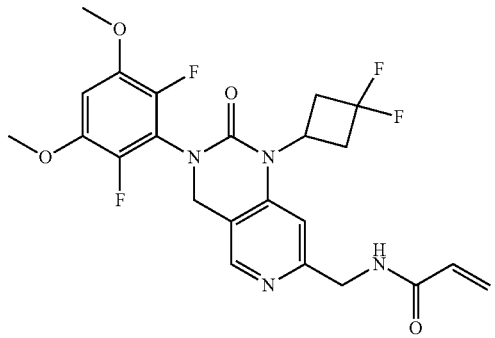 [SMILES: C=CC(=O)NCc1cc2c(cn1)CN(c1c(F)c(OC)cc(OC)c1F)C(=O)N2C1CC(F)(F)C1]

The title compound was prepared using procedures analogous to those described for Example 3, with 3,3-difluorocyclobutanamine replacing 3-pyridinamine in Step 2. LCMS calculated for $C_{23}H_{23}F_4N_4O_4$ [M+H]$^+$ m/z: 495.2; Found: 495.2.

Example 10

N-((1-cyclopropyl-3-(2,6-difluoro-3,5-dimethoxyphenyl)-2-oxo-1,2,3,4-tetrahydropyrido[4,3-d]pyrimidin-7-yl)methyl)acrylamide

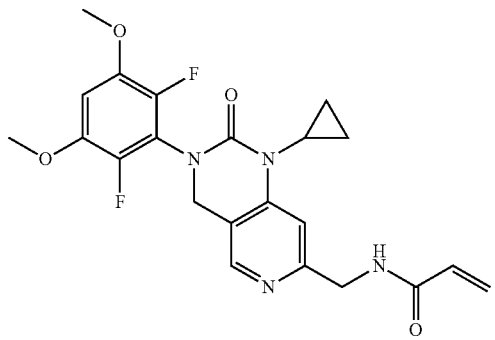 [SMILES: C=CC(=O)NCc1cc2c(cn1)CN(c1c(F)c(OC)cc(OC)c1F)C(=O)N2C1CC1]

The title compound was prepared using procedures analogous to those described for Example 2, with cyclopropanamine replacing ethylamine in Step 1. LCMS calculated for $C_{22}H_{23}F_2N_4O_4$ [M+H]$^+$ m/z: 445.2; Found: 445.2.

Example 11

N-((3-(2,6-difluoro-3,5-dimethoxyphenyl)-1-(2-methoxyethyl)-2-oxo-1,2,3,4-tetrahydropyrido[4,3-d]pyrimidin-7-yl)methyl)acrylamide

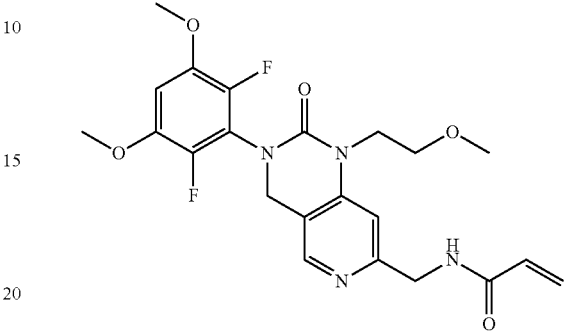

The title compound was prepared using procedures analogous to those described for Example 2, with 2-methoxyethanamine replacing ethylamine in Step 1. LCMS calculated for $C_{22}H_{25}F_2N_4O_5$ [M+H]$^+$ m/z: 463.2; Found: 463.2. $^1$H NMR (500 MHz, DMSO-d$_6$): δ 8.83 (t, J=5.7 Hz, 1H), 8.35 (s, 1H), 7.36 (s, 1H), 7.07 (t, J=8.2 Hz, 1H), 6.33 (dd, J=17.1, 10.2 Hz, 1H), 6.15 (dd, J=17.1, 2.0 Hz, 1H), 5.68 (dd, J=10.2, 2.0 Hz, 1H), 4.82 (s, 2H), 4.52 (d, J=5.8 Hz, 2H), 4.06 (t, J=5.6 Hz, 2H), 3.89 (s, 6H), 3.55 (t, J=5.6 Hz, 2H), 3.22 (s, 3H).

Example 12

N-((3-(2,6-difluoro-3,5-dimethoxyphenyl)-2-oxo-1-propyl-1,2,3,4-tetrahydropyrido[4,3-d]pyrimidin-7-yl)methyl)acrylamide

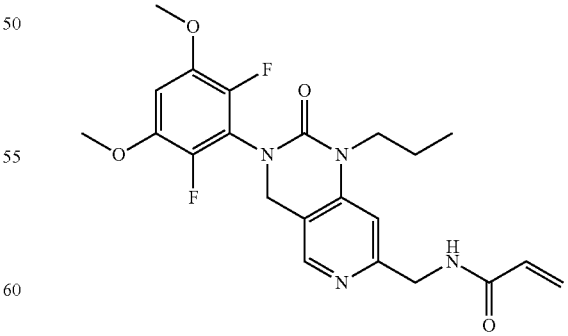

The title compound was prepared using procedures analogous to those described for Example 2, with propan-1-amine replacing ethylamine in Step 1. LCMS calculated for $C_{22}H_{25}F_2N_4O_4$ [M+H]$^+$ m/z: 447.2; Found: 447.2.

Example 13

N-((1-(cyclopropylmethyl)-3-(2,6-difluoro-3,5-dimethoxyphenyl)-2-oxo-1,2,3,4-tetrahydropyrido[4,3-d]pyrimidin-7-yl)methyl)acrylamide

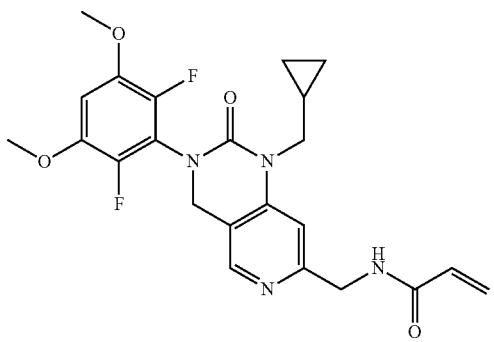 [SMILES: C=CC(=O)NCc1cc2c(cn1)CN(c1c(F)c(OC)cc(OC)c1F)C(=O)N2CC1CC1]

The title compound was prepared using procedures analogous to those described for Example 2, with cyclopropylmethanamine replacing ethylamine in Step 1. LCMS calculated for $C_{23}H_{25}F_2N_4O_4$ [M+H]$^+$ m/z: 459.2; Found: 459.1.

Example 14

N-((3-(2,6-difluoro-3,5-dimethoxyphenyl)-1-(2,2-difluoroethyl)-2-oxo-1,2,3,4-tetrahydropyrido[4,3-d]pyrimidin-7-yl)methyl)acrylamide

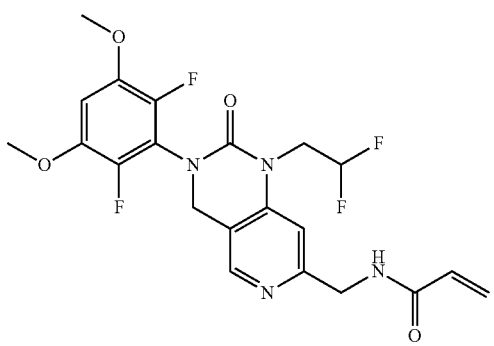

The title compound was prepared using procedures analogous to those described for Example 2, with 2,2-difluoroethanamine replacing ethylamine in Step 1. LCMS calculated for $C_{21}H_{21}F_4N_4O_4$ [M+H]$^+$ m/z: 469.2; Found: 469.1.

Example 15

N-((3-(2,6-difluoro-3,5-dimethoxyphenyl)-1-isopropyl-2-oxo-1,2,3,4-tetrahydropyrido[4,3-d]pyrimidin-7-yl)methyl)acrylamide

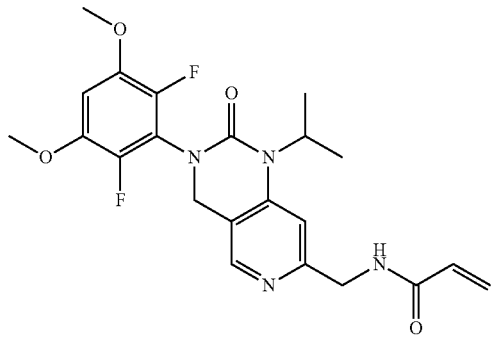 [SMILES: C=CC(=O)NCc1cc2c(cn1)CN(c1c(F)c(OC)cc(OC)c1F)C(=O)N2C(C)C]

The title compound was prepared using procedures analogous to those described for Example 2, with propan-2-amine replacing ethylamine in Step 1. LCMS calculated for $C_{22}H_{25}F_2N_4O_4$ [M+H]$^+$ m/z: 447.2; Found: 447.2.

Example 16

N-((3-(2,6-difluoro-3,5-dimethoxyphenyl)-1-(3-fluorobenzyl)-2-oxo-1,2,3,4-tetrahydropyrido[4,3-d]pyrimidin-7-yl)methyl)acrylamide

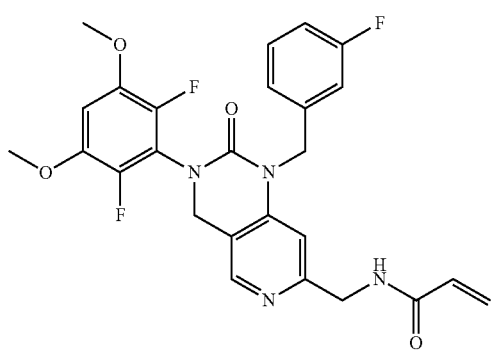 [SMILES: C=CC(=O)NCc1cc2c(cn1)CN(c1c(F)c(OC)cc(OC)c1F)C(=O)N2Cc1cccc(F)c1]

The title compound was prepared using procedures analogous to those described for Example 2, with (3-fluorophenyl)methanamine replacing ethylamine in Step 1. LCMS calculated for $C_{26}H_{24}F_3N_4O_4$ [M+H]$^+$ m/z: 513.2; Found: 513.2.

Example 17

N-((3-(2,6-difluoro-3,5-dimethoxyphenyl)-2-oxo-1-(pyridin-3-ylmethyl)-1,2,3,4-tetrahydropyrido[4,3-d]pyrimidin-7-yl)methyl)acrylamide

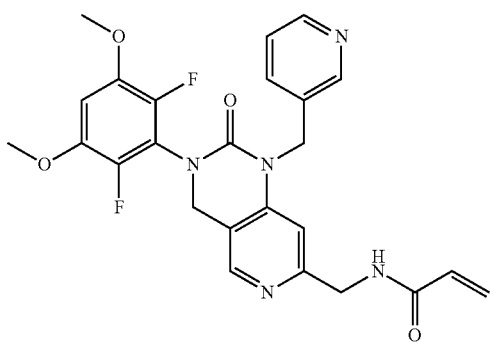 [SMILES: C=CC(=O)NCc1cc2c(cn1)CN(c1c(F)c(OC)cc(OC)c1F)C(=O)N2Cc1cccnc1]

The title compound was prepared using procedures analogous to those described for Example 2, with pyridin-3-ylmethanamine replacing ethylamine in Step 1. LCMS calculated for $C_{25}H_{24}F_2N_5O_4$ [M+H]$^+$ m/z: 496.2; Found: 496.2.

Example 18

N-((3-(2,6-difluoro-3,5-dimethoxyphenyl)-1-((1-methyl-1H-pyrazol-4-yl)methyl)-2-oxo-1,2,3,4-tetrahydropyrido[4,3-d]pyrimidin-7-yl)methyl)acrylamide

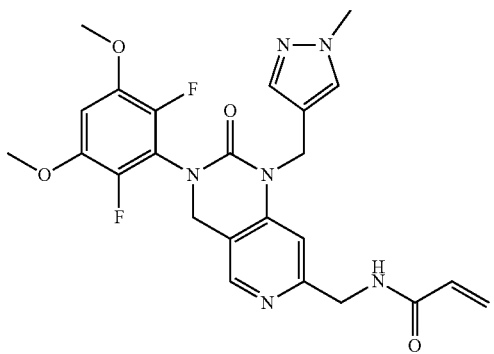 [SMILES: C=CC(=O)NCc1cc2c(cn1)CN(c1c(F)c(OC)cc(OC)c1F)C(=O)N2Cc1cnn(C)c1]

The title compound was prepared using procedures analogous to those described for Example 2, with pyridin-3-ylmethanamine replacing ethylamine in Step 1. LCMS calculated for $C_{24}H_{25}F_2N_6O_4$ [M+H]$^+$ m/z: 499.2; Found: 499.2.

Example 19

(R)—N-((3-(2,6-difluoro-3,5-dimethoxyphenyl)-2-oxo-1-(((tetrahydrofuran-3-yl)methyl)-1,2,3,4-tetrahydropyrido[4,3-d]pyrimidin-7-yl)methyl)acrylamide

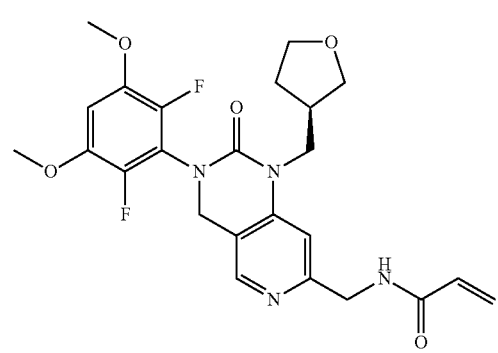 [SMILES: C=CC(=O)NCc1cc2c(cn1)CN(c1c(F)c(OC)cc(OC)c1F)C(=O)N2C[C@H]1CCOC1]

The title compound was prepared using procedures analogous to those described for Example 2, with (R)-(tetrahydrofuran-3-yl)methanamine replacing ethylamine in Step 1. LCMS calculated for $C_{24}H_{27}F_2N_4O_5$ [M+H]$^+$ m/z: 489.2; Found: 489.2.

Example 20

N-((1-(cyanomethyl)-3-(2,6-difluoro-3,5-dimethoxyphenyl)-2-oxo-1,2,3,4-tetrahydropyrido[4,3-d]pyrimidin-7-yl)methyl)acrylamide

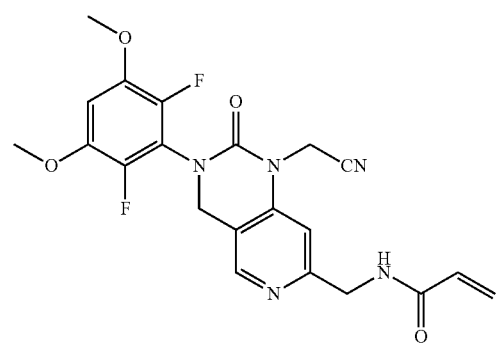 [SMILES: C=CC(=O)NCc1cc2c(cn1)CN(c1c(F)c(OC)cc(OC)c1F)C(=O)N2CC#N]

The title compound was prepared using procedures analogous to those described for Example 2, with 2-aminoacetonitrile replacing ethylamine in Step 1. LCMS calculated for $C_{21}H_{20}F_2N_5O_4$ [M+H]$^+$ m/z: 444.2; Found: 444.2.

Example 21

N-((3-(2,6-difluoro-3,5-dimethoxyphenyl)-2-oxo-1-(2,2,2-trifluoroethyl)-1,2,3,4-tetrahydropyrido[4,3-d]pyrimidin-7-yl)methyl)acrylamide

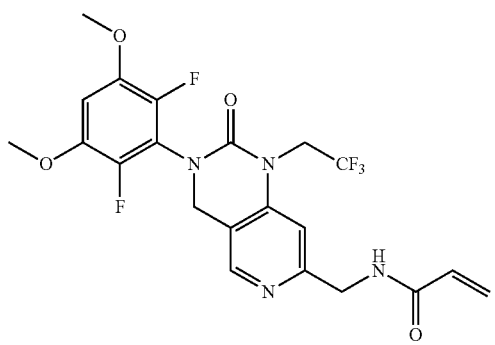 [SMILES: C=CC(=O)NCc1cc2c(cn1)CN(c1c(F)c(OC)cc(OC)c1F)C(=O)N2CC(F)(F)F]

The title compound was prepared using procedures analogous to those described for Example 2, with 2,2,2-trifluoroethanamine replacing ethylamine in Step 1. LCMS calculated for $C_{21}H_{20}F_5N_4O_4$ [M+H]$^+$ m/z: 487.1; Found: 487.1.

Example 22

N-((3-(2,6-difluoro-3,5-dimethoxyphenyl)-1-methyl-2-oxo-1,2,3,4-tetrahydropyrido[4,3-d]pyrimidin-7-yl)methyl)acrylamide

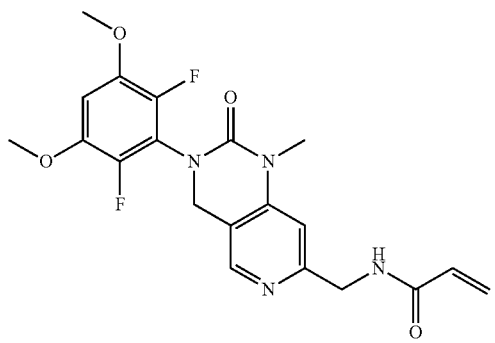 [SMILES: C=CC(=O)NCc1cc2c(cn1)CN(c1c(F)c(OC)cc(OC)c1F)C(=O)N2C]

The title compound was prepared using procedures analogous to those described for Example 2, with methylamine replacing ethylamine in Step 1. LCMS calculated for $C_{20}H_{21}F_2N_4O_4$ [M+H]$^+$ m/z: 419.2; Found: 419.1.

Example 23

N-((3-(2,6-difluoro-3,5-dimethoxyphenyl)-2-oxo-1-(tetrahydro-2H-pyran-4-yl)-1,2,3,4-tetrahydropyrido[4,3-d]pyrimidin-7-yl)methyl)acrylamide

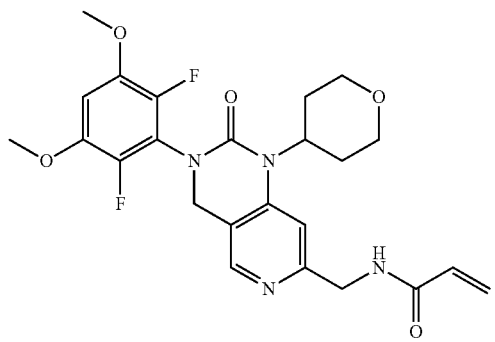 [SMILES: C=CC(=O)NCc1cc2c(cn1)CN(c1c(F)c(OC)cc(OC)c1F)C(=O)N2C1CCOCC1]

The title compound was prepared using procedures analogous to those described for Example 2, with tetrahydro-2H-pyran-4-amine replacing ethylamine in Step 1. LCMS calculated for $C_{24}H_{27}F_2N_4O_5$ [M+H]$^+$ m/z: 489.2; Found: 489.2.

Example 24

N-((7-(2,6-difluoro-3,5-dimethoxyphenyl)-5,5-dimethyl-6-oxo-5,6,7,8-tetrahydro-2,7-naphthyridin-3-yl)methyl)acrylamide

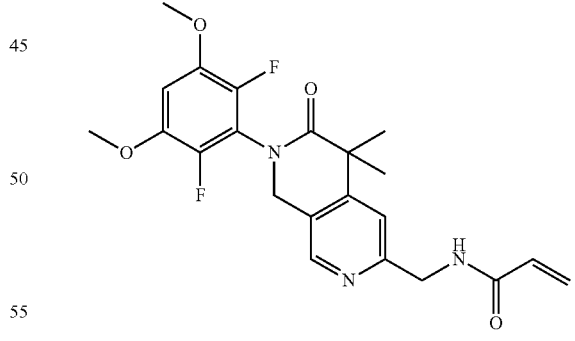

The title compound was prepared using procedures analogous to those described for Example 1, with methyl iodide replacing 1-bromo-2-chloro-ethane in Step 6. LCMS calculated for $C_{22}H_{24}F_2N_3O_4$ [M+H]$^+$ m/z: 432.2; Found: 432.2.

Example 25

N-((1-cyclobutyl-3-(2,6-difluoro-3,5-dimethoxyphenyl)-2-oxo-1,2,3,4-tetrahydropyrido[4,3-d]pyrimidin-7-yl)methyl)acrylamide

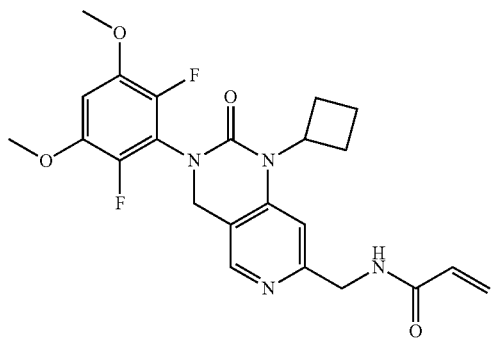 [SMILES: C=CC(=O)NCc1cc2c(cn1)CN(c1c(F)c(OC)cc(OC)c1F)C(=O)N2C1CCC1]

The title compound was prepared using procedures analogous to those described for Example 2, with cyclobutylamine replacing ethylamine in Step 1. LCMS calculated for $C_{23}H_{25}F_2N_4O_4$ [M+H]$^+$ m/z: 459.2; Found: 459.1. $^1$H NMR (500 MHz, dmso) δ 8.82 (t, J=5.8 Hz, 1H), 8.38 (s, 1H), 7.05 (t, J=8.1 Hz, 1H), 6.98 (s, 1H), 6.33 (dd, J=17.1, 10.2 Hz, 1H), 6.14 (dd, J=17.1, 2.0 Hz, 1H), 5.67 (dd, J=10.2, 2.0 Hz, 1H), 4.73 (s, 2H), 4.50 (d, J=5.9 Hz, 2H), 4.45-4.38 (m, 1H), 3.88 (s, 6H), 2.49 (m, 2H), 2.18-2.05 (m, 2H), 1.77-1.69 (m, 2H).

Example 26

N-((3-(2,6-difluoro-3,5-dimethoxyphenyl)-2-oxo-1-(pyridin-4-yl)-1,2,3,4-tetrahydropyrido[4,3-d]pyrimidin-7-yl)methyl)acrylamide

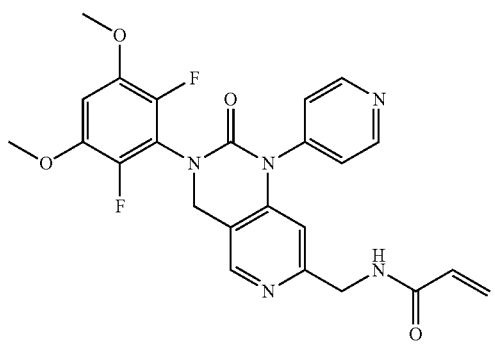

The title compound was prepared using procedures analogous to those described for Example 3, with 4-aminopyridine replacing 3-pyridinamine in Step 2. LCMS calculated for $C_{24}H_{22}F_2N_5O_4$ [M+H]$^+$ m/z: 482.2; Found: 482.1.

Example 27

N-((3-(2,6-difluoro-3,5-dimethoxyphenyl)-1-(2-fluoroethyl)-2-oxo-1,2,3,4-tetrahydropyrido[4,3-d]pyrimidin-7-yl)methyl)acrylamide

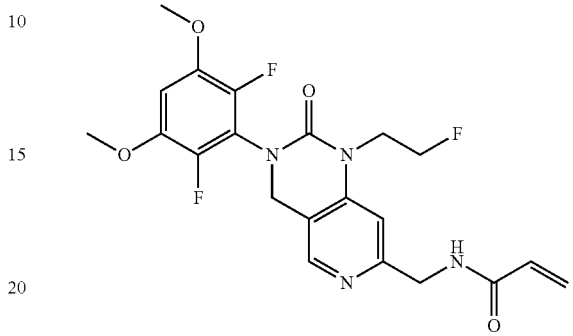

The title compound was prepared using procedures analogous to those described for Example 2, with 2-fluoroethylamine hydrochloride replacing ethylamine in Step 1. LCMS calculated for $C_{21}H_{22}F_3N_4O_4$ [M+H]$^+$ m/z: 451.2; Found: 451.1.

Example 28

N-((1-cyclopentyl-3-(2,6-difluoro-3,5-dimethoxyphenyl)-2-oxo-1,2,3,4-tetrahydropyrido[4,3-d]pyrimidin-7-yl)methyl)acrylamide

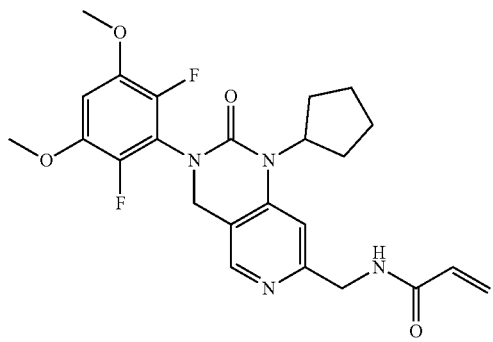 [SMILES: C=CC(=O)NCc1cc2c(cn1)CN(c1c(F)c(OC)cc(OC)c1F)C(=O)N2C1CCCC1]

The title compound was prepared using procedures analogous to those described for Example 3, with cyclopentylamine replacing 3-pyridinamine in Step 2. LCMS calculated for $C_{24}H_{27}F_2N_4O_4$ [M+H]$^+$ m/z: 473.2; Found: 473.1.

Example 29

N-((3-(2,6-difluoro-3,5-dimethoxyphenyl)-1-isobutyl-2-oxo-1,2,3,4-tetrahydropyrido[4,3-d]pyrimidin-7-yl)methyl)acrylamide

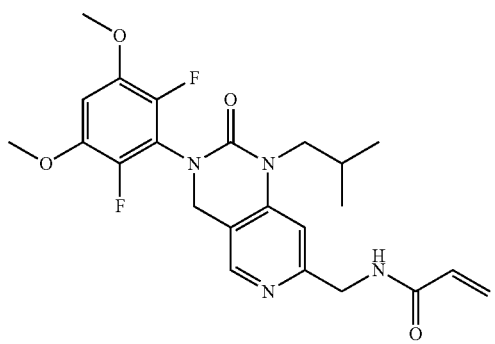

The title compound was prepared using procedures analogous to those described for Example 2, with 2-methylpropan-1-amine replacing ethylamine in Step 1. LCMS calculated for $C_{23}H_{27}F_2N_4O_4$ [M+H]$^+$ m/z: 461.2; Found: 461.2.

Example 30

N-((1-(cyclobutylmethyl)-3-(2,6-difluoro-3,5-dimethoxyphenyl)-2-oxo-1,2,3,4-tetrahydropyrido[4,3-d]pyrimidin-7-yl)methyl)acrylamide

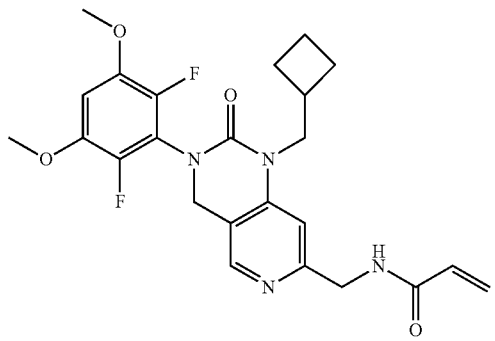 [SMILES: C=CC(=O)NCc1cc2c(cn1)CN(c1c(F)c(OC)cc(OC)c1F)C(=O)N2CC1CCC1]

The title compound was prepared using procedures analogous to those described for Example 2, with cyclobutylmethanamine replacing ethylamine in Step 1. LCMS calculated for $C_{24}H_{27}F_2N_4O_4$ [M+H]$^+$ m/z: 473.2; Found: 473.2.

Example 31

(S)—N-((3-(2,6-difluoro-3,5-dimethoxyphenyl)-2-oxo-1-(((tetrahydrofuran-3-yl)methyl)-1,2,3,4-tetrahydropyrido[4,3-d]pyrimidin-7-yl)methyl)acrylamide

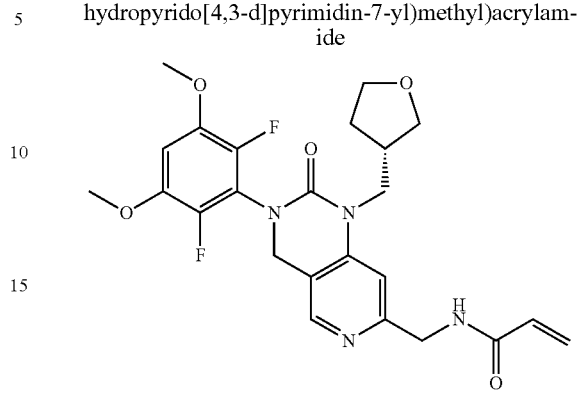

The title compound was prepared using procedures analogous to those described for Example 2, with (S)-(tetrahydrofuran-3-yl)methanamine replacing ethylamine in Step 1. LCMS calculated for $C_{24}H_{27}F_2N_4O_5$ [M+H]$^+$ m/z: 489.2; Found: 489.2.

Example 32

N-((3-(2,6-difluoro-3,5-dimethoxyphenyl)-1-((1-methylpiperidin-4-yl)methyl)-2-oxo-1,2,3,4-tetrahydropyrido[4,3-d]pyrimidin-7-yl)methyl)acrylamide

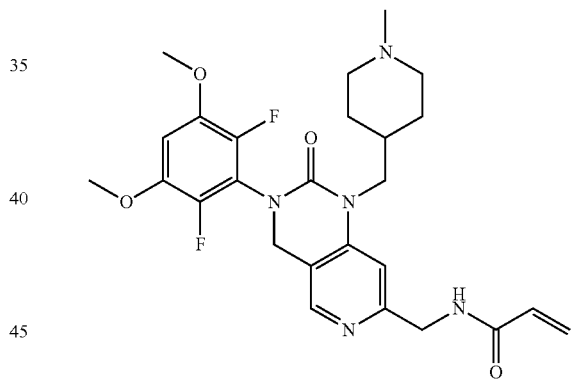

Step 1: 4-chloro-5-((2,6-difluoro-3,5-dimethoxyphenylamino)methyl)picolinonitrile

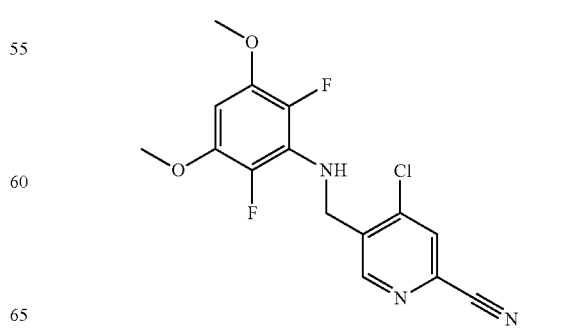

A stirred mixture of N-[(4,6-dichloropyridin-3-yl)methyl]-2,6-difluoro-3,5-dimethoxyaniline (prepared as in Example 1, Step 2, 3.50 g, 10.0 mmol), zinc cyanide (0.79 g, 6.7 mmol), tris(dibenzylideneacetone)dipalladium(0) (0.92 g, 1.0 mmol) and [1,1'-bis(diphenylphosphino)ferrocene]dichloropalladium(II) complexed with dichloromethane (1:1) (0.82 g, 1.0 mmol) in N,N-dimethylformamide (50 mL) was heated at 125-130° C. under an atmosphere of $N_2$ for 1.5 hours. The reaction mixture was then cooled to room temperature, quenched with saturated aqueous $NaHCO_3$, and extracted with ethyl acetate (3×100 mL). The combined organic layers were washed with brine, dried over $MgSO_4$, filtered and concentrated under reduced pressure. The residue was purified on silica gel (eluting with 0-25% EtOAc in hexanes) to give 2.57 g of the desired product. LCMS calculated for $C_{15}H_{13}ClF_2N_3O_2$ [M+H]$^+$ m/z: 340.1; Found: 340.0.

Step 2: tert-butyl 4-{[7-cyano-3-(2,6-difluoro-3,5-dimethoxyphenyl)-2-oxo-3,4-dihydropyrido[4,3-d]pyrimidin-1(2H)-yl]methyl}piperidine-1-carboxylate

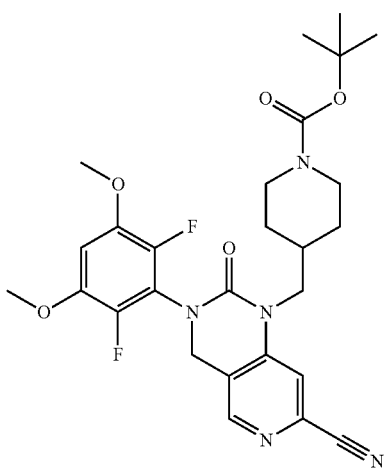 [SMILES: COc1cc(OC)c(F)c(N2Cc3cnc(C#N)cc3N(CC3CCN(C(=O)OC(C)(C)C)CC3)C2=O)c1F]

A stirred mixture of 4-chloro-5-{[(2,6-difluoro-3,5-dimethoxyphenyl)amino]methyl}pyridine-2-carbonitrile (200 mg, 0.6 mmol), tert-butyl 4-(aminomethyl)piperidinecarboxylate (170 μL, 0.82 mmol), palladium acetate (13 mg, 0.059 mmol), (R)-(+)-2,2'-bis(diphenylphosphino)-1,1'-binaphthyl (37 mg, 0.059 mmol), and cesium carbonate (580 mg, 1.8 mmol) in 1,4-dioxane (10 mL) was heated at 110° C. under an atmosphere of $N_2$ for 5 hours. The reaction mixture was cooled to room temperature, diluted with ethyl acetate, filtered and the filtrate was concentrated under reduced pressure. The residue was used directly in the next step without further purification.

To a stirred solution of the above residue in tetrahydrofuran (8 mL), N,N-diisopropylethylamine (620 μL, 3.5 mmol) and triphosgene (170 mg, 0.59 mmol) was added sequentially at room temperature. After 30 minutes, NaOH (2 N in water, 2 mL) was added. The resulting mixture was stirred at 30° C. for 1 hour. The reaction was quenched with saturated aqueous $NaHCO_3$, and extracted with ethyl acetate (3×20 mL). The combined organic layers were washed with brine, dried over $MgSO_4$, filtered and concentrated under reduced pressure. The residue was purified on silica gel (eluting with 0-45% EtOAc in hexanes) to give 0.20 g of the desired product. LCMS calculated for $C_{27}H_{31}F_2N_5NaO_5$ [M+Na]$^+$ m/z: 566.2; Found: 566.2.

Step 3: tert-butyl 4-((7-(aminomethyl)-3-(2,6-difluoro-3,5-dimethoxyphenyl)-2-oxo-3,4-dihydropyrido[4,3-d]pyrimidin-1(2H)-yl)methyl)piperidine-1-carboxylate

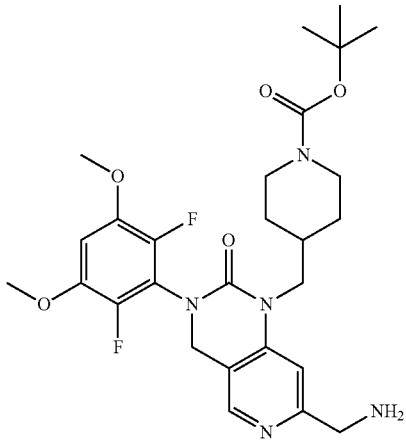 [SMILES: COc1cc(OC)c(F)c(N2Cc3cnc(CN)cc3N(CC3CCN(C(=O)OC(C)(C)C)CC3)C2=O)c1F]

To a solution of tert-butyl 4-{[7-cyano-3-(2,6-difluoro-3,5-dimethoxyphenyl)-2-oxo-3,4-dihydropyrido[4,3-d]pyrimidin-1(2H)-yl]methyl}piperidine-1-carboxylate (200 mg, 0.4 mmol) in methanol (5.0 mL), HCl (1.0 M in water, 680 μL, 0.68 mmol) and Pd/C (10% w/w, 20 mg) were added sequentially at room temperature. The resulting mixture was stirred at room temperature under an atmosphere of $H_2$ for 2 hours. The reaction mixture was filtered, and the filtrate was concentrated under reduced pressure to afford the crude product as its HCl salt. LCMS calculated for $C_{27}H_{36}F_2N_5O_5$ [M+H]$^+$ m/z: 548.3; Found: 548.3.

Step 4: tert-butyl 4-((7-(acrylamidomethyl)-3-(2,6-difluoro-3,5-dimethoxyphenyl)-2-oxo-3,4-dihydropyrido[4,3-d]pyrimidin-1(2H)-yl)methyl)piperidine-1-carboxylate

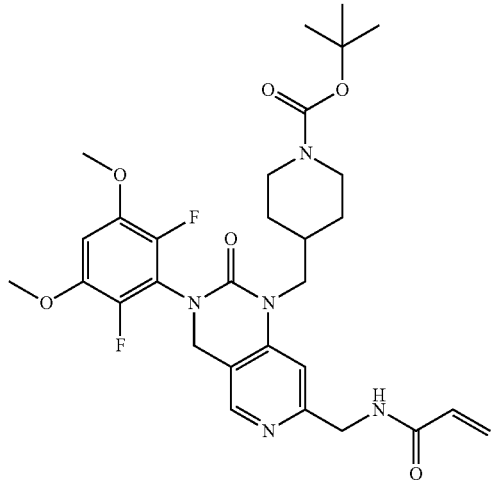 [SMILES: C=CC(=O)NCc1cc2c(cn1)CN(c1c(F)c(OC)cc(OC)c1F)C(=O)N2CC1CCN(C(=O)OC(C)(C)C)CC1]

To a stirred solution of tert-butyl 4-((7-(aminomethyl)-3-(2,6-difluoro-3,5-dimethoxyphenyl)-2-oxo-3,4-dihydropyrido[4,3-d]pyrimidin-1(2H)-yl)methyl)piperidine-1-carboxylate (186 mg, 0.34 mmol) in acetonitrile (2 mL), triethylamine (160 µL, 1.1 mmol) and 2-propenoyl chloride (27 µL, 0.34 mmol) were added sequentially at room temperature. After 30 minutes, the reaction was quenched with saturated aqueous NaHCO$_3$, and extracted with ethyl acetate (3×20 mL). The combined organic layers were washed with brine, dried over MgSO$_4$, filtered and the filtrate was concentrated under reduced pressure. The residue was purified on silica gel (eluting with 0-100% EtOAc in DCM) to give 0.09 g the desired product. LCMS calculated for $C_{30}H_{38}F_2N_5O_6$ [M+H]$^+$ m/z: 602.3; Found: 602.2.

Step 5: N-((3-(2,6-difluoro-3,5-dimethoxyphenyl)-2-oxo-1-(piperidin-4-ylmethyl)-1,2,3,4-tetrahydropyrido[4,3-d]pyrimidin-7-yl)methyl)acrylamide

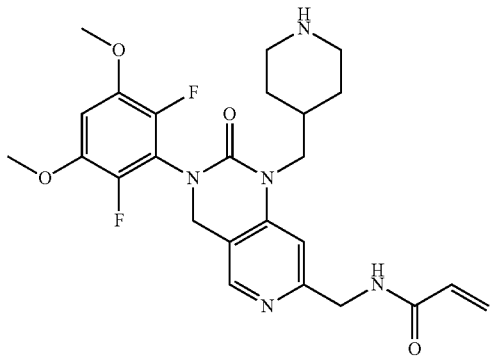 [SMILES: C=CC(=O)NCc1cc2c(cn1)CN(c1c(F)c(OC)cc(OC)c1F)C(=O)N2CC1CCNCC1]

To a stirred solution of tert-butyl 4-((7-(acrylamidomethyl)-3-(2,6-difluoro-3,5-dimethoxyphenyl)-2-oxo-3,4-dihydropyrido[4,3-d]pyrimidin-1(2H)-yl)methyl)piperidine-1-carboxylate (90 mg, 0.15 mmol) in DCM (1 mL), TFA (1 mL) was added at room temperature. After 1 hour, the volatiles were removed under reduced pressure to give desired product as its TFA salt. LCMS calculated for $C_{25}H_{30}F_2N_5O_4$ [M+H]$^+$ m/z: 502.2; Found: 502.2.

Step 6: N-((3-(2,6-difluoro-3,5-dimethoxyphenyl)-1-((1-methylpiperidin-4-yl)methyl)-2-oxo-1,2,3,4-tetrahydropyrido[4,3-d]pyrimidin-7-yl)methyl)acrylamide To a stirred solution of N-{[3-(2,6-difluoro-3,5-dimethoxyphenyl)-2-oxo-1-(piperidin-4-ylmethyl)-1,2,3,4-tetrahydropyrido[4,3-d]pyrimidin-7-yl]methyl}acrylamide 2,2,2-trifluoroacetate (15 mg, 0.030 mmol) in tetrahydrofuran (1 mL), formaldehyde (10.0 M in water, 6.2 µL, 0.062 mmol) and N,N-diisopropylethylamine (14 µL, 0.082 mmol) were added sequentially at room temperature. After 5 minutes, sodium triacetoxyborohydride (13 mg, 0.062 mmol) was added. After another 2 hours, the reaction mixture was diluted with MeOH and purified by RP-HPLC (pH=10, acetonitrile/water+NH$_4$OH) to afford the desired product. LCMS calculated for $C_{26}H_{32}F_2N_5O_4$ [M+H]$^+$ m/z: 516.2; Found: 516.2.

Example 33 methyl 4-((7-(acrylamidomethyl)-3-(2,6-difluoro-3,5-dimethoxyphenyl)-2-oxo-3,4-dihydropyrido[4,3-d]pyrimidin-1(2H)-yl)methyl)piperidine-1-carboxylate

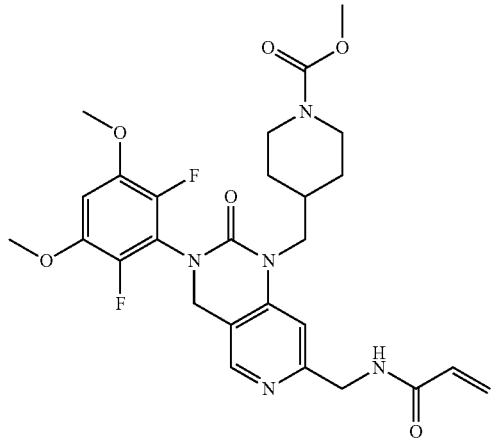 [SMILES: C=CC(=O)NCc1cc2c(cn1)CN(c1c(F)c(OC)cc(OC)c1F)C(=O)N2CC1CCN(C(=O)OC)CC1]

To a stirred solution of N-{[3-(2,6-difluoro-3,5-dimethoxyphenyl)-2-oxo-1-(piperidin-4-ylmethyl)-1,2,3,4-tetrahydropyrido[4,3-d]pyrimidin-7-yl]methyl}acrylamide 2,2,2-trifluoroacetate (prepared as in Example 32, Step 5, 15 mg, 0.030 mmol) in tetrahydrofuran (1.0 mL), N,N-diisopropylethylamine (14 µL, 0.082 mmol) and methyl chloroformate (2.4 µL, 0.031 mmol) were added sequentially at room temperature. After 30 minutes, the reaction mixture diluted with MeOH and purified by RP-HPLC (pH=10, acetonitrile/water+NH$_4$OH) to afford the desired product. LCMS calculated for $C_{27}H_{32}F_2N_5O_6$ [M+H]$^+$ m/z: 560.2; Found: 560.3.

Example 34

4-((7-(acrylamidomethyl)-3-(2,6-difluoro-3,5-dimethoxyphenyl)-2-oxo-3,4-dihydropyrido[4,3-d]pyrimidin-1(2H)-yl)methyl)-N-isopropylpiperidine-1-carboxamide

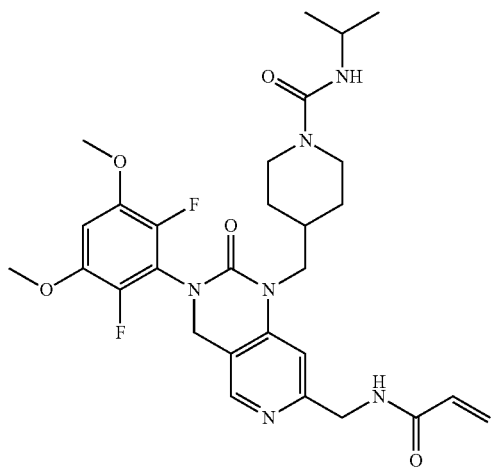 [SMILES: C=CC(=O)NCc1cc2c(cn1)CN(c1c(F)c(OC)cc(OC)c1F)C(=O)N2CC1CCN(C(=O)NC(C)C)CC1]

The title compound was prepared using procedures analogous to those described for Example 33, with 2-isocyanatopropane replacing methyl chloroformate. LCMS calculated for $C_{29}H_{37}F_2N_6O_5$ [M+H]$^+$ m/z: 587.3; Found: 587.2.

Example 35

N-((3-(2,6-difluoro-3,5-dimethoxyphenyl)-1-((1-(methylsulfonyl)piperidin-4-yl)methyl)-2-oxo-1,2,3,4-tetrahydropyrido[4,3-d]pyrimidin-7-yl)methyl)acrylamide

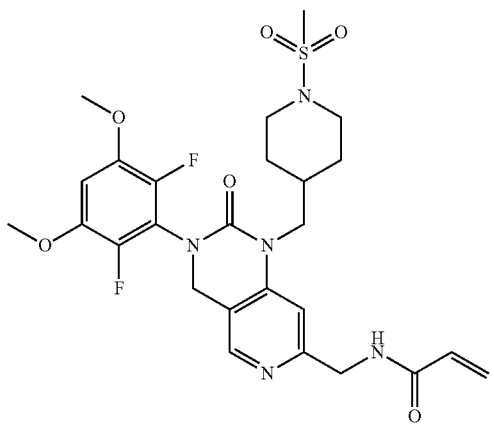 [SMILES: C=CC(=O)NCc1cc2c(cn1)CN(c1c(F)c(OC)cc(OC)c1F)C(=O)N2CC1CCN(S(C)(=O)=O)CC1]

The title compound was prepared using procedures analogous to those described for Example 33, with methanesulfonyl chloride replacing methyl chloroformate. LCMS calculated for $C_{26}H_{32}F_2N_5O_6S$ [M+H]$^+$ m/z: 580.2; Found: 580.1.

Example 36

N-((3-(2,6-dichloro-3,5-dimethoxyphenyl)-1-ethyl-2-oxo-1,2,3,4-tetrahydropyrido[4,3-d]pyrimidin-7-yl)methyl)acrylamide

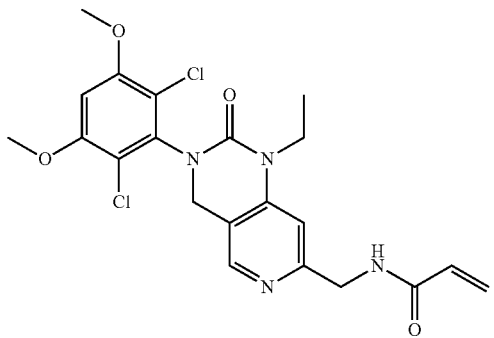 [SMILES: C=CC(=O)NCc1cc2c(cn1)CN(c1c(Cl)c(OC)cc(OC)c1Cl)C(=O)N2CC]

Step: N-(3,5-dimethoxyphenyl)acetamide

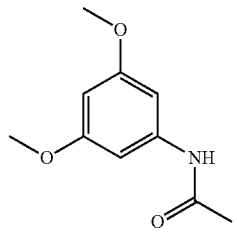

To a stirred solution of 3,5-dimethoxyaniline (15.0 g, 97.9 mmol) in toluene (200 mL) was added acetic anhydride (10.2 mL, 108 mmol) dropwise. After 3 hours, the reaction mixture was diluted with 100 mL hexanes, filter and the solid was washed with toluene/hexane (2:1, 30 mL), then hexanes. The solid was dried under reduced pressure to give the desired compound (18.9 g). LCMS calculated for $C_{10}H_{14}NO_3$ [M+H]$^+$ m/z: 196.1; Found: 196.2.

Step 2:
N-(2,6-dichloro-3,5-dimethoxyphenyl)acetamide

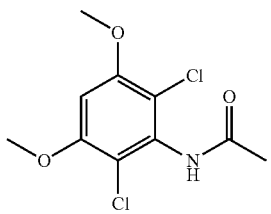 [SMILES: COc1cc(OC)c(Cl)c(NC(C)=O)c1Cl]

To a stirred suspension of N-(3,5-dimethoxyphenyl)acetamide (16.0 g, 82.0 mmol) in acetonitrile (200 mL), sulfuryl chloride (13.0 mL, 160 mmol) was added dropwise over 5 minutes at 0° C. After 30 minutes, the reaction was quenched with saturated aqueous NaHCO$_3$ (125 mL), filtered and the solid was washed with water and hexanes to afford the desired product, (8.5 g). The filtrate was diluted with 100 mL of saturated aqueous NaHCO$_3$ then extracted with EtOAc. The organic layers were combined, washed with water, dried over Na$_2$SO$_4$, filtered and the filtrate was concentrated under reduced pressure. The residue was purified on silica gel (eluting with 0-40% EtOAc in hexanes) to afford another 10.0 g of the desired product. LCMS calculated for $C_{10}H_{12}Cl_2NO_3$ [M+H]$^+$ m/z: 264.0; Found: 263.9.

Step 3: 2,6-dichloro-3,5-dimethoxyaniline

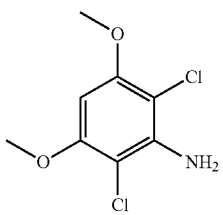

N-(2,6-dichloro-3,5-dimethoxyphenyl)acetamide (8.5 g, 32 mmol) was dissolved in ethanol (160 mL) then a solution of potassium hydroxide (9.0 g, 160 mmol) in water (80 mL) was added. The mixture was heated to reflux and stirred for 48 hours. After the reaction was cooled to room temperature, the white precipitate was collected via filtration and washed with cold water then dried to get the desired product (6.0 g). LCMS calculated for $C_8H_{10}Cl_2NO_2$ [M+H]$^+$ m/z: 222.0; Found: 221.9.

Step 4: 2,6-dichloro-N-((4,6-dichloropyridin-3-yl)methyl)-3,5-dimethoxyaniline

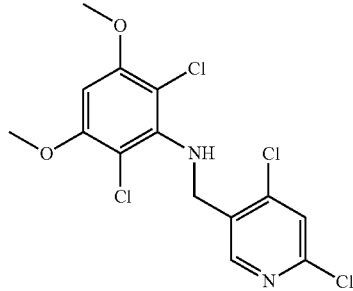 [SMILES: COc1cc(OC)c(Cl)c(NCc2cnc(Cl)cc2Cl)c1Cl]

The title compound was prepared using procedures analogous to those described for Example 1, Step 2 with 2,6-dichloro-3,5-dimethoxyaniline replacing 2,6-difluoro-3,5-dimethoxyaniline. LCMS calculated for $C_{14}H_{13}Cl_4N_2O_2$ [M+H]$^+$ m/z: 381.0; Found: 381.0.

Step 5: N-((3-(2,6-dichloro-3,5-dimethoxyphenyl)-1-ethyl-2-oxo-1,2,3,4-tetrahydropyrido[4,3-d]pyrimidin-7-yl)methyl) acrylamide The title compound was prepared using procedures analogous to those described for Example 2, with 2,6-dichloro-N-((4,6-dichloropyridin-3-yl)methyl)-3,5-dimethoxyaniline (Step 4) replacing 2,6-difluoro-N-((4,6-dichloropyridin-3-yl)methyl)-3,5-dimethoxyaniline in Step 1.

LCMS calculated for $C_{21}H_{23}Cl_2N_4O_4$ [M+H]$^+$ m/z: 465.1; Found: 465.1.

Example 37

N-((2'-(2,6-difluoro-3,5-dimethoxyphenyl)-5'-methyl-3'-oxo-2',3'-dihydro-1'H-spiro[cyclopropane-1,4'-[2,7]naphthyridine]-6'-yl)methyl)acrylamide

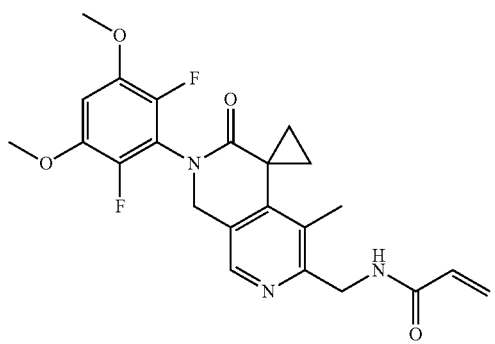 [SMILES: C=CC(=O)NCc1ncc2c(c1C)C1(CC1)C(=O)N(c1c(F)c(OC)cc(OC)c1F)C2]

Step 1: (4,6-dichloro-5-methylpyridin-3-yl)methanol

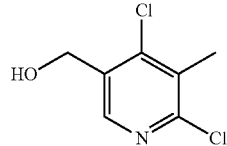

To a stirred solution of ethyl 4,6-dichloro-5-methylnicotinate (6.70 g, 28.6 mmol) in methylene chloride (100 mL), diisobutylaluminum hydride (1.0 M in toluene, 60. mL, 60. mmol) was added dropwise at −78° C. After 1 hour, the reaction mixture was quenched with saturated aqueous potassium sodium tartrate (7 mL) then stirred at room temperature overnight. The organic layer was separated and the aqueous layer was extracted with DCM. The combined organic layers were dried over MgSO$_4$, filtered and concentrated under reduced pressure to afford the crude product (5.46 g). LCMS calculated for $C_7H_8Cl_2NO$ [M+H]$^+$ m/z: 192.0; Found: 192.0.

Step 2: N-((4,6-dichloro-5-methylpyridin-3-yl)methyl)-2,6-difluoro-3,5-dimethoxyaniline

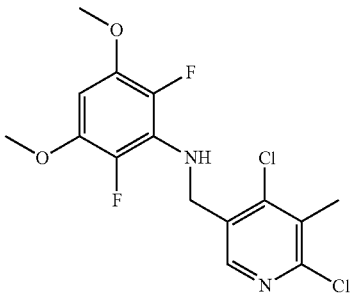

To a stirred solution of (4,6-dichloro-5-methylpyridin-3-yl)methanol (5.46 g, 28.4 mmol) in methylene chloride (100 mL), N,N-diisopropylethylamine (9.90 mL, 56.9 mmol) and methanesulfonyl chloride (2.9 mL, 37 mmol) were added sequentially at 0° C. After another 2 hours, the reaction mixture was quenched with saturated aqueous NaHCO$_3$, and extracted with DCM (3×100 mL). The combined organic layers were washed with brine, dried over MgSO$_4$, filtered and concentrated under reduced pressure. The residue was used in the next step without further purification.

2,6-difluoro-3,5-dimethoxyaniline (7.5 g, 40. mmol) was added to the above residue in N,N-diisopropylethylamine (24 mL, 140 mmol). The resulting mixture was stirred at 100° C. overnight. The reaction mixture was cooled to room temperature, quenched with saturated aqueous NaHCO$_3$, and extracted with ethyl acetate (3×100 mL). The combined organic layers were washed with brine, dried over MgSO$_4$, filtered and concentrated under reduced pressure. The residue was purified on silica gel (eluting with 0-25% EtOAc in hexanes) to afford 7.5 g of the desired product. LCMS calculated for $C_{15}H_{15}Cl_2F_2N_2O_2$ [M+H]$^+$ m/z: 363.0; Found: 363.0.

Step 3: 6'-chloro-2'-(2,6-difluoro-3,5-dimethoxyphenyl)-5'-methyl-1'H-spiro[cyclopropane-1,4'-[2,7]naphthyridin]-3'(2'H)-one

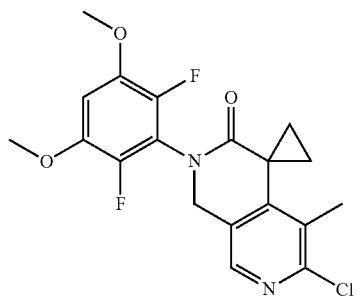

The title compound was prepared using procedures analogous to those described for Example 1, Steps 3 to 6, with N-((4,6-dichloro-5-methylpyridin-3-yl)methyl)-2,6-difluoro-3,5-dimethoxyaniline (Step 2) replacing N-((4,6-dichloropyridin-3-yl)methyl)-2,6-difluoro-3,5-dimethoxyaniline in Step 3. LCMS calculated for $C_{19}H_{18}ClF_2N_2O_3$ [M+H]$^+$ m/z: 395.1; Found: 395.1.

Step 4: N-((2'-(2,6-difluoro-3,5-dimethoxyphenyl)-5'-methyl-3'-oxo-2',3'-dihydro-1'H-spiro[cyclopropane-1,4'-[2,7]naphthyridine]-6'-yl)methyl)acrylamide The title compound was prepared using procedures analogous to those described for Example 2, Steps 2 to 6, with 6'-chloro-2'-(2,6-difluoro-3,5-dimethoxyphenyl)-5'-methyl-1'H-spiro[cyclopropane-1,4'-[2,7]naphthyridin]-3'(2'H)-one (Step 3) replacing 7-chloro-3-(2,6-difluoro-3,5-dimethoxyphenyl)-1-ethyl-3,4-dihydropyrido[4,3-d]pyrimidin-2(1H)-one in Step 2. LCMS calculated for $C_{23}H_{24}F_2N_3O_4$ [M+H]$^+$ m/z: 444.2; Found: 444.2.

Example A

FGFR Enzymatic Assay

The inhibitor potency of the exemplified compounds was measured in an enzyme assay that measures peptide phosphorylation using FRET measurements to detect product formation. Inhibitors were serially diluted in DMSO and a volume of 0.5 µL was transferred to the wells of a 384-well plate. For FGFR3, a 10 µL volume of FGFR3 enzyme (Millipore) diluted in assay buffer (50 mM HEPES, 10 mM MgCl$_2$, 1 mM EGTA, 0.01% Tween-20, 5 mM DTT, pH 7.5) was added to the plate and pre-incubated for a time between 5-10 minutes and up to 4 hours. Appropriate controls (enzyme blank and enzyme with no inhibitor) were included on the plate. The assay was initiated by the addition of a 10 µL solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions were ended with the addition of 10 µL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate was allowed to equilibrate for ~1 hr before scanning the wells on a PheraStar plate reader (BMG Labtech).

FGFR1, FGFR2, and FGFR4 are measured under equivalent conditions with the following changes in enzyme and ATP concentrations: FGFR1, 0.02 nM and 210 uM respectively, FGFR2, 0.01 nM and 100 uM, respectively, and FGFR4, 0.04 nM and 600 uM respectively. The enzymes were purchased from Millipore or Invitrogen.

GraphPad prism3 was used to analyze the data. The IC$_{50}$ values were derived by fitting the data to the equation for a sigmoidal dose-response with a variable slope. Y=Bottom+ (Top−Bottom)/(1+10^((Log IC$_{50}$−X)*HillSlope)) where X is the logarithm of concentration and Y is the response. Compounds having an IC$_{50}$ of 1 µM or less are considered active.

The compounds of the invention were found to be selective inhibitors of FGFR4 according to the FGFR Enzymatic Assay. Table 1 provides IC$_{50}$ data for compounds of the invention assayed in the FGFR Enzymatic Assay after dilution in assay buffer, added to the plate and pre-incubated for 4 hours. The symbol: "+" indicates an IC$_{50}$ less than 10 nM; "++" indicates an IC$_{50}$ greater than or equal to 10 nM but less than 30 nM; "+++" indicates an IC$_{50}$ greater than or equal to 30 nM but less than 200 nM; and "++++" indicates an IC$_{50}$ greater than or equal to 200 nM.

TABLE 1

| Example No. | FGFR1 IC50 (nM) | FGFR2 IC50 (nM) | FGFR3 IC50 (nM) | FGFR4 IC50 (nM) |
|---|---|---|---|---|
| 1 | +++ | +++ | +++ | + |
| 2 | ++++ | ++++ | ++++ | + |
| 3 | ++++ | ++++ | ++++ | ++ |
| 4 | ++++ | ++++ | ++++ | ++ |
| 5 | ++++ | ++++ | ++++ | + |
| 6 | ++++ | ++++ | ++++ | ++ |
| 7 | ++++ | ++++ | ++++ | ++ |
| 8 | ++++ | ++++ | ++++ | + |
| 9 | ++++ | ++++ | ++++ | ++ |
| 10 | ++++ | ++++ | ++++ | ++ |
| 11 | ++++ | ++++ | ++++ | + |
| 12 | ++++ | ++++ | ++++ | + |
| 13 | +++ | ++++ | +++ | + |
| 14 | ++++ | ++++ | ++++ | + |
| 15 | ++++ | ++++ | ++++ | + |
| 16 | +++ | +++ | +++ | ++ |
| 17 | ++++ | ++++ | ++++ | ++ |
| 18 | +++ | +++ | +++ | + |
| 19 | ++++ | ++++ | ++++ | + |
| 20 | ++++ | ++++ | ++++ | + |
| 21 | ++++ | ++++ | ++++ | + |
| 22 | ++++ | ++++ | ++++ | ++ |
| 23 | ++++ | +++ | ++++ | ++ |
| 24 | ++++ | ++++ | ++++ | +++ |
| 25 | ++++ | ++++ | ++++ | ++ |
| 26 | ++++ | ++++ | ++++ | ++ |
| 27 | ++++ | ++++ | ++++ | + |
| 28 | +++ | +++ | +++ | + |
| 29 | +++ | +++ | ++++ | + |
| 30 | +++ | +++ | ++++ | + |
| 31 | ++++ | ++++ | ++++ | + |
| 32 | ++++ | ++++ | ++++ | +++ |
| 33 | ++++ | ++++ | +++ | + |
| 34 | ++++ | ++++ | ++++ | + |
| 35 | ++++ | ++++ | ++++ | + |
| 36 | ++++ | ++++ | ++++ | + |
| 37 | ++++ | ++++ | ++++ | ++ |

Table 2 provides IC$_{50}$ data for compounds of the invention assayed in the FGFR Enzymatic Assay after dilution in assay buffer, added to the plate and pre-incubated for 5 to 10 minutes. The symbol: "+" indicates an IC$_{50}$ less than 10 nM; "++" indicates an IC$_{50}$ greater than or equal to 10 nM but less than 30 nM; "+++" indicates an IC$_{50}$ greater than or equal to 30 nM but less than 200 nM; and "++++" indicates an IC$_{50}$ greater than or equal to 200 nM.

TABLE 2

| Example No. | FGFR1 IC50 (nM) | FGFR2 IC50 (nM) | FGFR3 IC50 (nM) | FGFR4 IC50 (nM) |
|---|---|---|---|---|
| 1 | +++ | ++++ | ++++ | + |

Example B

FGFR4 Cellular and In Vivo Assays

The FGFR4 inhibitory activity of the example compounds in cells, tissues, and/or animals can be demonstrated according to one or more assays or models described in the art such as, for example, in French et al. "Targeting FGFR4 Inhibits Hepatocellular Carcinoma in Preclinical Mouse Models," PLoS ONE, May 2012, Vol. 7, Issue 5, e36713, which is incorporated herein by reference in its entirety.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient in need thereof, comprising administering to said patient a therapeutically effective amount of a compound selected from the group consisting of:
    N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide;
    N-((3-(2,6-difluoro-3,5-dimethoxyphenyl)-1-ethyl-2-oxo-1,2,3,4-tetrahydropyrido[4,3-d]pyrimidin-7-yl)methyl)acrylamide;
    N-((3-(2,6-difluoro-3,5-dimethoxyphenyl)-2-oxo-1-(pyridin-3-yl)-1,2,3,4-tetrahydropyrido[4,3-d]pyrimidin-7-yl)methyl)acrylamide; and
    N-((6'-(2,6-difluoro-3,5-dimethoxyphenyl)-7'-oxo-6',7'-dihydro-5'H-spiro[cyclopropane-1,8'-pyrido[4,3-d]pyrimidine]-2'-yl)methyl)acrylamide;
    or a pharmaceutically acceptable salt thereof;
    and wherein the cancer is selected from the group consisting of hepatocellular carcinoma, ovarian cancer, kidney cancer, esophageal cancer, head and neck cancer, rhabdomyosarcoma, breast cancer, lung cancer, colorectal cancer, and prostate cancer.

2. The method of claim 1, wherein the cancer is breast cancer.

3. The method of claim 1, wherein the cancer is lung cancer.

4. The method of claim 3, wherein the lung cancer is non-small cell lung cancer.

5. The method of claim 3, wherein the lung cancer is adenocarcinoma, small cell lung cancer, parvicellular carcinoma, non-parvicellular carcinoma, bronchial carcinoma, bronchial adenoma, or pleuropulmonary blastoma.

6. The method of claim 1, wherein the cancer is esophageal cancer.

7. The method of claim 1, wherein the cancer is head and neck cancer.

8. The method of claim 1, wherein the cancer is ovarian cancer.

9. The method of claim 1, wherein the cancer is hepatocellular carcinoma.

10. The method of claim 1, wherein the compound is N-{([2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide or a pharmaceutically acceptable salt thereof.

11. The method of claim 1, wherein the compound is N-((3-(2,6-difluoro-3,5-dimethoxyphenyl)-1-ethyl-2-oxo-1,2,3,4-tetrahydropyrido[4,3-d]pyrimidin-7-yl)methyl)acrylamide or a pharmaceutically acceptable salt thereof.

12. The method of claim 1, wherein the compound is N-((3-(2,6-difluoro-3,5-dimethoxyphenyl)-2-oxo-1-(pyridin-3-yl)-1,2,3,4-tetrahydropyrido[4,3-d]pyrimidin-7-yl)methyl)acrylamide or a pharmaceutically acceptable salt thereof.

13. The method of claim 1, wherein the compound is N-((6'-(2,6-difluoro-3,5-dimethoxyphenyl)-7'-oxo-6',7'-dihydro-5'H-spiro[cyclopropane-1,8'-pyrido[4,3-d]pyrimidine]-2'-yl)methyl)acrylamide or a pharmaceutically acceptable salt thereof.

14. The method of claim 1, wherein the compound is N-{[2'-(2,6-difluoro-3,5-dimethoxyphenyl)-3'-oxo-2',3'-dihydro-1'H-spiro[cyclopropane-1,4'-[2,7]naphthyridin]-6'-yl]methyl}acrylamide or a pharmaceutically acceptable salt thereof, and wherein the cancer is hepatocellular carcinoma.

15. The method of claim 1, wherein the compound is N-((3-(2,6-difluoro-3,5-dimethoxyphenyl)-1-ethyl-2-oxo-1,2,3,4-tetrahydropyrido[4,3-d]pyrimidin-7-yl)methyl)acrylamide or a pharmaceutically acceptable salt thereof, and wherein the cancer is hepatocellular carcinoma.

16. The method of claim 1, wherein the compound is N-((3-(2,6-difluoro-3,5-dimethoxyphenyl)-2-oxo-1-(pyridin-3-yl)-1,2,3,4-tetrahydropyrido[4,3-d]pyrimidin-7-yl)methyl)acrylamide or a pharmaceutically acceptable salt thereof, and wherein the cancer is hepatocellular carcinoma.

17. The method of claim 1, wherein the compound is N-((6'-(2,6-difluoro-3,5-dimethoxyphenyl)-7'-oxo-6',7'-dihydro-5'H-spiro[cyclopropane-1,8'-pyrido[4,3-d]pyrimidine]-2'-yl)methyl)acrylamide or a pharmaceutically acceptable salt thereof, and wherein the cancer is hepatocellular carcinoma.

18. The method of claim 1, wherein the cancer is rhabdomyosarcoma.

19. The method of claim 1, wherein the cancer is colorectal cancer.

20. The method of claim 1, wherein the cancer is prostate cancer.

21. The method of claim 1, wherein the cancer is kidney cancer.

\* \* \* \* \*

UNITED STATES PATENT AND TRADEMARK OFFICE
CERTIFICATE OF CORRECTION

PATENT NO. : 10,738,048 B2
APPLICATION NO. : 16/239051
DATED : August 11, 2020
INVENTOR(S) : Liang Lu et al.

Page 1 of 1

It is certified that error appears in the above-identified patent and that said Letters Patent is hereby corrected as shown below:

In the Claims

Column 84, Line 18, Claim 10, delete "N-{([2'" and insert -- N{[2' --.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*